United States Patent
Kelso et al.

(10) Patent No.: US 11,884,918 B2
(45) Date of Patent: Jan. 30, 2024

(54) SYSTEMS AND METHODS FOR MODULATING CRISPR ACTIVITY

(71) Applicant: Synthego Corporation, Redwood City, CA (US)

(72) Inventors: Reed Kelso, San Francisco, CA (US); Jared Carlson-Stevermer, Burlingame, CA (US); Sahil Joshi, Somerville, MA (US); Travis Maures, La Jolla, CA (US); Anastasia Kadina, Sunnyvale, CA (US); John Andrew Walker, II, San Leandro, CA (US)

(73) Assignee: Synthego Corporation, Redwood City, CA (US)

( * ) Notice: Subject to any disclaimer, the term of this patent is extended or adjusted under 35 U.S.C. 154(b) by 0 days.

(21) Appl. No.: 17/384,328

(22) Filed: Jul. 23, 2021

(65) Prior Publication Data

US 2022/0073912 A1 Mar. 10, 2022

Related U.S. Application Data

(63) Continuation of application No. PCT/US2020/015127, filed on Jan. 25, 2020.

(60) Provisional application No. 62/939,553, filed on Nov. 22, 2019, provisional application No. 62/876,177, filed on Jul. 19, 2019, provisional application No. 62/797,122, filed on Jan. 25, 2019.

(51) Int. Cl.
| | |
|---|---|
| *C12N 15/113* | (2010.01) |
| *C12N 15/11* | (2006.01) |
| *C12N 9/22* | (2006.01) |
| *C12N 15/10* | (2006.01) |

(52) U.S. Cl.
CPC ............ *C12N 15/111* (2013.01); *C12N 9/22* (2013.01); *C12N 15/102* (2013.01); *C12N 2310/20* (2017.05)

(58) Field of Classification Search
CPC ...... C12N 15/111; C12N 9/22; C12N 15/102; C12N 2310/20
See application file for complete search history.

(56) References Cited

U.S. PATENT DOCUMENTS

| | | | |
|---|---|---|---|
| 5,849,902 A | 12/1998 | Arrow | |
| 7,897,737 B2 | 3/2011 | Wu | |
| 8,603,996 B2 | 12/2013 | Galloway | |
| 9,932,566 B2 | 4/2018 | Kennedy | |
| 2008/0227742 A1 | 9/2008 | Dmochowski | |
| 2010/0022761 A1 | 1/2010 | Chen | |
| 2010/0216804 A1 | 8/2010 | Zale | |
| 2010/0303850 A1 | 12/2010 | Lipford | |
| 2011/0020388 A1 | 1/2011 | Zepp | |
| 2011/0027217 A1 | 2/2011 | Zepp | |
| 2011/0217377 A1 | 9/2011 | Zale | |
| 2012/0171229 A1 | 7/2012 | Zepp | |
| 2012/0178702 A1 | 7/2012 | Huang | |
| 2014/0235508 A1 | 8/2014 | Nemoto | |
| 2016/0206566 A1 | 7/2016 | Lu | |
| 2016/0215300 A1 | 7/2016 | May | |
| 2017/0114334 A1 | 4/2017 | May | |

FOREIGN PATENT DOCUMENTS

| | | |
|---|---|---|
| WO | 1998013526 A1 | 4/1998 |
| WO | 2008103276 | 8/2008 |
| WO | 2010005740 | 1/2010 |
| WO | 2010030763 | 3/2010 |
| WO | 2010075072 | 7/2010 |
| WO | 2010138192 | 12/2010 |
| WO | 2010138193 | 12/2010 |
| WO | 2010138194 | 12/2010 |
| WO | 2011084518 | 7/2011 |
| WO | 2011127255 | 10/2011 |
| WO | 2012092552 | 7/2012 |
| WO | 2012099755 | 7/2012 |
| WO | 2017155408 A1 | 9/2017 |
| WO | 2017184799 A1 | 10/2017 |

OTHER PUBLICATIONS

Olejnik, J., et al. "Photocleavable aminotag phosphoramidites for 5'-termini DNA/RNA labeling." Nucleic acids research 26.15 (1998): 3572-3576.
Ordoukhanian, P. et al. Design and synthesis of a versatile photocleavable DNA building block. Application to phototriggered hybridization. J. Am. Chem. Soc. 117, 9570-9571 (1995).
Ortigao, J. F. R. et al. "Antisense effect of oligodeoxynucleotides with inverted terminal internucleotidic linkages: a minimal modification protecting against nucleolytic degradation." Antisense research and development 2.2 (1992): 129-146.
Pearson, W. R., et al. "Improved tools for biological sequence comparison." Proceedings of the National Academy of Sciences 85.8 (1988): 2444-2448.
Rose, J. C. et al. Rapidly inducible Cas9 and DSB-ddPCR to probe editing kinetics. Nat. Methods 14, 891-896 (2017).
Samarsky, D. A., et al. "A small nucleolar RNA: ribozyme hybrid cleaves a nucleolar RNA target in vivo with near-perfect efficiency." Proceedings of the National Academy of Sciences 96.12 (1999): 6609-6614.
Scaringe, S. A. "[1] Advanced 5'-silyl-2'-orthoester approach to RNA oligonucleotide synthesis." (2000): 3-18.
Scaringe, S. A., et al. "Novel RNA synthesis method using 5 '-O-Silyl-2 '-O-orthoester protecting groups." Journal of the American Chemical Society 120.45 (1998): 11820-11821.

(Continued)

*Primary Examiner* — J. E. Angell
(74) *Attorney, Agent, or Firm* — Quarles & Brady LLP

(57) ABSTRACT

Provided herein are polynucleotides comprising sequence configured to bind to a CRISPR effector protein. Modulation of one or more modifications of the polynucleotides can be used to tune the activity of CRISPR effector proteins complexed with the polynucleotides.

9 Claims, 43 Drawing Sheets
Specification includes a Sequence Listing.

(56) References Cited

OTHER PUBLICATIONS

Schroeder, A., et al. "Lipid-based nanotherapeutics for siRNA delivery." Journal of internal medicine 267.1 (2010): 9-21.
Shen, C.-C. et al. Synthetic switch to minimize CRISPR off-target effects by self-restricting Cas9 transcription and translation. Nucleic Acids Res. 47, e13-e13 (2019).
Shukla, S. et al. "Exploring chemical modifications for siRNA therapeutics: a structural and functional outlook." ChemMedChem 5.3 (2010): 328-349.
Siegwart, D. J., et al. "Combinatorial synthesis of chemically diverse core-shell nanoparticles for intracellular delivery." Proceedings of the National Academy of Sciences 108.32 (2011): 12996-13001.
Sigman, D. S., et al. "Chemical nucleases." Chemical Reviews 93.6 (1993): 2295-2316.
Sigman, D. S., et al. "Targeted chemical nucleases." Accounts of Chemical Research 26.3 (1993): 98-104.
Slaymaker, I. M. et al. Rationally engineered Cas9 nucleases with improved specificity. Science 351, 84-88 (2016).
Sletten, E.M. et al. "Bioorthogonal chemistry: fishing for selectivity in a sea of functionality." Angewandte Chemie International Edition 48.38 (2009): 6974-6998.
Smith, T. F., et al. "Comparison of biosequences." Advances in applied mathematics 2.4 (1981): 482-489.
Su, X., et al. "In vitro and in vivo mRNA delivery using lipid-enveloped pH-responsive polymer nanoparticles." Molecular pharmaceutics 8.3 (2011): 774-787.
Sulej, A. A., et al. "Sequence-specific cleavage of the RNA strand in DNA-RNA hybrids by the fusion of ribonuclease H with a zinc finger." Nucleic acids research 40.22 (2012): 11563-11570.
Tatusova, T. A., et al. "BLAST 2 Sequences, a new tool for comparing protein and nucleotide sequences." FEMS microbiology letters 174.2 (1999): 247-250.
Threlfall, R. N., et al. "Synthesis and biological activity of phosphonoacetate-and thiophosphonoacetate-modified 2'-O-methyl oligoribonucleotides." Organic & biomolecular chemistry 10.4 (2012): 746-754.
Tsai et al. "GUIDE-seq enables genome-wide profiling of off-target cleavage by CRISPR-Cas nucleases", Nature Biotechnology 33, 187-197 (2015).
Van Devanter, et al. "Characterization of an adduct between CC-1065 and a defined oligodeoxynucleotide duplex." Nucleic acids research 12.15 (1984): 6159-6168.
Wang, Y., et al. "Co-delivery of drugs and DNA from cationic core-shell nanoparticles self-assembled from a biodegradable copolymer." Nature materials 5.10 (2006): 791-796.
Watts, J. K. et al. "Chemically modified siRNA: tools and applications." Drug discovery today 13.19-20 (2008): 842-855.
Werner M et al. "Short oligonucleotides as external guide sequences for site-specific cleavage of RNA molecules with human RNase P." Rna 4.7 (1998): 847-855.
Weyel, X. M. M., et al. A two-photon-photocleavable linker for triggering light-induced strand breaks in bligonucleotides. ACS Chem. Biol. 12, 2183-2190 (2017).
Wheeler, J. J., et al. "Stabilized plasmid-lipid particles: construction and characterization." Gene therapy 6.2 (1999): 271-281.
Zaug et al., "Sequence-specific endoribonuclease activity of the Tetrahymena ribozyme: enhanced cleavage of certain oligonucleotide substrates that form mismatched ribozyme-substrate complexes." Biochemistry 27.25 (1988): 8924-8931.
Zetsche, B. et al. (2016), "Multiplex gene editing by CRISPR-Cpf1 using a single crRNA array", Nature Biotechnology (2016) doi: 10.1038/nbt.3737.
Zhang, L., et al. "Self-assembled lipid-polymer hybrid nanoparticles: a robust drug delivery platform." ACS nano 2.8 (2008): 1696-1702.
Zhang, Y. P., et al. "Stabilized plasmid-lipid particles for regional gene therapy: formulation and transfection properties." Gene therapy 6.8 (1999): 1438-1447.
Zhou, W. et al. Spatiotemporal control of CRISPR/Cas9 function in cells and zebrafish using light-activated guide RNA. Angew. Chem. 132, 9083-9088 (2020).
Akinc, A., et al. "A combinatorial library of lipid-like materials for delivery of RNAi therapeutics." Nature biotechnology 26.5 (2008): 561-569.
Beaucage, S. L., et al. De-oxynucleoside phosphoramidites-a new class of key intermediates for deoxypolynucleotide syn. Tetrahedron Lett. 22: 1859-1862, 1981.
Behlke, M. A. "Chemical modification of siRNAs for in vivo use." Oligonucleotides 18.4 (2008): 305-320.
Beloglazova, N., et al. "A novel family of sequence-specific endoribonucleases associated with the clustered regularly interspaced short palindromic repeats." Journal of Biological Chemistry 283.29 (2008): 20361-20371.
Bohacova, S., et al. "Protected 5-(hydroxymethyl) uracil nucleotides bearing visible-light photocleavable groups as building blocks for polymerase synthesis of photocaged DNA." Organic & biomolecular chemistry 16.9 (2018): 1527-1535.
Boyle, E. A. et al. High-throughput biochemical profiling reveals sequence determinants of dCas9 off-target binding and unbinding. Proc. Natl Acad. Sci. USA 114, 5461-5466 (2017).
Briner, A. E. et al. Guide RNA functional modules direct Cas9 activity and orthogonality. Mol. Cell 56, 333-339 (2014).
Brinkman, E. K. et al. Kinetics and fidelity of the repair of Cas9-induced double-strand DNA breaks. Mol. Cell 70, 801-813.e6 (2018).
Brinkman, E. K., et al. "Easy quantitative assessment of genome editing by sequence trace decomposition." Nucleic acids research 42.22 (2014): e168-e168.
Buckup, T., et al. Optimisation of two-photon induced cleavage of molecular linker systems for drug delivery. J. Photochem. Photobiol. Chem. 210, 188-192 (2010).
Carlson-Stevermer, J., et al. "CRISPRoff enables spatio-temporal control of CRISPR editing." Nature communications 11.1 (2020): 1-7.
Chen, C. H., et al. "Chemical conversion of a DNA-binding protein into a site-specific nuclease." Science 237.4819 (1987): 1197-1201.
Chylinski, K. et al. CRISPR-Switch regulates sgRNA activity by Cre recombination for sequential editing of two loci. Nat. Commun. 10, 1-12 (2019).
De Koker, S., et al. "Polymeric multilayer capsules delivering biotherapeutics." Advanced drug delivery reviews 63.9 (2011): 748-761.
Dellinger, D. J., et al. "Solid-phase chemical synthesis of phosphonoacetate and thiophosphonoacetate bligodeoxynucleotides." Journal of the American Chemical Society 125.4 (2003): 940-950.
Dellinger, D. J., et al. "Streamlined process for the chemical synthesis of RNA using 2'-O-thionocarbamate- protected nucleoside phosphoramidites in the solid phase." Journal of the American Chemical Society 133.30 (2011): 11540-11556.
Dow, L. E. et al. Inducible in vivo genome editing with CRISPR-Cas9. Nat. Biotechnol. 33, 390-394 (2015).
Endres, T. K., et al. "Self-assembled biodegradable amphiphilic PEG-PCL-lPEI triblock copolymers at the borderline between micelles and nanoparticles designed for drug and gene delivery." Biomaterials 32.30 (2011): 7721-7731.
Fu, Y. et al. High-frequency off-target mutagenesis induced by CRISPR-Cas nucleases in human cells. Nat. Biotechnol. 31, 822-826 (2013).
Fukuma, T., et al. "Conjugation of an antisense oligodeoxynucleotide to ribonuclease H results in sequence-specific cleavage and intracellular inhibition of HCV gene expression." Bioconjugate chemistry 14.2 (2003): 295-301.
Fuller, J. E., et al. "Intracellular delivery of core-shell fluorescent silica nanoparticles." Biomaterials 29.10 (2008): 1526-1532.
Gangopadhyay, S. A. et al. Precision control of CRISPR-Cas9 using small molecules and light. Biochemistry 58, 234-244 (2019).
Garcia, B. et al. Anti-CRISPR AcrIIA5 potently inhibits all Cas9 homologs used for genome editing. Cell Rep. 29, 1739-1746.e5 (2019).
Glów, D., et al. "Sequence-specific cleavage of dsRNA by Mini-III RNase." Nucleic acids research 43.5 (2015): 2864-2873.

(56) References Cited

OTHER PUBLICATIONS

Gnaccarini, C., et al. "Site-specific cleavage of RNA by a metal-free artificial nuclease attached to antisense oligonucleotides." Journal of the American Chemical Society 128.24 (2006): 8063-8067.
González, F et al. An iCRISPR platform for rapid, multiplexable, and inducible genome editing in human pluripotent stem cells. Cell Stem Cell 15, 215-226 (2014).
Hendel, A., et al. "Chemically modified guide RNAs enhance CRISPR-Cas genome editing in human primary cells." Nature biotechnology 33.9 (2015): 985-989.
Hoffmann, M. D. et al. Optogenetic control of Neisseria meningitidis Cas9 genome editing using an engineered, light-switchable anti-CRISPR protein. Preprint at https://doi.org/10.1101/858589 (2019).
Hisiau, T., et al. "Inference of CRISPR edits from Sanger trace data." BioRxiv (2018): 251082.
International Searching Authority. International Search Report and Written Opinion for application PCT/US2020/015127. dated Jul. 22, 2020. 23 pages.
Jain, P. K., et al. "Development of Light-Activated CRISPR Using Guide RNAs with Photocleavable Protectors." Angewandte Chemie International Edition 55.40 (2016): 12440-12444.
Jeffs, L. B., et al. "A scalable, extrusion-free method for efficient liposomal encapsulation of plasmid DNA." Pharmaceutical research 22.3 (2005): 362-372.
Jinek, M. et al. A programmable dual RNA-guided DNA endonuclease in adaptive bacterial immunity. Science 337, 816-821 (2012).
Kim, S., et al. Highly efficient RNA-guided genome editing in human cells via delivery of purified Cas9 ribonucleoproteins. Genome Res. 24, 1012-1019 (2014).
Klein, M., et al. Hybridization kinetics explains CRISPR-Cas off-targeting rules. Cell Rep. 22, 1413-1423 (2018).
Kleinstiver, B. P. et al. High-fidelity CRISPR-Cas9 variants with undetectable genome-wide off-targets. Nature 529, 490-495 (2016).
Kundert, K. et al. Controlling CRISPR-Cas9 with ligand-activated and liganddeactivated sgRNAs. Nat. Commun. 10, 1-11 (2019).
Levy, M., et al. "Direct selection of trans-acting ligase ribozymes by in vitro compartmentalization." Rna 11.10 (2005): 1555-1562.
Li, H. "Structural principles of CRISPR RNA processing." Structure 23.1 (2015): 13-20.
Liu, Q. "Synthesis of Photo/Chemical-Activated Nucleosides and Unnatural Amino Acids." Dissertation. North Carlina State University. pp. 1-296. (2014).
Liu, Y. et al. Very fast CRISPR on demand. Science 368, 1265-1269 (2020).

Love, K. T., et al. "Lipid-like materials for low-dose, in vivo gene silencing." Proceedings of the National Academy of Sciences of the United States of America 107.5 (2010): 1864.
Mahon, K. P., et al. "Combinatorial approach to determine functional group effects on lipidoid-mediated siRNA delivery." Bioconjugate chemistry 21.8 (2010): 1448-1454.
Manoharan, M. "RNA interference and chemically modified small interfering RNAs." Current opinion in chemical biology 8.6 (2004): 570-579.
Matteucci, M. D., et al. "Synthesis of deoxyoligonucleotides on a polymer support." Journal of the American Chemical Society 103.11 (1981): 3185-3191.
Morrissey, D. V., et al. "Potent and persistent in vivo anti-HBV activity of chemically modified siRNAs." Nature biotechnology 23.8 (2005): 1002-1007.
Needleman, S. B., et al. "A general method applicable to the search for similarities in the amino acid sequence of two proteins." Journal of molecular biology 48.3 (1970): 443-453.
Nguyen, D. P. et al. Ligand-binding domains of nuclear receptors facilitate tight control of split CRISPR activity. Nat. Commun. 7, 1-10 (2016).
Nihongaki, Y., et al. Photoactivatable CRISPRCas9 for optogenetic genome editing. Nat. Biotechnol. 33, 755-760 (2015).
Nishimasu, H. et al. Crystal structure of Cas9 in complex with guide RNA and target DNA. Cell 156, 935-949 (2014).
Biosynthesis. Maleimide Oligonucleotide Modification. 2018. [online]. [Version dated Jun. 20, 2018]. Retrieved from the internet URL https://web.archive.org/web/20180620150124/https://www.biosyn.com/oligonucleotideproduct/maleimide-oligonucleotide-modification.aspx.
Chen, B., et al. "Dynamic imaging of genomic loci in living human cells by an optimized CRISPR/Cas system." Cell 155.7 (2013): 1479-1491.
International Searching Authority. International Search Report and Written Opinion for application PCT/US2020/042681. dated Dec. 3, 2020. 14 pages.
RCSB Protein Data Bank. 4008 Crystal Structure of Strep. Version dated May 9, 2019. Available online at http://web.archive.org/web/20190509184951/https://www.rcsb.org/structure/4008.
Wenzel, T., et al. "Genosnip: SNP genotyping by MALDI-TOF MS using photocleavable oligonucleotides." Nucleosides, Nucleotides and Nucleic Acids 22.5-8 (2003): 1579-1581.
Xu, J., et al. "Evolution and characterization of a benzylguanine-binding RNA aptamer." Chemical Communications 52.3 (2016): 549-552.

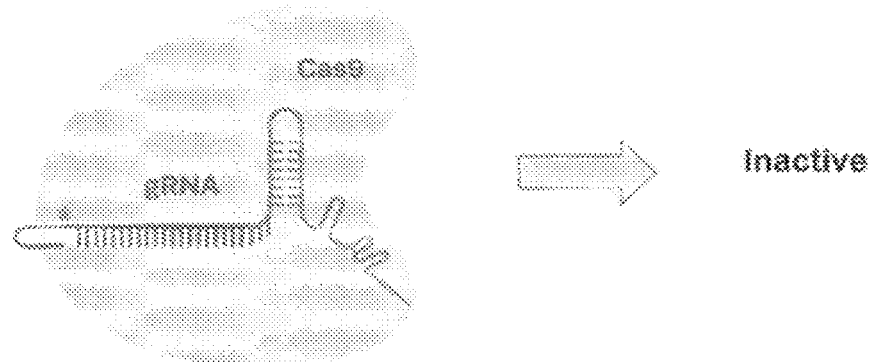
FIG. 1A
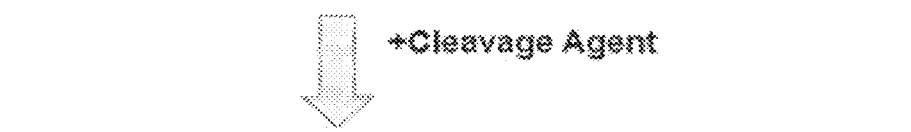
FIG. 1B
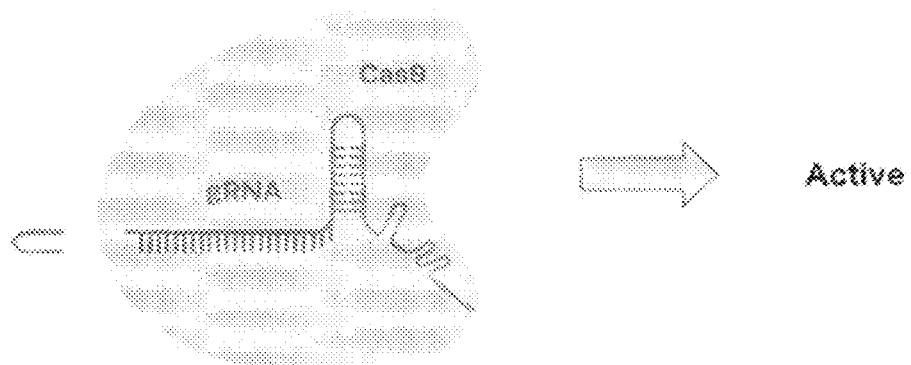
FIG. 1C
FIG. 1

*5 different UV Photocleavable gRNAs

-b21; inactive

-b24; inactive

-b50; inactive

-b57; active, UV attenuates activity

-b74; active UV attenuates activity

SYSTEMS AND METHODS FOR MODULATING CRISPR ACTIVITY

CROSS-REFERENCE

This application is a continuation application of international application PCT/US2020/015127, filed Jan. 25, 2020, which international application claims priority to U.S. provisional patent application No. 62/797,122, filed Jan. 25, 2019, U.S. provisional patent application No. 62/876,177, filed Jul. 19, 2019, and U.S. provisional patent application No. 62/939,553, filed Nov. 22, 2019 which are herein incorporated by reference in their entireties.

SEQUENCE LISTING

A Sequence Listing accompanies this application and is submitted as an ASCII text file of the sequence listing named "2021-07-23_174774.00065_SEQUENCE LISTING" which is 38.7 KB in size and was created on Jul. 23, 2021. The sequence listing is electronically submitted via EFS-Web with the application and is incorporated herein by reference in its entirety.

BACKGROUND

Nucleic acid editing can be used for treating genetic disease. State-of-the-art editing machinery can be inherently uncontrollable, both in the delivery of the machinery to target cells and once editing machinery is introduced into a cell. Due to this uncontrollability, modifications can be introduced at undesired locations within the genome, known as off-target effects. Undesired off-target activity of Cas nucleases can lead to catastrophic biological events, including chromosomal translocations. The activity of a CRISPR ribonucleoprotein (RNP) can also create challenges for in vivo editing. Furthermore, the systemic delivery to an organism can result in on-target edits in desired as well as unintended cell types. Improving genome editing specificity is therefore a topic of scientific and therapeutic interest Programmable nucleic acid editing can have broad biological and therapeutic applications. Programmable nucleic acid editing can refer to the ability to engineer nuclease-based platforms, such as a CRISPR RNP comprising a CRISPR effector protein and a CRISPR polynucleotide comprising a sequence configured to anneal to target sequence of a target nucleic acid molecule and sequence configured to bind to the CRISPR effector protein (e.g., Cas9), for increasingly precise control of the activity and recognition of various target sites across genomes or transcriptomes.

Modification of the CRISPR polynucleotides that can be complexed with the CRISPR effector proteins can be a viable and powerful alternative approach to programmable genome editing. There is a need for CRISPR polynucleotides that can be complexed with CRISPR effector proteins that allow for reduced off-target editing activity and the controllable induction and cessation of genome editing activity and persistence of CRISPR effector protein/CRISPR polynucleotide complex.

SUMMARY

In one aspect, provided herein is a method of cleaving a polynucleotide, wherein the polynucleotide comprises (i) a guide sequence configured to anneal to a target sequence in a target nucleic acid molecule, (ii) a sequence configured to bind to a CRISPR enzyme, and (iii) a cleavable linker 3' of the 5' most nucleotide of the guide sequence, the method comprising exposing the polynucleotide to a cleavage agent thereby cleaving the cleavable linker. The cleavage agent can be UV light. The cleavage agent can be visible light. In some embodiments, the cleavable linker is not a naturally occurring nucleic acid. In some embodiments, the cleavable linker is not at the 3' end of the polynucleotide. The cleavable linker can comprises a photolabile linker. The photolabile linker can be cleavable by ultraviolet radiation. The photolabile linker can be cleavable by visible light. The cleavable linker can comprise 3-(4,4'-Dimethoxytrityl)-1-(2-nitrophenyl)-propan-1-yl-[(2-cyanoethyl)-(N,N-diisopropyl)]-phosphoramidite. The cleavable linker can comprise 1-(7-(diethylamino)-2-oxo-2H-chromen-4-yl)propyl. The cleavable linker can comprise

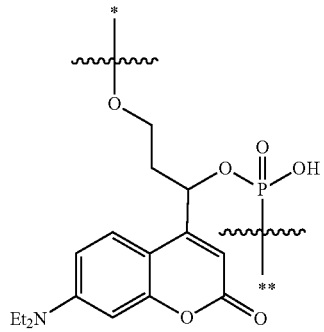

wherein * indicates a point of attachment to H, or a first nucleotide and ** indicates a point of attachment to OH, or a second nucleotide. The photolabile linker can comprise phosphoramidite. The photolabile linker can comprise coumarin. The cleavable linker can be positioned within a tracrRNA sequence. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The polynucleotide can comprise a tetraloop, a nexus, a stem loop 1, and a stem loop 2 from 5' to 3', wherein the cleavable linker is in a loop of the nexus or a loop of the stem loop 1. The cleavable linker can be in a loop of a nexus or a loop of stem loop 1, numbered 5' to 3'. The tetraloop can comprise nucleotides 21-51. The nexus can comprise nucleotides 52-62. Stem Loop 1 can comprise nucleotides 68-81. Stem Loop 2 can comprise nucleotides 81-97. The cleavable linker can be in a loop of nexus and a loop of stem loop 1, numbered 5' to 3'. The cleavable linker can be positioned immediately 3' of nucleotide 56 or 73 in the polynucleotide, wherein a nucleotide at a 5' end of the guide sequence is nucleotide 1, and nucleotides are numbered in order from the end of the guide sequence to a 3' end of the polynucleotide. The cleavable linker can be positioned immediately 3' of nucleotide 56 and another cleavable linker can be positioned immediate 3' of nucleotide 73 in the polynucleotide, wherein a nucleotide at a 5' end of the guide sequence is nucleotide 1, and nucleotides are numbered in order from the 5' end of the guide sequence to a 3' end of the polynucleotide.

In another aspect, provided herein is a polynucleotide comprising a guide sequence configured to anneal to a target sequence in a target nucleic acid molecule; a sequence configured to bind to a CRISPR enzyme; and a cleavable linker cleavable by light at a wavelength greater than 420 nm. The cleavable linker can comprise 1-(7-(diethylamino)-2-oxo-2H-chromen-4-yl)propyl. The cleavable linker can comprise

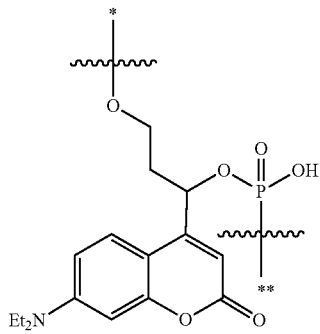

wherein * indicates a point of attachment to H, or a first nucleotide and ** indicates a point of attachment to OH, or a second nucleotide. The cleavable linker can comprise coumarin. The cleavable linker can comprise phosphoramidite. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The polynucleotide can comprises a tetraloop, a nexus, a stem loop 1 and a stem loop 2 from 5' to 3', wherein the cleavable linker is in a loop of the nexus or a loop of the stem loop 1. The cleavable linker can be in a loop of the nexus and a loop of the stem loop 1, numbered 5' to 3'. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The polynucleotide can comprise another cleavable linker, wherein the cleavable linker is positioned immediately 3' of nucleotide 56 and another cleavable linker is positioned immediately 3' of nucleotide 73 in the polynucleotide, wherein a nucleotide at a 5' end of the guide sequence is nucleotide 1, and nucleotides are numbered in order from the 5' end of the guide sequence to a 3' end of the polynucleotide. A first cleavable linker can be positioned immediately 3' of nucleotide 56 in the polynucleotide and a second cleavable linker can be positioned immediately 3' of nucleotide 73 in the polynucleotide, wherein a nucleotide at a 5' end of the guide sequence is nucleotide 1, and nucleotides are numbered in order from the 5' end of the guide sequence to a 3' end of the polynucleotide.

In another aspect, provided herein is a polynucleotide comprising: a guide sequence configured to anneal to a target nucleic acid sequence in a target nucleic acid molecule; a sequence configured to bind to a CRISPR enzyme; and a cleavable linker cleavable by visible light. The cleavable linker can comprise

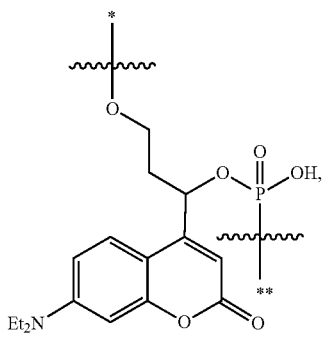

wherein * indicates a point of attachment to H, or a first nucleotide; and ** indicates a point of attachment to OH, or a second nucleotide. The visible light can comprise a wavelength greater than 385 nm. The cleavable linker can comprise coumarin. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The polynucleotide can comprise another cleavable linker, wherein the cleavable linker is positioned immediately 3' of nucleotide 56 in the polynucleotide and the another cleavable linker is positioned immediately 3' of nucleotide 73 in the polynucleotide, wherein a nucleotide at a 5' end of the guide sequence is nucleotide 1, and nucleotides are numbered in order from the 5' end of the guide sequence to a 3' end of the polynucleotide. The polynucleotide can comprise a tetraloop, a nexus, a stem loop 1 and a stem loop 2 from 5' to 3', wherein the cleavable linker is in a loop of the nexus or a loop of the stem loop 1. The cleavable linker can be in a loop of a stem loop of the polynucleotide. The cleavable linker can be in a loop of the nexus or a loop of the stem loop 1, numbered 5' to 3'. The polynucleotide can comprise a second cleavable linker, wherein the first cleavable linker is in a loop of the nexus and the second cleavable linker is in a loop of the stem loop 1 of the polynucleotide.

In another aspect, provided herein is a method comprising: introducing a CRISPR complex comprising the aforementioned polynucleotide into a cell; and exposing the polynucleotide to a cleaving agent thereby cleaving the cleavable linker. The method can further comprise prior to (a), complexing the aforementioned polynucleotide to a CRISPR enzyme.

In another aspect, provided herein is a method comprising exposing the polynucleotide to light, thereby cleaving the polynucleotide at the photolabile linker. The polynucleotide can be complexed with a CRISPR enzyme. The polynucleotide can be present in a cell. The polynucleotide can be outside a cell. The exposing can reduce the target-specific cleavage activity of the CRISPR enzyme complexed with the polynucleotide.

In another aspect, provided herein is a polynucleotide comprising (a) a guide sequence configured to anneal to a target sequence in a target nucleic acid molecule; (b) a sequence configured to bind to a CRISPR enzyme; and (c) a cleavable linker positioned (i) 3' of a 5' most base in the guide sequence and (ii) outside of a tetraloop of the polynucleotide. The cleavage agent can be UV light. The cleavage agent can be visible light. In some embodiments the cleavable linker is not a naturally occurring nucleic acid. In some embodiments, the cleavable linker is not at the 3' end of the polynucleotide. The cleavable linker can comprises a photolabile linker. The photolabile linker can be cleavable by ultraviolet radiation. The photolabile linker can be cleavable by visible light. The cleavable linker can comprise 3-(4,4'-Dimethoxytrityl)-1-(2-nitrophenyl)-propan-1-yl-[(2-cyanoethyl)-(N,N-diisopropyl)]-phosphoramidite. The cleavable linker can comprise 1-(7-(diethylamino)-2-oxo-2H-chromen-4-yl)propyl. The cleavable linker can comprise

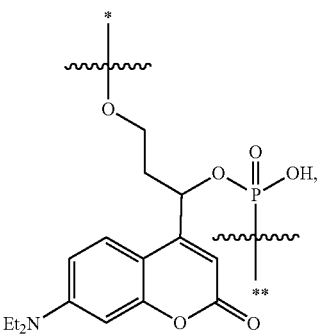

wherein * indicates a point of attachment to H, or a first nucleotide; and ** indicates a point of attachment to OH, or a second nucleotide. The cleavable linker can be a photolabile linker. The photolabile linker can comprise phosphoramidite. The photolabile linker can comprise coumarin. The cleavable linker can be positioned within a tracrRNA sequence. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The cleavable linker can be in a loop of nexus or a loop of stem loop 1, numbered 5' to 3'. The cleavable linker can be in a loop of nexus and a loop of stem loop 1, numbered 5' to 3'. The cleavable linker can be positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide. The cleavable linker can be positioned immediately 3' of nucleotide 56 and 73 in the polynucleotide, wherein a nucleotide at a 5' end of the guide sequence is nucleotide 1, and nucleotides are numbered in order from the 5' end of the guide sequence to a 3' end of the polynucleotide.

In another aspect, provided herein is a method comprising: introducing a CRISPR complex comprising the aforementioned polynucleotide; and exposing the polynucleotide to a cleavage agent configured to cause cleavage of the cleavable linker, thereby cleaving the cleavable linker. The method can further comprise, prior to (a), complexing the aforementioned polynucleotide to a CRISPR enzyme.

In another aspect, provided herein is a polynucleotide comprising (a) a guide sequence configured to anneal to a target sequence in a target nucleic acid molecule; (b) a sequence configured to bind to a CRISPR enzyme; (c) a first element configured to be subjected to a first specific modification that generates a first modified polynucleotide that, when complexed with a CRISPR enzyme, forms a first CRISPR complex with higher target-specific cleavage activity than a CRISPR complex comprising the polynucleotide that has not had been subjected to the first specific modification; and (d) a second element configured to be subjected to a second specific modification to generate a second modified polynucleotide that, when complexed with a CRISPR enzyme, forms a second CRISPR complex with a lower target-specific cleavage activity than the first CRISPR complex. The polynucleotide can comprise a sequence element 5' of the guide sequence. The sequence element can comprise RNA. The sequence element can form a stem loop. In some embodiments, the stem loop does not comprise a base-pair to the guide sequence. The stem loop can comprise a base-pair to the guide sequence. The 5'-most base of the stem loop can anneal to a base in the sequence element immediately 5' of the guide sequence. The first element can comprise a first cleavable linker. The first cleavable linker can be positioned immediately 5' of the guide sequence. The first cleavable linker can be susceptible to cleavage by light, presence of a small molecule, or a cellular process. The first cleavable linker can comprise a photolabile linker. The first cleavable linker can comprise 3-(4,4'-Dimethoxytrityl)-1-(2-nitrophenyl)-propan-1-yl-[(2-cyanoethyl)-(N,N-diisopropyl)]-phosphoramidite. The first cleavable linker can comprise

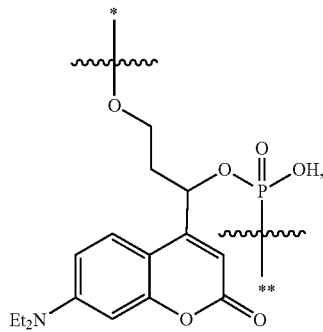

wherein * indicates a point of attachment to H, or a first nucleotide; and ** indicates a point of attachment to OH, or a second nucleotide. The second element can be a same type of element as the first element. The second element can be a different type of element as the first element. The polynucleotide when complexed with a CRISPR enzyme, can comprise a substantially similar target-specific cleavage activity as the polynucleotide without the second element when complexed with a CRISPR enzyme. The polynucleotide second element can comprise a second cleavable linker. The second cleavable linker can be positioned in the sequence configured to bind to a CRISPR enzyme. The second cleavable linker can be positioned immediately 3' of nucleotide 56 or 73 in the polynucleotide, wherein a nucleotide at a 5' end of the guide sequence can be nucleotide 1, and nucleotides are numbered in order from the 5' end of the guide sequence to a 3' end of the polynucleotide.

In another aspect, provided herein, is a method comprising subjecting the first element of the aforementioned polynucleotide to a first specific modification, thereby generating the first modified polynucleotide. The method can further comprise complexing the first modified polynucleotide with the CRISPR enzyme, thereby forming the first CRISPR complex. The polynucleotide can comprise a sequence element 5' of the guide sequence. The sequence element can comprise RNA. The sequence element can form a stem loop. In some embodiments, the stem loop does not comprise a base-pair to the guide sequence. The stem loop can comprise a base-pair to the guide sequence. A 5'-most base of the stem loop can anneal to a base in the sequence element immediately 5' of the guide sequence. The first element can comprise a first cleavable linker. The first cleavable linker can be positioned immediately 5' of the guide sequence. The first cleavable linker can comprise a photolabile linker. The first specific modification can comprise specific cleavage of the cleavable linker. Subjecting the first element to the first specific modification can comprise exposing the polynucleotide to light. The light can comprise ultraviolet light. The method can further comprise subjecting the second element to the second specific modification after the subjecting the first element to the first modification, thereby forming the second modified polynucleotide. The second element can comprise a photolabile linker. The second cleavable linker can be positioned in the sequence configured to bind to a CRISPR enzyme. The second cleavable linker can be positioned immediately 3' of nucleotide 56 or 73 in the polynucleotide, wherein a nucleotide at a 5' end of the guide sequence can be nucleotide 1, and nucleotides are numbered in order from the 5' end of the guide sequence to a 3' end of the polynucleotide. The first cleavable linker can be positioned immediately 3' of nucleotide 56 and the second cleavable linker can be positioned immediately 3' of nucleotide 73 in the polynucleotide, wherein a nucleotide at a 5' end of the guide sequence can be nucleotide 1, and nucleotides are numbered in order from the 5' end of the guide sequence to a 3' end of the polynucleotide. The polynucleotide can comprise a first stem loop wherein the cleavable linker can be in nexus or stem loop 1, numbered from a 5' end to a 3' end of the polynucleotide. The second cleavable linker can be positioned in a loop of nexus or a loop of stem loop 1, and stem loops are numbered in order from the 5' end of the guide sequence to a 3' end of the polynucleotide. The first cleavable linker can be positioned in a loop of nexus and the second cleavable linker can be positioned in a loop of stem loop 1, and stem loops are numbered in order from the 5' end of the guide sequence to a 3' end of the polynucleotide. Subjecting the second element to the second specific modification can comprise exposing the first modified polynucleotide to another light. The another light can comprise ultraviolet light. The another light can comprise light wavelengths greater than 420 nm.

In another aspect, provided herein is a polynucleotide comprising a guide sequence configured to anneal to a target sequence in a target nucleic acid molecule, a sequence configured to bind to a CRISPR enzyme, and a first cleavable linker positioned 3' of the 5' most base of the guide sequence, wherein the cleavable linker does not comprise a photolabile linker, wherein the cleavable linker is not naturally occurring in nucleic acid. In some embodiments, the cleavable linker is not at the 3' end of the polynucleotide. The first cleavable linker can be positioned in the sequence configured to bind to a CRISPR enzyme.

In another aspect, disclosed herein is a method comprising exposing the aforementioned polynucleotide to an agent capable of cleaving the cleavable linker, thereby cleaving the cleavable linker.

In another aspect, disclosed herein is a polynucleotide comprising a guide sequence configured to anneal to a target sequence in a target nucleic acid molecule, a sequence configured to bind to a CRISPR enzyme, a sequence element covalently linked to a 5' end of the guide sequence and hybridized to the guide sequence, and a photolabile group positioned between the sequence element and the 5' end of the guide sequence. The sequence element can comprise RNA. The sequence element forms a stem loop. In some embodiments, the stem loop does not comprise a base-pair to the guide sequence. The stem loop can comprise a base-pair to the guide sequence. A 5'-most base of the stem loop can anneal to a base in the sequence element immediately 5' of the guide sequence. The photolabile group can comprise 3-(4,4'-Dimethoxytrityl)-1-(2-nitrophenyl)-propan-1-yl-[(2-cyanoethyl)-(N,N-diisopropyl)]-phosphoramidite. The photolabile group can comprise

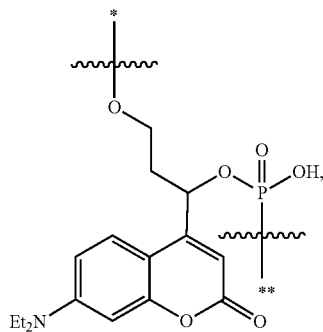

wherein * indicates a point of attachment to H, or a first nucleotide; and ** indicates a point of attachment to OH, or a second nucleotide.

In another aspect, disclosed herein is a method comprising: introducing a CRISPR complex comprising the aforementioned polynucleotide; and exposing the polynucleotide to light, thereby cleaving the polynucleotide at the photolabile linker. The method can comprise, prior to (a), complexing the aforementioned polynucleotide to a CRISPR enzyme. The polynucleotide can be complexed with a CRISPR enzyme. In some embodiments, the polynucleotide is not in a cell. The polynucleotide can be in a cell. Exposing can reduce target-specific cleavage activity of the CRISPR enzyme complexed with the polynucleotide.

In another aspect, disclosed herein is a method comprising specifically cleaving a polynucleotide comprising a guide sequence configured to anneal to a target sequence in a target nucleic acid molecule and a sequence configured to bind to a CRISPR enzyme, thereby reducing target-specific cleavage activity of a CRISPR enzyme complexed with the polynucleotide. The polynucleotide can comprise a cleavable linker. The cleavable linker can comprise a photolabile linker. The cleaving can comprise cleaving the polynucleotide at the photolabile linker. The cleavable linker can be positioned in the sequence configured to bind to a CRISPR enzyme. The cleavable linker can be positioned immediately 3' of nucleotide 56 or 73 in the polynucleotide, wherein a nucleotide at a 5' end of the guide sequence can be nucleotide 1, and nucleotides are numbered in order from the 5' end of the guide sequence to a 3' end of the polynucleotide. The first cleavable linker can be positioned immediately 3' of nucleotide 56 and the second cleavable linker can be positioned immediately 3' of nucleotide 73 in the polynucleotide, wherein a nucleotide at a 5' end of the guide sequence can be nucleotide 1, and nucleotides are numbered in order from the 5' end of the guide sequence to a 3' end of the polynucleotide. The polynucleotide can comprise a first stem loop wherein the cleavable linker can be in nexus or stem loop 1, numbered from a 5' end to a 3' end of the polynucleotide. The second cleavable linker can be positioned in a loop of nexus or a loop of stem loop 1, and stem loops are numbered in order from the 5' end of the guide sequence to a 3' end of the polynucleotide. The first cleavable linker can be positioned in a loop of nexus and the second cleavable linker can be positioned in a loop of stem loop 1, and stem loops are numbered in order from the 5' end of the guide sequence to a 3' end of the polynucleotide. In some embodiments, the polynucleotide and CRISPR enzyme are not in a cell. The polynucleotide and CRISPR enzyme can be in a cell.

In another aspect, disclosed herein, is a polynucleotide comprising: (i) a guide sequence configured to anneal to a target sequence in a target nucleic acid molecule and (ii) a sequence configured to bind to a CRISPR enzyme and comprising a modification; wherein when the polynucleotide can be complexed with a CRISPR enzyme, a first CRISPR complex can be formed having a lower editing activity of an off-target nucleic acid molecule than a second CRISPR complex comprising the polynucleotide, without the modification, complexed with the CRISPR enzyme. The modification can comprise a linker not comprising a canonical nucleotide base. The modification can comprise at least two linkers not comprising a canonical nucleotide base. The sequence of ii) can form, from 5' to 3', a tetraloop, a first stem loop, a second stem loop, and a third stem loop. In some embodiments, the polynucleotide does not comprise a fourth stem loop. In some embodiments, the polynucleotide does not comprise a stem loop at a 5' end of the polynucleotide. The linker can comprise a cleavable linker. The linker can comprise 3-(4,4'-Dimethoxytrityl)-1-(2-nitrophenyl)-propan-1-yl-[(2-cyanoethyl)-(N,N-diisopropyl)]-phosphoramidite. The linker can comprise

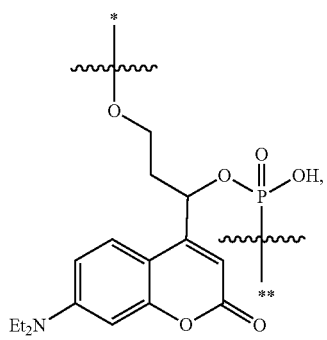

wherein * indicates a point of attachment to H, or a first nucleotide; and ** indicates a point of attachment to OH, or a second nucleotide. The modification can be at position 57 or position 74 of the polynucleotide, wherein position 1 can be at a 5' end of the guide sequence, and positions are counted from 5' to 3'. The modification can be at position 57 and position 74 of the polynucleotide. The modification can be in a loop of the tetraloop, the first stem loop, the second stem loop, or the third stem loop. The modification can be in the first stem loop or the second stem loop. The modification can be in a loop of first stem loop or a loop of the second stem loop. The modification can be at one or both of positions 57 and 74, wherein position 1 can be at a 5' end of the guide sequence, and positions are counted from 5' to 3'. The modification can comprise a photo cleavable bond. In some embodiments, the modification is not in a stem loop. The polynucleotide can comprise 2'-O-methyl analogs and 3'phosphorothioate inter nucleotide linkages at a first three 5' and 3' terminal RNA nucleotides. The editing activity can be measured as a percentage of off-target nucleic acid molecules that are edited. The editing activity of the off-target nucleic acid molecules by the first CRISPR complex can be lower that an editing activity of the second CRISPR complex with a p-value≤0.0001. An editing activity of the first CRISPR complex of the target nucleic acid molecule and an editing activity of the second CRISPR complex of the target nucleic acid molecule are within 5%. The editing activity of the first CRISPR complex of the target nucleic acid molecule and the editing activity of the second CRISPR complex of the target nucleic acid molecule are measured as a percentage of target nucleic acid molecules that are edited.

In another aspect, provided herein is a method comprising providing a first CRISPR complex to a cell, wherein the first complex can comprise the aforementioned polynucleotide complexed to a CRISPR enzyme, and editing a target sequence of the cell wherein the editing activity of an off-target nucleic acid molecule can be lower than a second CRISPR complex comprising a polynucleotide without a modification, complexed with the CRISPR enzyme.

In another aspect, provided herein is a CRISPR enzyme complexed with any of the above polynucleotides. In another aspect, provided herein is a pharmaceutical formulation comprising a CRISPR enzyme complexed with any of the above polynucleotides. In another aspect, provided herein is a kit comprising any of the aforementioned polynucleotides, and instructions. In another aspect, provided herein is pharmaceutical formulation comprising any of the aforementioned polynucleotides, and a pharmaceutically acceptable excipient. In another aspect, provided herein are methods comprising administering the pharmaceutical formulation to a subject. In another aspect, provided herein are methods comprising synthesizing any of the aforementioned polynucleotides. In another aspect, provided herein are methods comprising introducing any of the aforementioned polynucleotides into a cell. Disclosed herein is a method comprising introducing any of the aforementioned polynucleotides into a cell. In another aspect, provided herein, is a pharmaceutical formulation comprising the aforementioned cell.

In another aspect, described herein, is a nucleotide or oligonucleotide comprising a linker of Formula (I):

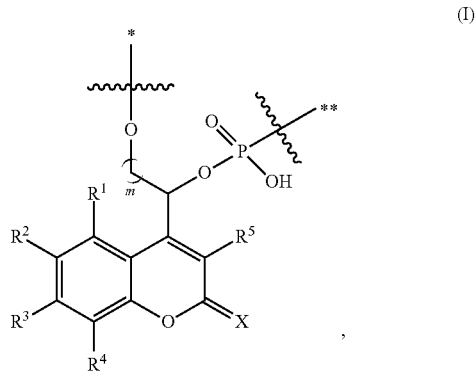

wherein: $R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; m can be an integer selected from 1 to 10; X can be selected from O, S, H, OTBDMS (O-tert-butyldimethylsilyl ether), dicyanomethylene or OMe; * can indicate a point of attachment to H, or a pentose moiety; and ** can indicate a point of attachment to OH, or a phosphate group of a nucleotide. The linker of Formula (I) can be represented by Formula (I'):

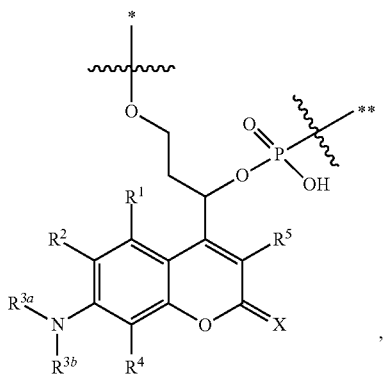

(I')

wherein: $R^1$, $R^2$, $R^{3a}$, $R^{3b}$, $R^4$, and $R^5$ are each independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^2$, $R^{2a}$, $R^{3a}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; X can be oxygen. $R^1$, $R^2$, $R^4$, and $R^5$ can each independently be H or $C_{1-6}$ alkyl; and $R^{3a}$, and $R^{3b}$ can be $C_{1-6}$ alkyl. $R^1$, $R^2$, $R^4$, and $R^5$ can each be H; and $R^{3a}$, and $R^{3b}$ can each be ethyl.

In another aspect, provided herein is a compound comprising

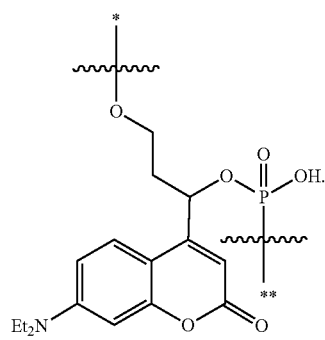

Disclosed herein is a polynucleotide comprising the aforementioned compound. The polynucleotide can further comprise a sequence configured to bind a CRISPR enzyme. The polynucleotide can further comprise a guide sequence configured to anneal to a target sequence in a target nucleic acid molecule. Disclosed herein is a CRISPR complex comprising a CRISPR enzyme and an aforementioned polynucleotide.

In another aspect, described herein, is a compound comprising Formula (I):

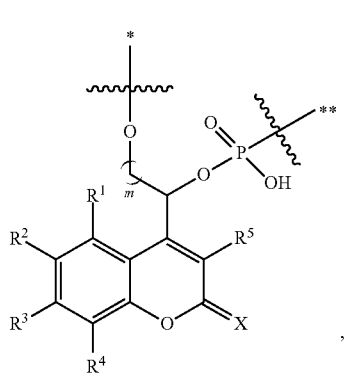

(I)

wherein: $R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

m can be an integer selected from 1 to 10; X can be selected from O, S, H, OTBDMS (O-tert-butyldimethylsilyl ether), dicyanomethylene or OMe; * can indicate a point of attachment to H, or a pentose moiety; and ** can indicate a point of attachment to OH, or a phosphate group of a nucleotide. The compound of Formula (I) can be represented by Formula (I'):

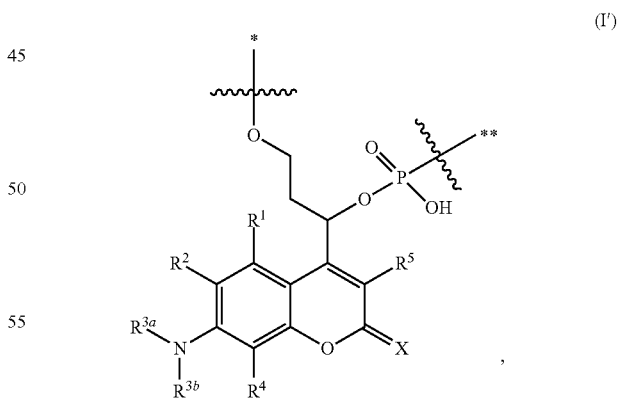

(I')

wherein: $R^1$, $R^2$, $R^{3a}$, $R^{3b}$, $R^4$, and $R^5$ are each independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^2$, $R^{2a}$, $R^{3a}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; X can be oxygen. $R^1$, $R^2$, $R^4$, and $R^5$ can each independently be H or $C_{1-6}$ alkyl; and $R^{3a}$, and $R^{3b}$ can be $C_{1-6}$ alkyl. $R^1$, $R^2$, $R^4$, and $R^5$ can each be H; and $R^{3a}$, and $R^{3b}$ can each be ethyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1C show an exemplary model of the activation of CRISPR-ON target cleavage activity. FIG. 1A illustrates a CRISPR-ON single guide RNA (sgRNA) comprising an added stem-loop structure located at the 5' end of the canonical sgRNA complexed with a CRISPR effector protein, Cas9. The stem-loop structure can repress activity of the complex resulting in an inactive complex. Addition of cleavage agent (FIG. 1B) can release the stem-loop structure (FIG. 1C), generating an active (ON) complex that can allow genome editing to occur.

DETAILED DESCRIPTION

I. Overview

Figure 2:
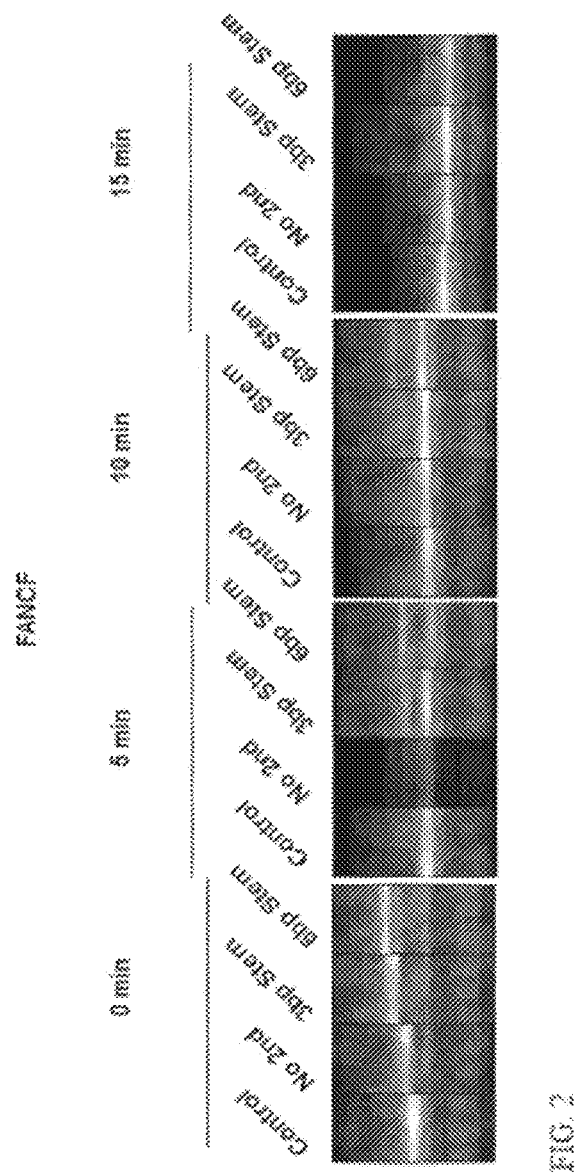
FIG. 2 shows the efficacy of cleavage of activatable CRISPR-ON sgRNA variants. CRISPR-ON sgRNAs comprising a 5' stem-loop element separated from guide sequence by a UV-susceptible cleavable linker were exposed to UV light for 0, 5, 10, or 15 minutes. Following minutes of exposure, the sgRNAs displayed a banding pattern consistent with cleavage of the sequence 5' of the guide sequence. The "Control" lane is a sgRNA lacking any additional sequence 5' of the guide sequence, and the "No 2nd" condition uses a sgRNA with a non-stem forming 5' addition to the guide sequence. The "3 bp stem" and the "6 bp stem" conditions use sgRNAs designed to have stem regions of 3 and 6 bp length at the 5' end of the guide sequence, respectively.

In general, provided herein are Clustered Regularly Interspaced Short Palindromic Repeats (CRISPR) polynucleotides (e.g., guide RNA (gRNA) or single guide RNA (sgRNA)) that can complex with CRISPR effector proteins, e.g., CRISPR enzyme, e.g., Cas9. The CRISPR polynucleotides can comprise (i) a sequence configured to bind to a CRISPR effector protein, (ii) optionally, a guide sequence configured to anneal to a target sequence in a target nucleic acid molecule, and (iii) one or more elements that can be modulated to affect the activity of a CRISPR effector protein complexed with the CRISPR polynucleotide. In some cases, a CRISPR effector protein complexed with the CRISPR polynucleotide can be considered to be "tunable." In some cases, the one or more elements can be modulated to increase the activity of a CRISPR effector protein complexed with the CRISPR polynucleotide (e.g., CRISPR "ON" complexes). In some cases, the one or more elements can be modulated to decrease the activity of a CRISPR effector protein complexed with the CRISPR polynucleotide (e.g., CRISPR "OFF" complexes). In some cases, a first element in the CRISPR polynucleotide can be modulated to increase the activity of a CRISPR effector protein complexed with the CRISPR polynucleotide and second element can be modulated to decrease the activity of a CRISPR effector protein complexed with the CRISPR polynucleotide (e.g., CRISPR "ON/OFF" complexes). Use of CRISPR complexes can be used to reduce off-target editing as compared to sgRNAs wherein the activity cannot be modulated. In some cases, one or more modifications can be introduced into the CRISPR polynucleotide such that, when complexed with a CRISPR effector protein, result in a CRISPR complex with lower off-target editing activity relative to the a CRISPR complex comprising the polynucleotide without the one or more modifications.

Also provided herein are complexes comprising a CRISPR effector protein complexed with the CRISPR polynucleotides (e.g., CRISPR ON complexes; CRISPR OFF complexes; or CRISPR ON/OFF complexes). Methods of modulating the CRISPR polynucleotides are provided herein. Kits comprising the polynucleotides and, e.g., instructions, and optionally CRISPR effector protein, are provided. Furthermore, pharmaceutical formulations comprising the CRISPR polynucleotides and a pharmaceutically acceptable excipient are provided, as well as methods of administering the pharmaceutical formulations. Methods of introducing the CRISPR polynucleotides into a cell are also provided herein.

A. CRISPR ON

Provided herein are CRISPR ON polynucleotides that can be complexed with CRISPR effector proteins to form CRISPR ON complexes. A CRISPR ON polynucleotide can comprise (i) a guide sequence configured to anneal to a target sequence in a target nucleic acid molecule (ii) a sequence (e.g., a tracrRNA sequence) configured to bind to a CRISPR effector protein, and (iii) a first sequence element 5' of the guide sequence. The first sequence element 5' of the guide sequence can be referred to as a polynucleotide leader sequence. The first sequence element can comprise a secondary structure, e.g., a stem loop. The stem loop can comprise from about 3 base pairs (bp) to about 30 bp. The 5' end of the first sequence element can be annealed to the base in the sequence element immediately 5' to the guide sequence. In some cases, the 5' end of the first sequence element is annealed to the guide sequence. The CRISPR ON polynucleotide can further comprise a first cleavable element, e.g., a first non-naturally occurring cleavable element, e.g., a photolabile linker. The cleavable element can be positioned immediately 5' of the guide sequence. The cleavable element can be susceptible to cleavage by light, small molecule, or one or more cellular processes. The polynucleotide leader sequence can interfere with the ability of the guide sequence to anneal to a target sequence.

Complexes comprising a CRISPR effector protein and the CRISPR ON polynucleotide can be assembled (see e.g., FIG. 1A). A CRISPR complex comprising a CRISPR ON polynucleotide with a first sequence element 5' of the guide sequence and a CRISPR effector protein can have a lower target specific activity than a CRISPR complex comprising a CRISPR polynucleotide without the first sequence element; for example, the activity can be about 2 fold to about 100 fold lower. Provided herein are methods for the tunable targeting of a CRISPR complex to a target nucleic acid, e.g., DNA. The methods can comprise cleaving the cleavable element with a cleavage agent (see e.g., FIG. 1B), thereby releasing the first sequence element 5' of the guide sequence (see, e.g., FIG. 1C). For example, the cleavable element can be a photolabile linker, and the photolabile linker can be cleaved when exposed to light. Cleaving the cleavable linker can result in a CRISPR complex with higher target-specific cleavage activity than the CRISPR complex before the cleavage.

B. CRISPR OFF

Provided herein are CRISPR OFF polynucleotides that can be complexed with CRISPR effector proteins to form CRISPR OFF complexes. A CRISPR OFF polynucleotide can comprise (i) a sequence (e.g., tracrRNA sequence) configured to bind a CRISPR effector protein and (ii) a cleavable linker. In some cases, the CRISPR OFF polynucleotide further comprises a guide sequence configured to anneal to a target sequence in a target nucleic acid molecule. The cleavable linker can be a non-naturally occurring cleavable linker. If the CRISPR OFF polynucleotide comprises the guide sequence, the cleavable linker can be positioned 3' of the 5' most base in the guide sequence. The cleavable linker can be positioned within the sequence configured to bind the CRISPR effector protein (e.g., a tracrRNA sequence). In some cases, a base immediately 3' and/or immediately 5' of a cleavable linker is not annealed to another base in the CRISPR OFF polynucleotide. The cleavable linker can be a photolabile linker. The cleavable linker can be susceptible to cleavage by light, small molecule, or one or more cellular processes.

The off-target editing activity of a CRISPR effector protein complexed with a CRISPR OFF polynucleotide can be less than the off-target editing activity of a CRISPR effector protein complexed with a non-CRISPR-OFF polynucleotide, e.g., an sgRNA without one or more cleavable linkers. The sgRNA without one or more cleavable linkers can be modified with only with 2'-O-methyl analogs and 3' phosphorothioate internucleotide linkages at the first three 5' and 3' terminal RNA nucleotides. The off-target editing activity of a CRISPR effector protein complexed with a CRISPR OFF polynucleotide when not cleaved (e.g., without exposure to light when the CRISPR OFF polynucleotide has a photocleavable linker) can be statistically lower, with a p-value≤0.05, ≤0.01, ≤0.005, ≤0.001, ≤0.0005, or ≤0.0001, than a CRISPR effector protein complexed with a non-CRISPR-OFF polynucleotide. The off-target editing activity (e.g., as measured as described herein) can be reduced by a factor of: about 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, or at least 1.1, 1.5, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60; or at most 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, or 60. In some cases, the reduction occurs in the absence of exposure to a cleavage agent, e.g., UV light or visible light; in some cases, the reduction occurs after exposure to a cleavage agent. For example, complexes comprising a CRISPR effector protein complexed with a CRISPR OFF polynucleotide with a cleavable linker at positions 57 and/or 74 can have a lower off-target editing efficiency than a CRISPR effector protein complexed with an sgRNA without a cleavable linker. Complexes comprising a CRISPR effector protein complexed with a CRISPR OFF polynucleotide when not cleaved (e.g., without exposure to light when the CRISPR OFF polynucleotide has a photocleavable linker) can have an on-target editing efficiency that is the same or is within 1%, 2%, 3%, 4%, or 5% of that of a CRISPR effector protein complexed with a non-CRISPR OFF polynucleotide, e.g., an sgRNA without a cleavable linker.

Complexes comprising a CRISPR effector protein complexed to the CRISPR OFF polynucleotide can be assembled. Provided herein are methods for the tunable targeting of a CRISPR complex to a target DNA. The methods can comprise cleaving the cleavable linker. Cleavage of the cleavable linker can result in a CRISPR complex with a lower target-specific cleavage activity than before the cleavage. In some cases, cleavage of the cleavable linker can cause the fragments of the CRISPR OFF polynucleotide generated by the cleaving to dissociate from the CRISPR effector protein. In some cases, cleavage of the cleavable linker renders a CRISPR complex inactive.

C. CRISPR ON/OFF

Provided herein are CRISPR "ON/OFF" polynucleotides that can be complexed with CRISPR effector proteins to form CRISPR "ON/OFF" complexes. A CRISPR ON/OFF polynucleotide can comprise a guide sequence configured to anneal to a target sequence in a target nucleic acid molecule, a sequence (e.g., a tracrRNA sequence) configured to bind to a CRISPR effector protein, and (a) a first element configured to be subjected to a first specific modification that generates a first modified polynucleotide that, when complexed with a CRISPR effector protein, forms a first CRISPR complex with higher target-specific cleavage activity than a CRISPR complex comprising the polynucleotide that has not had been subjected to the first specific modification, and (b) a second element configured to be subjected to a second specific modification to generate a second modified polynucleotide that, when complexed with CRISPR effector protein, forms a second CRISPR complex with a lower target-specific cleavage activity than the first CRISPR complex. A CRISPR ON/OFF polynucleotide can comprise features of CRISPR ON polynucleotides and CRISPR OFF polynucleotides described herein.

Complexes comprising a CRISPR effector protein complexed to the CRISPR ON/OFF polynucleotide can be assembled. Provided herein are methods for the tunable targeting of a CRISPR complex to a target DNA. The methods can comprise subjecting the first element of the CRISPR ON/OFF polynucleotide to a first specific modification, thereby generating the first modified polynucleotide that, when complexed with the CRISPR effector protein, forms the first CRISPR complex with higher target-specific cleavage activity than the CRISPR complex comprising the polynucleotide that has not had been subjected to the first specific modification. The methods can further comprise subjecting the second element to the second specific modification after the subjecting the first element to the first modification, thereby forming the second modified polynucleotide that, when complexed with CRISPR effector protein, forms a second CRISPR complex with a lower target-specific cleavage activity than the first CRISPR complex. In some cases, the second modification can cause the CRISPR polynucleotide to fragment and/or dissociate from the CRISPR effector protein.

Further embodiments are described herein.

II. CRISPR Overview

A. CRISPR Complex Overview

A CRISPR complex can be a non-naturally occurring or engineered DNA or RNA-targeting system comprising one or more DNA or RNA-targeting CRISPR effector proteins and one or more CRISPR polynucleotides. The one or more CRISPR polynucleotides can be any CRISPR polynucleotide provided herein. The target sequence can be a sequence to which a guide sequence of a CRISPR polynucleotide is designed to have complementarity, and "complementarity" can refer to the ability of a nucleic acid to form hydrogen bond(s) with another nucleic acid sequence by either traditional Watson-Crick base-pairing or other non-traditional types of base-paring. The CRISPR complex can interact with two nucleic acid strands that form a duplex structure, three or more strands forming a multi stranded complex, a single self-hybridizing strand, or any combination of these.

Upon binding of the CRISPR complex to the target sequence, sequences associated with the target sequence can be modified by the CRISPR effector protein. The CRISPR effector protein can be part of a fusion protein that can comprise one or more heterologous protein domains (e.g. about or more than about 1, 2, 3, 4, 5, 6, 7, 8, 9, 10, or more domains in addition to the CRISPR effector protein). In some examples, the functionality of the CRISPR complex is conferred by the heterologous protein domains.

In some cases, one or more elements of a CRISPR system can be derived from a type I, type II, or type III CRISPR system. In the CRISPR type II system, the CRISPR polynucleotide (e.g., guide RNA) can interact with Cas endonuclease and direct the nuclease activity of the Cas enzyme to a target region. The target region can comprise a "protospacer" and a "protospacer adjacent motif" (PAM), and both domains can be used for a Cas enzyme mediated activity (e.g., cleavage). The guide sequence can pair with (or hybridize) the opposite strand of the protospacer (binding site) to direct the Cas enzyme to the target region. The PAM site can refer to a short sequence recognized by the Cas enzyme and, in some cases, required for the Cas enzyme activity. The sequence and number of nucleotides for the PAM site can differ depending on the type of the Cas enzyme.

B. CRISPR Polynucleotides Overview

The CRISPR polynucleotides, e.g., CRISPR ON, CRISPR OFF, CRISPR ON/OFF, described herein can comprise a guide sequence. The guide sequence can be within a CRISPR RNA (e.g., tracrRNA, crRNA). The guide sequence can comprise sufficient complementarity with a target nucleic acid sequence to hybridize with the target nucleic acid sequence. The degree of complementarity, when optimally aligned using a suitable alignment algorithm, can be about or more than about 50%, 60%, 75%, 80%, 85%, 90%, 95%, 97.5%, or 99%. The degree of complementarity can be 100%. In some cases, the guide sequence e.g., can be about 5, 6, 7, 8, 9, 11, 12, 13, 14, 15, 16, 17, 18, 19, 20, 25, 30, 40, 50, or more nucleotides in length. The guide sequence can be about 5 to about 40 nucleotides in length. The guide sequence can be designed in a way that reduces the likelihood that the guide sequence base pairs to itself or base pairs with another portion of the CRISPR polynucleotide. About or less than about 75%, 50%, 40%, 30%, 25%, 20%, 15%, 10%, 5%, 1%, or fewer of the nucleotides of the guide sequence can form a base-pair with another portion of the guide sequence or another portion of the CRISPR polynucleotide when the CRISPR polynucleotide is optimally folded.

In some cases, a single CRISPR polynucleotide binds a single CRISPR effector protein. The single CRISPR polynucleotide can comprise a guide sequence and sequence that binds the CRISPR effector protein. The sequence that can bind the CRISPR effector protein can be a trans-activating RNA (tracrRNA). When a single CRISPR polynucleotide comprises a guide sequence and a tracrRNA, the single CRISPR polynucleotide can be referred to as a single guide RNA (or sgRNA).

In some cases, two CRISPR polynucleotides bind a single CRISPR effector protein. A first CRISPR polynucleotide can comprise a guide sequence, and a second CRISPR polynucleotide can comprise a tracrRNA and lack a guide sequence.

In some cases, the first CRISPR polynucleotide comprises a guide sequence and a first part of the sequence (which can be referred to as a tracr mate sequence) that forms the crRNA, and the second CRISPR polynucleotide comprises a second part of the sequence that forms the tracrRNA (which can be referred to as the tracr sequence). In some cases, the tracr sequence (or tracrRNA) hybridizes to the 'tracr mate' sequence within the crRNA thereby forming a double-stranded RNA duplex protein binding segment recognized by the CRISPR effector protein. A CRISPR polynucleotide comprising a guide sequence (also known as spacer sequence) but lacking sequence that can bind to the CRISPR effector protein can be referred to as a guide RNA (or gRNA). A CRISPR polynucleotide comprising a guide sequence and only part of a sequence that can bind to the CRISPR effector protein (e.g., a tracr mate sequence) (and lacks a tracr sequence) can also be referred to as a guide RNA (or gRNA) or crRNA.

A tracrRNA can hybridize to the 'tracr mate' sequence within the crRNA thereby forming a double-stranded RNA duplex protein binding segment recognized by the CRISPR effector protein. In some examples, the hybridization between the two produces a secondary structure, such as a hairpin. In some cases, the CRISPR polynucleotide sequence can comprise three, four, five, or more hairpins. The tracrRNA can comprise, or consist of, one or more hairpins and can be at least 10, 20, 30, 40, 50, 60, 70, 80, 90, or 100 nucleotides in length.

In some cases, a first CRISPR polynucleotide can be crRNA and a second CRISPR polynucleotide can be tracrRNA and the first CRISPR polynucleotide and second CRISPR polynucleotide can be two separate RNA molecules. In some cases, a single CRISPR polynucleotide can comprise (1) a guide sequence (or crRNA comprising a guide sequence) capable of hybridizing to a target sequence (e.g., a genomic target locus in a eukaryotic cell) and (2) a tracrRNA. In some cases, the first CRISPR polynucleotide can comprise (1) a guide sequence (or crRNA comprising a guide sequence) (e.g., capable of hybridizing to a target sequence in the eukaryotic cell); and (2) a tracr mate sequence (also known as direct repeat sequence) but lacking a tracrRNA sequence. The CRISPR effector protein can associate with a guide sequence capable of hybridizing to a target sequence and a tracr mate sequence (direct repeat sequence), without the requirement for a tracrRNA.

When the tracr and tracr mate sequences are in a single CRISPR polynucleotide, the tracr and tracr mate sequences can be covalently linked. The tracr and tracr mate sequence can be linked through a phosphodiester bond. The tracr and tracr mate can be covalently linked via a non-nucleotide loop comprising a moiety such as a spacer, attachment, bioconjugate, chromophore, reporter group, dye labeled RNA, or non-naturally occurring nucleotide analogue. The spacer can be a polyether (e.g., polyethylene glycol, polyalcohol, polypropylene glycol or mixtures of ethylene and propylene glycol), polyamine group (e.g., spennine, spermidine, or a polymeric derivative thereof), polyester (e.g., poly(ethyl acrylate)), polyphosphodiester, alkylene, and combinations thereof. The attachment can be a fluorescent label. The bioconjugate can be, e.g., a peptide, a glycoside, a lipid, a cholesterol, a phospholipid, a diacyl glycerol, a dialkyl glycerol, a fatty acid, a hydrocarbon, an enzyme substrate, a steroid, biotin, digoxigenin, a carbohydrate, or a polysaccharide. The chromophore, reporter group, or dye-labeled RNA can be a fluorescent dye, e.g., fluorescein or rhodamine, a chemiluminescent, an electrochemiluminescent, or a bioluminescent marker compound.

In some cases, e.g., to increase the effectiveness of a CRISPR polynucleotide, e.g., gRNA or sgRNA, other secondary structures may be added to the CRISPR polynucleotide, e.g., gRNA or sgRNA to enhance the stability of the CRISPR polynucleotide. In some cases, the increased stability can improve nucleic acid editing.

In some cases, e.g., to increase the effectiveness of a CRISPR polynucleotide, e.g., gRNA or sgRNA, one or more modifications can be added to the CRISPR polynucleotide, e.g., gRNA or sgRNA that lower the off-target editing activity of the CRISPR polynucleotide in complex with a CRISPR enzyme. The one or more modifications can be at various locations, including at a sugar moiety, a phosphodiester linkage, and/or a base. For example, the CRISPR polynucleotide can comprise a backbone that comprises phosphoramide, phosphorothioate, phosphorodithioate, boranophosphate linkage, O-methylphosphoramidite linkages, and/or peptide nucleic acids. The one or more can comprise a 2'fluoro-arabino nucleic acid, tricycle-DNA (tc-DNA), peptide nucleic acid, cyclohexene nucleic acid (CeNA), locked nucleic acid (LNA), a locked nucleic acid (LNA) nucleotide comprising a methylene bridge between the 2' and 4' carbons of the ribose ring, bridged nucleic acids (BNA), ethylene-bridged nucleic acid (ENA), a phosphodiamidate morpholino, (3-(4,4'-Dimethoxytrityl)-1-(2-nitrophenyl)-propan-1-yl-[(2-cyanoethyl)-(N,N-diisopropyl)]-phosphoramidite), or a combination thereof.

The CRISPR polynucleotide, e.g., CRISPR ON, CRISPR OFF and, CRISPR ON/OFF, can comprise RNA, DNA-RNA hybrids, or derivatives thereof. The CRISPR polynucleotide can comprise nucleosides, which can comprise a base covalently attached to a sugar moiety, e.g., ribose or deoxyribose. The nucleosides can be ribonucleosides or deoxyribonucleosides. The nucleosides can comprise bases linked to amino acids or amino acid analogs, which can comprise free carboxyl groups, free amino groups, or protecting groups. The protecting groups can be a protecting group described, e.g., in P. G. M. Wuts and T. W. Greene, "Protective Groups in Organic Synthesis", 2nd Ed., Wiley-Interscience, New York, 1999. The CRISPR polynucleotides can comprise a canonical cyclic nucleotide, e.g., cAMP, cGMP, cCMP, cUMP, cIMP, cXMP, or cTMP. A canonical nucleotide base can be adenine, cytosine, uracil, guanine, or thymine. The nucleotide can comprise a nucleoside attached to a phosphate group or a phosphate analog.

The CRISPR polynucleotide can exist as one or more molecules of RNA, or DNA (e.g., in one or more vectors encoding said one or more molecules of RNA or protein). The CRISPR polynucleotides can be deoxyribonucleic acids (DNA), ribonucleic acids (RNA) and polymers thereof in either single-, double- or multi-stranded form. The CRISPR polynucleotide can comprise single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases.

The CRISPR polynucleotide (e.g., sgRNA) disclosed herein can comprise one or more modifications at various locations, including at a sugar moiety, a phosphodiester linkage, and/or a base. For example, the CRISPR polynucleotide can comprise a backbone that comprises phosphoramide, phosphorothioate, phosphorodithioate, boranophosphate linkage, O-methylphosphoramidite linkages, and/or peptide nucleic acids. The CRISPR polynucleotide can comprise a 2'fluoro-arabino nucleic acid, tricycle-DNA (tc-DNA), peptide nucleic acid, cyclohexene nucleic acid (CeNA), locked nucleic acid (LNA), a locked nucleic acid (LNA) nucleotide comprising a methylene bridge between the 2' and 4' carbons of the ribose ring, bridged nucleic acids (BNA), ethylene-bridged nucleic acid (ENA), a phosphodiamidate morpholino, or a combination thereof.

The CRISPR polynucleotide (e.g., sgRNA) can comprise one or more non-naturally occurring nucleotides or nucleotide analogs, e.g., a nucleotide with phosphorothioate linkage, boranophosphate linkage, a locked nucleic acid (LNA) nucleotide comprising a methylene bridge between the 2' and 4' carbons of the ribose ring or bridged nucleic acids (BNA). The non-naturally occurring nucleotides or nucleotide analogs can be 2'-O-methyl analogs, 2'-deoxy analogs, 2-thiouridine analogs, N6-methyladenosine analogs, or 2'-fluoro analogs.

In some cases, the polynucleotide can comprise modified nucleotides and/or modified internucleotide linkages at the first 1, 2, 3, 4, 5, 6, 7, 8, 9, 10, 11 or 12 nucleotides at the 5' terminus. In some cases, the polynucleotide can comprise modified nucleotides and/or modified internucleotide linkages at 1, 2, 3, 4, 5, 6, 7, 8, 9, 10, 11 or 12 nucleotides at the 3' terminus. In some cases, the polynucleotide can comprise modified nucleotides and/or modified internucleotide linkages at the first 1, 2, 3, 4, 5, 6, 7, 8, 9, 10, 11 or 12 nucleotides at the 5' terminus or 1, 2, 3, 4, 5, 6, 7, 8, 9, 10, 11 or 12 nucleotides at the 3' terminus. In some cases, the polynucleotide can comprise modified nucleotides and/or modified internucleotide linkages at the first 1, 2, 3, 4, 5, 6, 7, 8, 9, 10, 11 or 12 nucleotides at the 5' terminus and the first 1, 2, 3, 4, 6, 7, 8, 9, 10, 11 or 12 nucleotides at the 3' terminus. The modifications can be 2'-O-methyl analogs and/or 3' phosphorothioate internucleotide linkages.

The CRISPR polynucleotide can comprise one or more modified bases. The one or more modified bases can be 2-aminopurine, 5-bromo-uridine, pseudouridine (Ψ), Nˆmethylpseudouridine (mel P), 5-methoxyuridine (5moU), inosine, or 7-methylguanosine.

The CRISPR polynucleotide can comprise a sugar moiety. The sugar moieties can be natural, unmodified sugar, e.g., monosaccharide (e.g., pentose, e.g., ribose, deoxyribose), modified sugars, or sugar analogs. In some cases, the sugar moiety can have one or more hydroxyl groups replaced with a halogen, a heteroatom, an aliphatic group, or the one or more hydroxyl groups can be functionalized as an ether, an amine, a thiol, or the like.

The CRISPR polynucleotide can comprise one or more modifications at a 2' position of a ribose. The one or more modifications at the 2' position of the ribose can be introduced, e.g., to reduce immunostimulation in a cellular context. The 2' moiety can be H, OR, R, halo, SH, SR, H2, HR, R2 or ON, wherein R is C1-C6 alkyl, alkenyl or alkynyl and halo is F, CI, Br or I. Examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-0-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof. The sugar-modified ribonucleotides can have the 2' OH group replaced by a H, alkoxy (or OR), R or alkyl, halogen, SH, SR, amino (such as NH2, NHR, NR2), or CN group, wherein R is lower alkyl, alkenyl, or alkynyl. The modification at the 2' position can be a methyl group.

The CRISPR polynucleotide, e.g., CRISPR ON polynucleotide, CRISPR OFF polynucleotide, or CRISPR ON/OFF polynucleotide, can comprise one or more nucleobase-modified ribonucleotides. The one or more modified ribonucleotides can contain a non-naturally occurring base (instead of a naturally occurring base), such as uridines or cytidines modified at the 5'-position, e.g., 5' (2-amino)propyl uridine or 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine.

The nucleobase-modified ribonucleotides can be m5C (5-methylcytidine), m5U (5-methyluridine), m6A (N6-methyladenosine), s2U (2-thiouridine), Um (2'-0-methyluridine), mlA (1-methyl adenosine), m2A (2-methyladenosine), Am (2-1-O-methyladenosine), ms2m6A (2-methylthio-N6-methyladenosine), i6A (N6-isopentenyl adenosine), ms2i6A (2-methylthio-N6isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A(N6.-hydroxynorvalylcarbamoyl adenosine), ms2hn6A (2-methylthio-N6-hydroxynorvalyl carbamoyladenosine), Ar(p) (2'-0-ribosyladenosine(phosphate)), I (inosine), mi 1 (1-methylinosine), m'lm (1,2'-0-dimethylinosine), m3C (3-methylcytidine), Cm (2T-0-methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-0-methylguanosine), m22G (N2,N2-dimethylguanosine), m2Gm (N2,2'-0-dimethylguanosine), m22Gm (N2,N2,2'-0-trimethylguanosine), Gr(p) (2'-0-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-0-dimethyluridine), s4U (4-thiouridine), m5s2U (5-methyl-2-thiouridine), s2Um (2-thio-2'-0-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5s2U (5-methoxycarbonylmethyl-2-thiouridine), nm5s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-0-methyluridine), cmnm5U (5-carboxymethylaminomethyluridine), cnmm5Um (5-carboxymethylaminomethyl-2-L-Omethyluridine), cmnm5s2U (5-carboxymethylaminomethyl-2-thiouridine), m62A (N6,N6-dimethyladenosine), Tm (2'-0-methylinosine), m4C (N4-methylcytidine), m4Cm (N4,2-0-dimethylcytidine), hm5C (5-hydroxymethylcytidine), m3U (3-methyluridine), cm5U (5-carboxymethyluridine), m6Am (N6,T-0-dimethyladenosine), rn62Am (N6,N6,0-2-trimethyladenosine), m2'7G (N2,7-dimethylguanosine), m2'2'7G (N2,N2,7-trimethylguanosine), m3Um (3,2T-0-dimethyluridine), m5D (5-methyldihydrouridine), f5Cm (5-formyl-2'-0-methylcytidine), mlGm (1,2'-0-dimethylguanosine), m'Am (1,2-0-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxy cytosine, 5-(Ci-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

The nucleobase-modified ribonucleotide can be Aminopurine, 2,6-Diaminopume (2-Amino-dA), 5-Bromo dU, deoxyuridine, Inverted dT, Inverted Dideoxy-T, dideoxy-C, 5-Methyl dC, Super (T), Super (G), 5-Nitroindole, 2'-O-Methyl RNA Bases, Hydroxymetyl dC, Iso dG, Iso dC, Fluoro C, Fluoro U, Fluoro A, Fluoro G, 2-MethoxyEthoxy MeC, 2-MethoxyEthoxy G, or 2-MethoxyEthoxyT.

In some cases, one or more nucleotides of the CRISPR polynucleotide can be modified to improve the CRISPR polynucleotide's resistance to nucleases, serum stability, target specificity, blood system circulation, tissue distribution, tissue penetration, cellular uptake, potency, and/or cell-permeability. For example, certain CRISPR polynucleotide (e.g., sgRNA) modifications can increase nuclease stability, and/or lower interferon induction, without significantly affecting activity of the CRISPR polynucleotide (e.g., sgRNA). The modified CRISPR polynucleotide can have improved stability in serum and/or cerebral spinal fluid compared to an unmodified CRISPR polynucleotide having the same sequence.

In some cases, the 3' and 5' termini of a CRISPR polynucleotide can be substantially protected from nucleases e.g., by modifying the 3' or 5' linkages (e.g., U.S. Pat. No. 5,849,902 and WO 98/13526). For example, CRISPR polynucleotides can be made resistant by the inclusion of one or more "blocking groups." The one or more "blocking groups" can be a substituent (e.g., other than OH groups) that can be attached to polynucleotides or nucleomonomers, either as protecting groups or coupling groups for synthesis (e.g., FITC, propyl (CH2-CH2-CH3), glycol (—O—CH2-CH2-O—) phosphate (PO3 2-), hydrogen phosphonate, or phosphoramidite). The one or more blocking groups can be one or more "end blocking groups" or one or more "exonuclease blocking groups" that can protect the 5' and 3' termini of the CRISPR polynucleotide, including modified nucleotides and non-nucleotide exonuclease resistant structures.

The one or more end-blocking groups can be a cap structure (e.g., a 7-methylguanosine cap), inverted nucleomonomer, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. For example, the 3'-hydroxyl can be esterified to a nucleotide through a 3'→3' internucleotide linkage. For example, the alkyloxy radical can be methoxy, ethoxy, or isopropoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage.

The CRISPR polynucleotide can comprise one or more labels or tags. The one or more "labels" or "tags" can be a molecule that can be attached to another molecule, e.g., a CRISPR polynucleotide or a segment thereof, to provide a means by which the other molecule can be readily detected. The CRISPR polynucleotide can comprise a label, which can be fluorescent, luminescent, radioactive, enzymatically active, etc. The one or more labels can include fluorochromes, e.g. fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. 32P, 35S, 3H; etc. The one or more labels can be a two-stage system, where the CRISPR polynucleotide is conjugated to biotin, haptens, etc. having a high affinity binding partner, e.g. avidin, specific antibodies, etc., where the binding partner is conjugated to a detectable label.

C. CRISPR Effector Protein Overview

The CRISPR effector protein can be a Cas protein. The term "Cas" can refer to a wild type Cas protein, a fragment thereof, or a mutant or variant thereof.

The CRISPR effector protein can be any of the enzymes from the CRISPR Cas, CRISPR-CasX or CRISPR-CasY bacterial systems. A Cas protein can comprise a protein of or derived from a CRISPR/Cas type I, type II, or type III system, which has an RNA-guided polynucleotide-binding or nuclease activity. The Cas protein can be Cas3, Cas4, Cas5, Cas5e (or CasD), Cas6, Cas6e, Cas6f, Cas7, Cas8a1, Cas8a2, Cas8b, Cas8c, Cas9 (also known as Csnl and Csxl2), Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, homologues thereof, or modified versions thereof. In some cases, a Cas protein can comprise a protein of or derived from a CRISPR/Cas type V or type VI system, such as Cpf1, C2c1, C2c2, homologues thereof, and modified versions.

The CRISPR effector protein comprise sequence of a CRISPR effector protein found in any of the following bacterial species, or sequence derived from a CRISPR effector protein found in any of the following species: *Streptococcus pyogenes, Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, candidatus punicei spirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *multocida, Sutterella wadsworthensis*, proteobacterium, *Legionella pneumophila, Parasutterella excrementihominis, Wolinella succinogenes*, or *Francisella novicida*.

In some instances, nucleic acid sequence encoding CRISPR effector protein can be optimized for expression in a eukaryote e.g., humans (i.e. being optimized for expression in humans), or for another eukaryote, animal or mammal as herein discussed. In general, codon optimization can refer to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence.

In some examples, modifications can be introduced into the CRISPR effector protein to enhance stability, tunability, and/or lower interferon induction etc.

III. Polynucleotide Leader Sequence in CRISPR ON Polynucleotides and CRISPR ON/OFF Polynucleotides A CRISPR ON polynucleotide or CRISPR ON/OFF polynucleotide can comprise a first sequence element 5' of the guide sequence. The first sequence element 5' of the guide sequence can be referred to as a polynucleotide leader sequence. A CRISPR complex comprising a CRISPR polynucleotide with a polynucleotide leader sequence and a CRISPR effector protein can have a lower activity than a CRISPR complex comprising a CRISPR polynucleotide without the polynucleotide leader sequence. Removal of the polynucleotide leader sequence can result in a CRISPR complex with an increased activity (CRISPR ON).

A. Length of the Polynucleotide Leader Sequence

The polynucleotide leader sequence can range from about 1 nucleotide to about 50 nucleotides, e.g., about 5 nucleotides to about 30 nucleotides, about 10 nucleotides to about 20 nucleotides, about 15 nucleotides, or at least 4 nucleotides, 3 nucleotides to about 15 nucleotides, e.g., about 5 nucleotides to about 15 nucleotides, about 3 nucleotides to about 10 nucleotides, about 3 to about 15 nucleotides, or about 3 nucleotides to about 12 nucleotides, about 4 nucleotides to about 13 nucleotides, about 3 nucleotides to about 18 nucleotides, about 4 nucleotides to about 19 nucleotides, from 4 nucleotides to about 30 nucleotides, from 4 nucleotides to about 25 nucleotides, from 5 nucleotides to about 12 nucleotides, from 5 nucleotides to about at least 4 nucleotides, or 30 or fewer nucleotides in length.

B. Composition of the Polynucleotide Leader Sequence

The polynucleotide leader sequence can comprise ribonucleotides and/or deoxyribonucleotides. The polynucleotide leader sequence can comprise non-canonical nucleotides or nucleotide analogues. The polynucleotide leader sequence can comprise any nucleotide or modified nucleotide or internucleotide linkage described herein. In some cases, the polynucleotide leader sequence can comprise any linker described herein.

C. Secondary Structure in the Polynucleotide Leader Sequence

The polynucleotide leader sequence can form, or be designed to form, secondary structure. The secondary structure can be, e.g., a stem loop structure. The stem of the stem loop can comprise at least about 3 bp comprising complementary X and Y sequences (where X represents the sequence of one strand of the stem and Y represents the sequence of the other strand of the stem). The stem can comprise at least (or at most) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 base pairs. The stem can comprise a double stranded domain ranging from 1-20 bp, or from 2-5 bp, 2-9 bp, 3-10 bp, 4-9 bp, 5-10 bp, 5-20 bp, 6-20 bp, 7-20 bp, 8-20 bp etc. In some cases, the two strands of the stem can be covalently cross-linked.

The stem loop can comprise a single-stranded loop. The single-stranded loop can range from 1-50 bases, e.g., 3-5 bases, 3-7 bases, 4-10 bases, 5-20 bases, 6-25 bases, 3-25 bases, 3-30 bases, 4-30 bases, or 4-50 bases.

The 5' most base of the stem loop, or of the polynucleotide leader sequence, can anneal to a base in the polynucleotide leader sequence immediately 5' of the guide sequence. In some cases, the 5' most base of the polynucleotide leader sequence can anneal to a base 1-20 bases 3' of the 5' most base of the guide sequence, e.g., 2 bases, 3 bases, 4 bases, 5 bases, 6 bases, 7 bases, 8 bases, 9 bases, 10 bases, 11 bases, 12 bases, 15 bases, or 20 bases 3' of the 5' most base of the guide sequence. In some cases, the polynucleotide leader sequence does not comprise a base that base pairs to a base in the guide sequence.

The polynucleotide leader sequence can form a hairpin loop or stem-loop structure comprising one or more bulges (regions of single stranded sequence; these regions can correspond to positions comprising less than 100% sequence base-pairing in the secondary structure). The number, length, and/or position of the one or more bulges can vary and can affect the overall stability of the stem-loop structure. The polynucleotide leader sequence can comprise 2, 3, 4, 5 or more bulges when optimally folded.

In some cases, the polynucleotide leader sequence can comprise non-polynucleotide moieties. The non-nucleotide moieties in the polynucleotide leader sequence can be biotin, antibodies, peptides, affinity, reporter or protein moieties (such as NHS esters or isothiocyanates), digoxigenin, enzymes such as alkaline phosphatase etc.

In some cases, the polynucleotide leader sequence lacks secondary structure. The polynucleotide leader sequence can comprise or consist of a single stranded contiguous stretch of nucleotides.

The melting temperature of a stem loop formed by the polynucleotide leader sequence can be about 25° C. to about 60° C., or about 30° C. to about 50° C., or about 40° C. to about 50° C.

D. Reduction in Activity Owing to the Polynucleotide Leader Sequence

A CRISPR complex comprising a CRISPR polynucleotide with a polynucleotide leader sequence and a CRISPR effector protein (e.g., Cas9) can have a lower activity than a CRISPR complex comprising a CRISPR polynucleotide without the polynucleotide leader sequence. In some cases, the activity is at least (or at most) 0.1 fold, 0.25 fold, 0.5 fold, 0.75 fold, 1 fold, 2 fold, 5 fold, 10 fold, 50 fold, 100 fold, or 1000 fold lower. In some cases, a CRISPR complex comprising a CRISPR polynucleotide with a polynucleotide leader sequence and a CRISPR effector protein has no activity. The activity can be, e.g., enzymatic activity or transcriptional activation activity. For example, when the CRISPR effector protein is a catalytically active Cas protein, the CRISPR complex can be unable to cleave target nucleic acid. In another example, when the CRISPR effector protein is a catalytically dead Cas protein fused to a transcription activation domain, the CRISPR complex can be unable to activate transcription of a target gene.

E. Removing the Polynucleotide Leader Sequence

The CRISPR polynucleotide can comprise one or more cleavable elements to permit release of the polynucleotide leader sequence. The one or more cleavable elements can be between the polynucleotide leader sequence and the guide sequence. In some cases, the one or more cleavable elements are within the polynucleotide leader sequence. In some cases, at least one cleavable element is within the polynucleotide leader sequence and at least one cleavable element is between the polynucleotide leader sequence and the guide sequence. In some cases, the one or more cleavable elements are positioned 5' of the guide sequence. The one or more cleavable elements can be at least, or at most, 2, 3, 4, 5, 6, 7, 8, 9 or 10 cleavable elements. In some cases, the one or more cleavable elements are positioned such that following cleavage, part of the polynucleotide leader sequence (e.g., 1 base, 2 bases, 5 bases, or 10 bases) remains covalently linked to the guide sequence. In some cases, the one or more cleavable elements are positioned such that following cleavage, none of the polynucleotide leader sequence remains covalently attached to the guide sequence.

The one or more cleavable elements can be any cleavable element described herein. The one or more cleavable elements can be the same type of cleavable element or different types of cleavable elements.

The CRISPR polynucleotide can be cleaved at the one or more cleavable elements while the CRISPR polynucleotide is not bound to a CRISPR effector protein. The CRISPR polynucleotide can be cleaved at the one or more cleavable elements while the CRISPR polynucleotide is complexed with a CRISPR effector protein. The CRISPR polynucleotide can be cleaved at the one or more cleavable elements while the CRISPR polynucleotide is complexed with a CRISPR effector protein and bound to a target sequence. In some cases, the polynucleotide leader sequence prevents the CRISPR polynucleotide from complexing with a CRISPR effector protein or reduces the ability of the CRISPR polynucleotide to bind the CRISPR effector protein relative to a CRISPR polynucleotide that lacks the polynucleotide leader sequence; cleavage of the polynucleotide leader sequence from the CRISPR polynucleotide can increase the ability of the CRISPR polynucleotide to bind a CRISPR effector protein.

The CRISPR polynucleotide can be cleaved at the one or more cleavable elements in vitro. The CRISPR polynucleotide can be cleaved at the one or more cleavable elements while in a cell or organism, e.g., mouse, rabbit, goat, primate, e.g., chimpanzee, gorilla, or human.

The timing of the cleaving of the CRISPR polynucleotide at the one or more cleavable elements can vary. For example, the one or more cleavable elements can be cleaved immediately after the CRISPR polynucleotide is introduced into a cell or organism, or at least (or at most) 0.25, 0.5, 0.75, 1, 2, 3, 4, 5, 6, 7, 8, 9, 10, 11, 12, 13, 14, 15, 16, 17, 18, 19, 20, 21, 22, 23, 24, 48, 72, or 96 hours after introduction into a cell or organism.

A CRISPR polynucleotide can be exposed to a cleavage agent once. The CRISPR polynucleotide can be subjected to a cleavage agent more than once, e.g., 2 times, 3 times, 5 times, or 10 times. The CRISPR polynucleotide can be exposed to more than one type of cleavage agent, e.g., at least (or at most) 2, 3, 4, 5, 6, 7, 8, 9, or 10 cleavage agents.

A CRISPR polynucleotide can be exposed to a cleavage agent for varying durations. For example, a CRISPR polynucleotide can be exposed to a cleavage agent for 0.1 min, 0.5 min, 1 min, 2 min, 3 min, 4 min, 5 min, 10 min, 30 min, 60 min, 2 hr, 4 hr, 6 hr, 12 hr, 24 hr, 48 hr, 72 hr, or 96 hr.

In some cases, a sample comprises a plurality of CRISPR polynucleotides, and a cleavage agent can be used to cleave a certain percentage of the CRISPR polynucleotides. For example, a cleaving agent can be used to cleave at least (or at most) 5%, 10%, 15%, 20%, 25%, 30%, 35%, 40%, 45%, 50%, 55%, 60%, 65%, 70%, 75%, 80%, 85%, 90%, 95%, or 99% of the CRISPR polynucleotides in the sample. A dose of a cleaving agent can be used to cleave 100% of the CRISPR polynucleotides in the sample. The amount of cleavage can occur over at least (or at most) 1 min, 5 min, 10 min, 15 min, 30 min, 45 min, 1 hr, 2 hr, 6 hr, 12 hr, 24 hr, 48 hr, 72 hr, or 96 hr.

The release of the polynucleotide leader sequence can result in an increase in activity of a CRISPR effector protein (e.g., CRISPR enzyme, e.g., Cas9) bound to the CRISPR polynucleotide. In some cases, in a sample, release of the polynucleotide leader sequence results in at least a 0.1-fold, 0.25 fold, 0.5 fold, 0.75 fold, 1 fold, 2 fold, 5 fold, 10 fold, 50 fold, 100 fold, or 1000 fold increase in activity.

F. Other Features

The CRISPR polynucleotide comprising a polynucleotide leader sequence can comprise a second set of one or more elements that can be subjected to a specific modification to generate a modified CRISPR polynucleotide that, when complexed with CRISPR effector protein, forms a second CRISPR complex with a lower target-specific cleavage activity. The second set of one or more elements can be a second set of one or more cleavable elements. For example, a CRISPR polynucleotide can comprise a polynucleotide leader sequence and a first set of one or more cleavable elements configured to permit release of the polynucleotide leader sequence and a second set of one or more cleavable elements configured to permit cleavage of the remaining CRISPR polynucleotide; this polynucleotide can be referred to as a CRISPR ON/OFF polynucleotide.

IV. CRISPR OFF and CRISPR ON/OFF Polynucleotides

The CRISPR OFF polynucleotide or CRISPR ON/OFF polynucleotide can comprise an element configured to be subjected to a specific modification to generate a modified CRISPR polynucleotide (e.g., sgRNA) that, when complexed with CRISPR effector protein (e.g., Cas9), forms a second CRISPR complex with a lower target-specific cleavage activity than the first CRISPR complex. The element can be one or more cleavable elements, and the specific modification can be cleavage of the one or more cleavable elements.

A. Position of the One or More Cleavable Elements

The one or more cleavable elements can be positioned 3' of the 5'-most base (or nucleotide) in the guide sequence or 5' of the 3' most base (or nucleotide) in the guide sequence. The one or more cleavable elements can be positioned about 1-30 bases 3' of the 5' end of the crRNA or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. The one or more cleavable elements can be positioned about 1-30 bases 3' from the 3' end of the crRNA sequence or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

The one or more cleavable elements can be positioned in the sequence of the CRISPR polynucleotide, e.g., tracrRNA sequence, configured to bind to a CRISPR effector protein (e.g., Cas9). In some cases, the one or more cleavable elements can be 1-30 bases 3' of the 5' end of the tracr sequence, such as 2 bases, 3 bases, 4 bases, 5 bases, 6 bases, 7 bases, 8 bases, 9 bases, bases, 11 bases, 12 bases, 13 bases, 14 bases, 15 bases, 16 bases, 17 bases, 18 bases, 19 bases, bases, 21 bases, 22 bases, 23 bases, 24 bases, 25 bases, 26 bases, 27 bases, 28 bases, 29 bases, or 30 bases. In some cases, the one or more cleavable elements can be 1-30 bases 5' of the 3' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

In some examples, the one or more cleavable elements can be positioned immediately 5' or 3' of base (or nucleotide) 56 and/or nucleotide 73 in the CRISPR polynucleotide (e.g., sgRNA), wherein the 5'-most nucleotide of the guide sequence of the CRISPR polynucleotide (e.g., sgRNA) is nucleotide 1, or replace nucleotide 57 and/or nucleotide 74. In some examples, the one or more cleavable elements can be positioned immediately 5' or 3' of base (or nucleotide) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA), wherein the 5'-most base (or nucleotide) of the guide sequence of the CRISPR polynucleotide (e.g., sgRNA) is base (or nucleotide) 1 or replace base 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA).

B. Impact of the One or More Cleavage Elements Before Exposure to a Cleavage Agent In some cases, a CRISPR polynucleotide (e.g., sgRNA) comprising the one or more cleavable elements and complexed with a CRISPR effector protein (e.g., Cas9) does not have a reduced activity relative to a CRISPR polynucleotide (e.g., sgRNA) without the one or more cleavable elements and complexed to a CRISPR effector protein (e.g., before exposing the CRISPR polynucleotide to a cleavage agent). In some cases, a CRISPR polynucleotide (e.g., sgRNA) comprising the one or more cleavable elements and complexed with a CRISPR effector protein (e.g., Cas9) does have a reduced activity relative to a CRISPR polynucleotide (e.g., sgRNA) without the one or more cleavable elements and complexed to a CRISPR effector protein (e.g., before exposing the CRISPR polynucleotide to a cleavage agent).

C. Cleavage of the One or More Cleavable Elements

The one or more cleavable elements can be any cleavable element described herein. The one or more cleavable elements can be the same type of cleavable element or different types of cleavable elements. The one or more cleavable elements can be at least, or at most, 2, 3, 4, 5, 6, 7, 8, 9 or 10 cleavable elements.

The CRISPR polynucleotide (e.g., sgRNA) can be cleaved at the one or more cleavable elements while the CRISPR polynucleotide (e.g., sgRNA) is not bound to a CRISPR effector protein (e.g., Cas9). The CRISPR polynucleotide (e.g., sgRNA) can be cleaved at the one or more cleavable elements while the CRISPR polynucleotide (e.g., sgRNA) is complexed with a CRISPR effector protein (e.g., Cas9). The CRISPR polynucleotide (e.g., sgRNA) can be cleaved at the one or more cleavable elements while the CRISPR polynucleotide (e.g., sgRNA) is complexed with a CRISPR effector protein (e.g., Cas9) and bound to a target sequence. In some cases, following cleavage, one or more of the resulting fragments of the CRISPR polynucleotide (e.g., sgRNA) remains bound to the CRISPR effector protein (e.g., Cas9). In some cases, following cleavage, one or more (or all) of the resulting fragments of the CRISPR polynucleotide (e.g., sgRNA) no longer bind, or are no longer capable of binding to, a CRISPR effector protein (e.g., Cas9).

The CRISPR polynucleotide can be cleaved at the one or more cleavable elements in vitro. The CRISPR polynucleotide can be cleaved at the one or more cleavable elements in vivo. The CRISPR polynucleotide can be cleaved at the one or more cleavable elements while in a cell or organism, e.g., mouse, rabbit, goat, primate, e.g., chimpanzee, gorilla, or human.

The timing of the cleaving of the CRISPR polynucleotide (e.g., sgRNA) at the one or more cleavable elements can vary. For example, the one or more cleavable elements can be cleaved immediately after the CRISPR polynucleotide (e.g., sgRNA) is introduced into a cell or organism, or at least (or at most) 0.25, 0.5, 0.75, 1, 2, 3, 4, 5, 6, 7, 8, 9, 10, 11, 12, 13, 14, 15, 16, 17, 18, 19, 20, 21, 22, 23, 24, 48, 72, or 96 hours after introduction into a cell or organism.

A CRISPR polynucleotide (e.g., sgRNA) can be exposed to a cleavage agent once. A CRISPR polynucleotide (e.g., sgRNA) can be subjected to a cleavage agent more than once, e.g., 2 times, 3 times, 5 times, or 10 times. The CRISPR polynucleotide (e.g., sgRNA) can be exposed to more than one type of cleavage agent, e.g., at least (or at most) 2, 3, 4, 5, 6, 7, 8, 9, or cleavage agents.

A CRISPR polynucleotide (e.g., sgRNA) can be exposed to a cleavage agent for varying durations. For example, a CRISPR polynucleotide (e.g., sgRNA) can be exposed to a cleavage agent for 0.1 min, 0.5 min, 1 min, 2 min, 3 min, 4 min, 5 min, 10 min, 30 min, 60 min, 2 hr, 4 hr, 6 hr, 12 hr, 24 hr, 48 hr, 72 hr, or 96 hr.

In some cases, a sample comprises a plurality of CRISPR polynucleotides (e.g., sgRNAs), and a cleavage agent can be used to cleave a certain percentage of the CRISPR polynucleotides (e.g., sgRNAs). For example, a cleaving agent can be used to cleave at least (or at most) 5%, 10%, 15%, 20%, 25%, 30%, 35%, 40%, 45%, 50%, 55%, 60%, 65%, 70%, 75%, 80%, 85%, 90%, 95%, or 99% of the CRISPR polynucleotides (e.g., sgRNAs) in the sample. A dose of a cleaving agent can be used to cleave 100% of the CRISPR polynucleotides (e.g., sgRNAs) in the sample. The amount of cleavage can occur over at least (or at most) 1 min, 5 min, 10 min, 15 min, 30 min, 45 min, 1 hr, 2 hr, 6 hr, 12 hr, 24 hr, 48 hr, 72 hr, or 96 hr.

Cleavage can result in a decrease in activity of a CRISPR effector protein (e.g., CRISPR enzyme, e.g., Cas9) bound to the CRISPR polynucleotide (e.g., sgRNA). In some cases, in a sample, exposure to one or more cleavage agents results in at least a 0.1-fold, 0.25 fold, 0.5 fold, fold, 1 fold, 2 fold, 5 fold, 10 fold, 50 fold, 100 fold, or 1000 fold decrease in activity. In some cases, in a sample, exposure to one more cleavage agents results in complete loss of activity.

CRISPR OFF complexes can be used to reduce off target editing as compared to Cas9 complexed with a standard sgRNA. Off-target editing can be determined using ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv or deep-sequencing techniques as described in Tsai et al. "GUIDE-seq enables genome-wide profiling of off-target cleavage by CRISPR-Cas nucleases", Nature Biotechnology 33, 187-197 (2015).

V. CRISPR OFF Polynucleotides and Reduced Off-Target Editing

The CRISPR OFF polynucleotide can comprise one or more modifications such that, when the polynucleotide is complexed with a CRISPR effector protein, (e.g., Cas9), to form a CRISPR complex, the CRISPR complex has a lower off-target editing activity than a CRISPR complex with a polynucleotide without the one or more modifications when not exposed to light or another cleavage-inducing treatment. The one or more modifications can be one or more linkers described herein. The one or more modifications can be one or more cleavable linkers described herein. The one or more modifications can be one or more modifications at a 2' position of a ribose as described herein. The one or more modifications can be one or more cleavable elements. The one or more modifications can comprise 3-(4,4'-Dimethoxytrityl)-1-(2-nitrophenyl)-propan-1-yl-[(2-cyanoethyl)-(N,N-diisopropyl)]-phosphoramidite. The CRISPR OFF polynucleotide can further comprise 2'-O-methyl analogs and 3' phosphorothioate internucleotide linkages at the first three 5' and 3' terminal RNA nucleotides.

A. Position of the One or More Modifications

The one or more modifications can be positioned 3' of the 5'-most base (or nucleotide) in the guide sequence or 5' of the 3' most base (or nucleotide) in the guide sequence. The one or more modifications can be positioned about 1-30 bases 3' of the 5' end of the crRNA or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. The one or more modifications can be positioned about 1-30 bases 3' from the 5' end of the crRNA sequence or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

Figure 17:
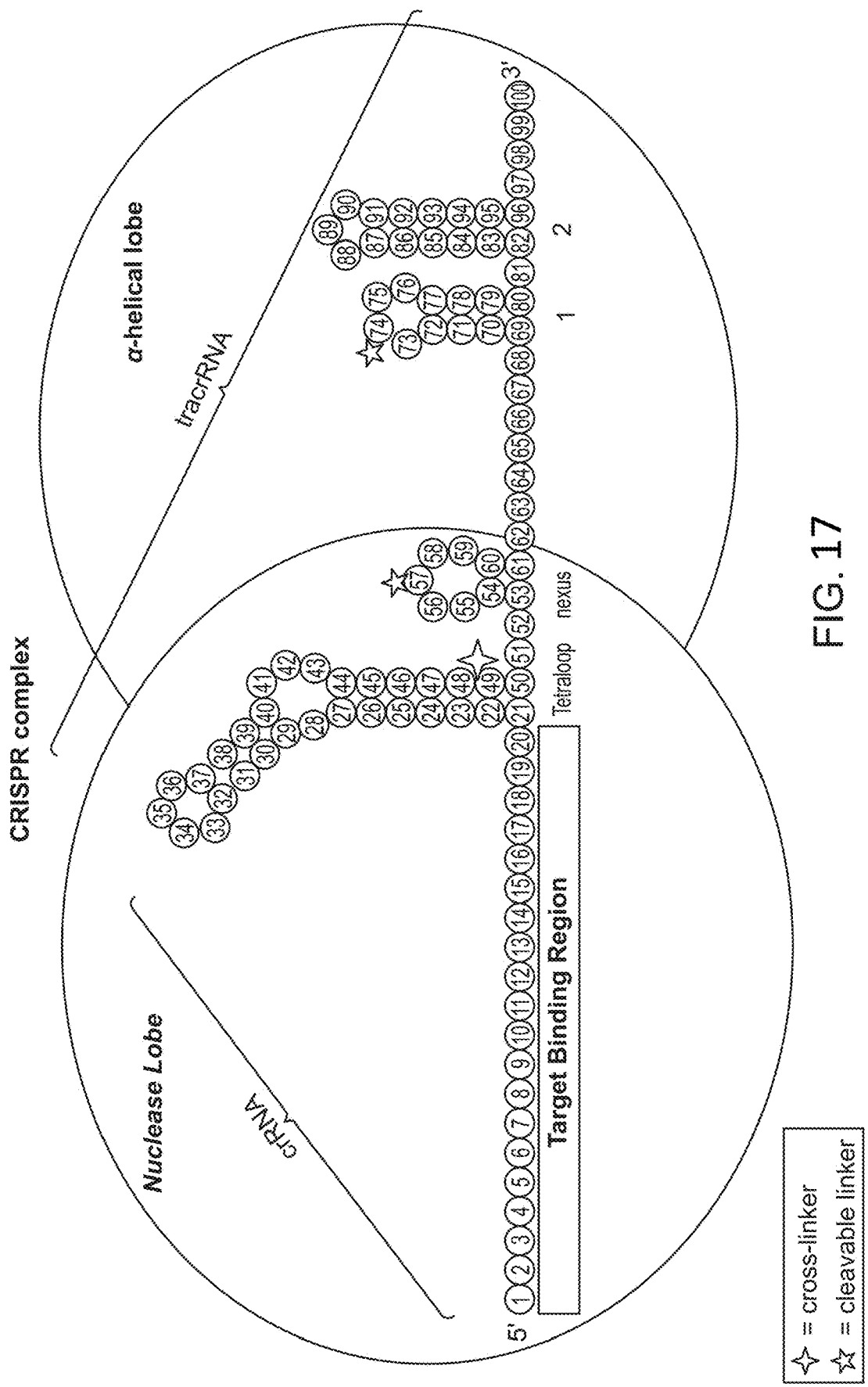
FIG. 17 illustrates exemplary positions at which a modification can be made to a CRISPR polynucleotide.

The one or more modifications can be positioned in the sequence of the CRISPR polynucleotide, e.g., tracrRNA sequence, configured to bind to a CRISPR effector protein (e.g., Cas9). In some cases, the one or more modifications can be in a tetraloop, nexus, stem loop 1, or stem loop 2 of the CRISPR polynucleotide shown in FIG. 17. In some cases the one or more modifications can be a loop of the tetraloop, a bulge of the tetraloop, a first stem of the tetraloop, a second stem of the tetraloop, in a loop structure of the nexus, in the stem of the nexus, in a loop structure of stem loop 1, in a stem of stem loop 1, in a loop structure of stem loop 2, or in a stem of stem loop 2; examples of the tetraloop, nexus, stem loop 1, and stem loop 2 are illustrated in FIG. 17. In some cases, the one or more modifications does not include sequence 5' of the guide sequence configured to form a stem loop, e.g., with the guide sequence. In some cases, the one or more modifications can be 1-30 bases 3' of the 5' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. In some cases, the one or more modifications can be 1-30 bases 5' of the 3' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

In some examples, the one or more modifications can be positioned immediately 5' or 3' of base (or nucleotide) 56 and/or nucleotide 73 in the CRISPR polynucleotide (e.g., sgRNA), wherein the 5'-most nucleotide of the guide sequence of the CRISPR polynucleotide (e.g., sgRNA) is nucleotide 1, or replace nucleotide 57 and/or nucleotide 74. In some examples, the one or more complex altering elements can be positioned immediately 5' or 3' of base (or nucleotide) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA), wherein the 5'-most base (or nucleotide) of the guide sequence of the CRISPR polynucleotide (e.g., sgRNA) is base (or nucleotide) 1 or replace base 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA).

B. Impact of the One or More Modifications

In some cases, a CRISPR polynucleotide (e.g., sgRNA) comprising the one or more modifications and complexed with a CRISPR effector protein (e.g., Cas9) does not have a reduced editing activity at a target sequence relative to a CRISPR polynucleotide (e.g., sgRNA) without the one or more modifications and complexed to a CRISPR effector protein (e.g., before exposing the CRISPR polynucleotide to a cleavage agent). In some cases, a CRISPR polynucleotide (e.g., sgRNA) comprising the one or more modifications and complexed with a CRISPR effector protein (e.g., Cas9) does have a reduced editing activity at a target sequence relative to a CRISPR polynucleotide (e.g., sgRNA) without the one or more complex altering elements and complexed to a CRISPR effector protein (e.g., before exposing the CRISPR polynucleotide to a cleavage agent). In some cases, editing activity at a target sequence is reduced about 1%, 2%, 3%, 4%, 5%, 6%, 7%, 8%, 9%, or 10% or at most 1%, 2%, or 3%, 4%, 5%, 6%, 7%, 8%, 9%, or 10% relative to a standard CRISPR complex.

In some cases, a CRISPR polynucleotide (e.g., sgRNA) comprising the one or more modifications and complexed with a CRISPR effector protein (e.g., Cas9) has a reduced editing activity at an off-target sequence relative to a CRISPR polynucleotide (e.g., sgRNA) without the one or more modifications and complexed to a CRISPR effector protein (e.g., before exposing the CRISPR polynucleotide to a cleavage agent). Editing activity at an off-target sequence can be described as off-target editing. Off-target editing can be editing at a sequence that is not exactly complementary to the guide sequence of the CRISPR polynucleotide. In some cases, the editing activity at an off-target sequence is reduced about, at least, or at most 5%, 10%, 15%, 20%, 25%, 30%, 40%, 50%, 60%, 70%, 80%, 90%, or 100%. In some cases, the off-target editing activity is 0%, 1%, 5%, 10%, 15%, 20%, 25%, 30%, 40%, 50%, 60%, 70%, 80%, 90%, or 95%. In some cases, the off-target editing activity is less than 1%, 5%, 10%, 15%, 20%, 25%, 30%, 40%, 50%, 60%, 70%, 80%, 90%, or 95%. In some cases, the off-target editing activity is 0%-5%, 5%-10%, 10%-25%, 25%-50%, 50%-75%, or 75%-95%.

The off-target editing activity (e.g., as measured as described herein) can be reduced by a factor of: about 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 51, 52, 53, 54, 55, 56, 57, 58, 59, or 60; at least 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, or 60; or at most 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, or 60.

In some cases, the off-target editing activity is measured at one nucleic acid region. The off-target editing activity can be measured at more than one genomic region (e.g., gene). The off-target editing activity can be measured at 1, 2, 3, 4, 5, 6, 7, 8, 9, 10, 25, 50, 75, or 100 genomic regions (e.g., genes). The off-target editing activity can be measured at 1, 2, 3, 4, 5, 6, 7, 8, 9, 10, 25, 50, 75, 100, 1000, or 10,000 genomic regions (e.g., genes). The off-target editing activity can be measured at most 1, 2, 3, 4, 5, 6, 7, 8, 9, 10, 25, 50, 75, 100, 1000, or 10,000 genomic regions (e.g., genes).

The off-target editing activity can be measured by analyzing nucleic acid molecules from a cell contacted by CRISPR complex. The measurement can be made using nucleic acid molecules extracted from the cells, about, or at most 30 minutes, 1 hours, 2 hours, 5 hours, 10 hours, 12 hours, 24 hours, 36 hours, 48 hours, 60 hours, 72 hours, 4 days, 5 days, or 6 days after transformation. The CRISPR complex can be introduced into the cell by transfection. The nucleic acid molecules can be analyzed by, e.g., sequencing, PCR, mass spectrometry, southern blot, etc. The off-target editing can be visualized, e.g., by presenting data in, e.g., graph, e.g., scatterplot.

CRISPR complexes comprising a CRISPR polynucleotide can be used to reduce off-target editing as compared to Cas9 complexed with an sgRNA without a modification as described herein. Off-target editing can be determined using ICE (Inference of CRISPR Editing) to measure the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv or deep-sequencing techniques as described in Tsai et al. "GUIDE-seq enables genome-wide profiling of off-target cleavage by CRISPR-Cas nucleases", Nature Biotechnology 33, 187-197 (2015).

Off target editing sites can have sequences that have a high percent sequence identity to the target sequence. The sequence identity can be less than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31% or 30%. Off target editing sites can have sequences that are close in proximity to a PAM region, for example mismatches between the guide RNA and DNA may be tolerated at the 5' end of the protospacer (distal to the PAM) to produce an off-target edit. Those of skill in the art readily understand how to determine sequence identity between two nucleic acids. For example, the sequence identity can be calculated after aligning the two sequences so that the sequence identity is at its highest level. Another way of calculating sequence identity can be performed by published algorithms. Optical alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

VI. Cleavable Elements

The one or more cleavable elements can be any cleavable element described herein.

A. Types of Cleavable Elements

The cleavage property of the CRISPR polynucleotide can be altered by a cleavable element that can alter the propensity of cleavage of the CRISPR polynucleotide at the point of its incorporation, under appropriate conditions. A "cleavable element" can comprise natural nucleotides or one or more modified nucleotides. The cleavable element can be incorporated into the CRISPR polynucleotide (e.g., sgRNA) during nucleic acid synthesis.

Two or more cleavable elements in a CRISPR polynucleotide can have different cleavage characteristics, e.g., the two or more cleavable elements, when incorporated into a CRISPR polynucleotide (e.g., sgRNA), can be selectively cleaved in each other's presence by using different agents and/or reaction conditions.

As used herein, the terms "cleaving," "cleaved" and "cleavage" can all relate to the scission of the CRISPR polynucleotide (e.g., sgRNA) substantially at each point of occurrence of a cleavable element in the CRISPR polynucleotide (e.g., sgRNA).

The cleavage can be initiated by an agent. The agent can be, e.g., a chemical entity or physical force that causes the cleavage of a cleavable element. The agent can be a chemical or combination of chemicals, a biomolecule or combination of biomolecules, normal or coherent (laser) visible or ultraviolet (UV) light, heat or other forms of electromagnetic energy. In some cases, a combination of agents, e.g., two or more agents, can be used simultaneously or sequentially to cleave a CRISPR polynucleotide (e.g., sgRNA). By simultaneously is meant a CRISPR polynucleotide (e.g., sgRNA) can be exposed to the two or more agents at the same time, although the two or more agents can react with the CRISPR polynucleotide (e.g., sgRNA) one at a time. By sequentially is meant that the CRISPR polynucleotide (e.g., sgRNA) can be contacted with one agent and then a second agent at a later time.

A CRISPR polynucleotide (e.g., sgRNA) can comprise more than one type of cleavable element. In some examples, the first cleavable element and the second cleavable element have the same cleavage characteristics. In some examples, the second cleavable element has different cleavage characteristics than the first cleavable element. For example, the first cleavable element can be a photocleavable linker and the second cleavable element can be susceptible to cleavage by a chemical nuclease. In another example, the first cleavable element can be susceptible to cleavage by a chemical nuclease, and the second cleavable element can be engineered to be photocleavable allowing orthogonal treatment regimens to be applied. In some cases, the same cleavable element can have more than one type of cleavage characteristic. The first and second cleavable element can be any cleavable element described herein.

A cleavable element (e.g., cleavable linker) can refer to an entity that can connect two or more constituents of a CRISPR polynucleotide (e.g., sgRNA) that renders the CRISPR polynucleotide (e.g., sgRNA) susceptible to cleavage under appropriate conditions. For instance, the appropriate conditions can be exposure to UV light. The cleavable linker can comprise one or more modified or unmodified nucleotides, which are susceptible to scission under the appropriate conditions.

The cleavable linker can comprise a modified internucleoside linkage. The modified internucleoside linkage can be an internucleotide linkage that has a phosphorus atom or those that do not have a phosphorus atom. Internucleoside linkages containing a phosphorus atom therein include, for example, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, P-ethyoxyphosphodiester, P-ethoxyphosphodiester, P-alkyloxyphosphotriester, methylphosphonate, thionophosphoramidates, thionoalkylphosphonates, thionoalkylphosphotriesters, selenophosphates and boranophosphates, and nonphosphorus containing linkages, e.g., acetals and amides, such as are known in the art, having normal 3'-5' linkages, 2'-5' linked analogs of these, and those having inverted polarity wherein one or more internucleotide linkages is a 3' to 3', 5' to 5' or 2' to 2' linkage. Polynucleotides having inverted polarity can comprise a single 3' to 3' linkage at the 3'-most internucleotide linkage i.e. a single inverted nucleoside residue which may be abasic (the nucleobase is missing or has a hydroxyl group in place thereof).

Non-phosphorus containing internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and CH2 component parts. Other modified internucleoside linkages that do not contain a phosphorus atom therein include, —CH$_2$—NH—O—CH$_2$—, —CH$_2$—N(CH$_3$)—O—CH$_2$— (known as a methylene (methylimino)backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$—.

The cleavable linker can be non-nucleotide in nature. A "non-nucleotide" can refer to any group or compound that can be incorporated into a polynucleotide chain in the place of one or more nucleotide units, including either sugar and/or phosphate substitutions. The group or compound can be abasic in that it does not contain a commonly recognized nucleotide base, such as adenosine, guanine, cytosine, uracil or thymine, for example at the C1 position of the sugar.

Non-nucleotidic linkers can be e.g. abasic residues (dSpacer), oligoethyleneglycol, such as triethyleneglycol (spacer 9) or hexaethylenegylcol (spacer 18), or alkane-diol, such as butanediol. The spacer units can be preferably linked by phosphodiester or phosphorothioate bonds. The linker units may appear just once in the molecule or may be incorporated several times, e.g. via phosphodiester, phosphorothioate, methylphosphonate, or amide linkages. Further preferred linkers are alkylamino linkers, such as C3, C6, C12 aminolinkers, and also alkylthiol linkers, such as C3 or C6 thiol linkers. In some examples, heterobifunctional and homobifunctional linking moieties may be used to conjugate peptides and proteins to nucleotides. Examples include 5'-Amino-Modifier C6 and 3'-Amino-Modifier C6 reagents.

B. Methods of Cleaving Cleavable Elements

The cleavable element can be cleaved by any suitable method, including exposure to acid, base, nucleophile, electrophile, radical, metal, reducing or oxidizing agent, light, temperature, enzymes, small molecule, nucleic acid, protein, etc. In some examples, the cleavable element (e.g., cleavable linker) is susceptible to cleavage by a cellular process or byproduct thereof. The cellular process can involve enzyme, second messenger molecules, metabolites, proteins, and free radicals.

C. Photolabile Groups

The cleavable element can be a photolabile group. The photolabile group can be introduced into the CRISPR polynucleotide by phosphoramidite chemistry. Selective reaction of PC-aminotag phosphoramidites with the free 5'-OH group of a growing oligonucleotide chain, followed by cleavage from the support and deprotection, can result in the introduction of a phosphodiester group linked to a primary aliphatic amino group through a photocleavable linker. This amino group can then be used to introduce a variety of photocleavable markers through a postsynthetic modification reaction with amine reactive reagents (Olejnik J et. al, Nucleic acids research. 1998; 26:3572-6. For example, a CRISPR polynucleotide can comprise a photocleavable aliphatic group linking two nucleotides (e.g., nucleotide 53 and nucleotide 54) in the CRISPR polynucleotide, and the CRISPR polynucleotide can be exposed to UV light, resulting in a break in the CRISPR polynucleotide (e.g., between nucleotide 53 and 54). In other examples, a photocleavable aminotag phosphoramidite can be positioned in a CRISPR polynucleotide between the polynucleotide leader sequence and the guide sequence, and UV light can be used to initiate cleavage at the photocleavable aminotag phosphoramidite, thereby separating the polynucleotide leader sequence. An example of a photocleavable linker that can be used to initiate cleavage of the CRISPR polynucleotide can be 3-(4,4'-Dimethoxytrityl)-1-(2-nitrophenyl)-propan-1-yl-[(2-cyanoethyl)-(N,N-diisopropyl)]-phosphoramidite. For example, a CRISPR polynucleotide can comprise a photocleavable aliphatic group linking two nucleotides (e.g., nucleotide 53 and nucleotide 54) in the CRISPR polynucleotide, and the CRISPR polynucleotide can be exposed to visible light, resulting in a break in the CRISPR polynucleotide (e.g., between nucleotide 53 and 54). In other examples, a photocleavable coumarin photolinker can be positioned in a CRISPR polynucleotide between the polynucleotide leader sequence and the guide sequence, and visible light can be used to initiate cleavage at the photocleavable coumarin photolinker, thereby separating the polynucleotide leader sequence. An example of a photocleavable linker that can be used to initiate cleavage of the CRISPR polynucleotide can be a coumarin linker. Other methods of introducing photocleavable linkers into polynucleotide sequences have been described, e.g., in US Patent Applications: US20080227742A1, US20100022761A1, U.S. Pat. No. 7,897,737B2, the contents of which have been referenced here in their entirety.

D. Ribonuclease Based Cleavage

In some examples, the one or more cleavable elements comprise a cleavage site for an endoribonuclease, e.g., an endoribonuclease which cleaves RNA at or within a defined ribonucleotide sequence motif. For example, the cleavable element can comprise a cleavage site recognized by a sequence-specific endoribonuclease. The endoribonuclease can be naturally occurring or engineered. In some examples, the endoribonuclease can be specific for single stranded RNA, double stranded RNA or a nucleotide sequence formed by a DNA:RNA hybrid. In some examples, the sequence-specificity of the endoribonuclease can be engineered by fusion with oligonucleotides or by fusion with other protein domains. For example, a sequence specific endoribonuclease enzyme can be engineered by fusing two functionally independent domains, a RNase HI, that hydrolyzes RNA in DNA-RNA hybrids in processive and sequence-independent manner, and a zinc finger that recognizes a sequence in DNA-RNA hybrids. In another conjugation of an antisense oligodeoxynucleotide to ribonuclease H can result in sequence-specific cleavage. See e.g., Sulej et. al, Nucleic acids research. 2012; 40(22):11563-70 and Fukuma et. al, Bioconjugate chemistry. 2003; 14(2):295-301. In some cases, the cleavable element can be capable of recruiting RNase H1 to cleave double stranded regions of the CRISPR polynucleotide. (See, e.g., U.S. Pat. No. 5,849, 902).

The cleavable element can comprise a cleavage site recognized by a sequence-specific ssRNA endoribonuclease such as the excised IVS rRNA portion of the *Tetrahymena thermophila* as described, e.g., in Zaug et. al, Biochemistry 1988; 27, 25, 8924-8931. In other examples the cleavable element can comprise one or more cleavage sites recognized by sequence-specific ssRNA endoribonuclease Cas2 as described, e.g., in Beloglazova et. al, J Biol Chem. 2008; 283(29): 20361-20371. In other examples the cleavable element can comprise one or more preferred sites in dsRNA recognized by RNase Mini-III from *Bacillus subtilis*, e.g., as discussed in Glow et. al, Nucleic Acids Res. 2015; 43 (5) 2864-73. In other examples, Short oligonucleotides can be used as external guide sequences (EGSs) to direct site-specific cleavage of the CRISPR polynucleotide by human RNase P. For example, 13-mer EGSs targeted to the 2.1-kb surface antigen mRNA of hepatitis B virus (HBV) were capable of inducing cleavage of the HBV RNA by RNase P. (See Werner M et. al, RNA. 1998; 4(7):847-55. The endoribonuclease can be a member of the sequence or structure specific endoribonuclease Cas6 superfamily, e.g., Cas6A (e.g. Hong Li (2015), Structure, January 6; 23(1): 13-20). The endoribonuclease can be Csy4, also known as Cas6f. The ssRNA endoribonuclease can belong to the Cas13 family of CRISPR endoribonuclease or derivatives thereof. The endoribonuclease can be Cpf1 or a Cas5d enzyme, which can process pre-creRNA transcripts (Zetsche, B. et al. (2016), "Multiplex gene editing by CRISPR-Cpf1 using a single crRNA array", Nature Biotechnology (2016) doi: 10.1038/nbt.3737).

The cleavable element can be an element that is cleavable by ribozymes, e.g. the hammerhead ribozyme, Hepatitis delta virus ribozyme etc. The ribozymes can be naturally occurring or can be engineered to be a trans-acting ribozymes by separation into 'catalyst' and 'substrate' strands as discussed, e.g., in Levy et. al, RNA 2005. 11: 1555-1562. In some cases, two ribozymes can be used in concert to allow cleavage after a desired target sequence. In some cases, alternative artificial ribozyme—protein complexes that function in different cellular compartments can be designed by the use of localizing determinants for delivering a ribozyme to a specific subcellular site or for targeting a specific type of RNA as shown in Samarsky et. al, Proc Natl Acad Sci USA. 1999; 96(12): 6609-6614. In some cases, use of the ribozyme can involve binding of an exogenous small molecule for activity, e.g., glmS ribozyme.

In some examples, the activity of the ribozyme can be further tuned to be ligand-controlled by coupling with an aptamer. The aptamer can be chosen based on its ability to bind a ligand or otherwise "sense" a change in environment (such as pH, temperature, osmolarity, salt concentration, etc) in a manner directly coupled through an information transmission domain to loop I and/or loop II. The ligand can, for example, be a protein, nucleotide or small molecule ligand. The binding of the ligand to the aptamer can causes a change in the interaction of the information transmission domain with one or more of the loops, the stem or the catalytic core such that the ribozyme activity can be modulated dependent upon the presence or absence of the ligand as described, e.g., in U.S. Pat. No. 8,603,996B2.

Cleavage of the cleavable elements of the CRISPR polynucleotide (e.g., sgRNA) can be induced at a desired time independently; for example, a genetically-coded endoribonuclease can be activated within the host cells. A vector or plasmid encoding the endoribonuclease can be transfected into the cell at a desired time. One or more endoribonucleases can be under the control of one or more independent promoters. One or more of the promoters can be activated at desired times.

E. Antisense Oligonucleotides

The one or more cleavable elements of the CRISPR polynucleotide can be designed to allow the binding of an anti-sense oligonucleotide. The antisense oligonucleotide can be a single-stranded DNA (ssDNA) oligonucleotide. The ssDNA oligonucleotide can hybridize to single stranded RNA sequence in the CRISPR polynucleotide, and RNAse H can be used to cleave RNA of the DNA:RNA hybrid. With regard to the cleavable element (e.g., RNA loop of a stem loop in the CRISPR polynucleotide) to which the antisense oligonucleotide can bind, the cleavable element (e.g., loop of a stem loop) can be about 6 to about 40 nucleotides in length. The antisense oligonucleotide can be about 12 to about 16 nucleotides in length, or about 12 to about 25 nucleotides, or about 10 to about 30 nucleotides in length. The degree of complementarity between the antisense oligonucleotide and the cleavable element (e.g., loop of a stem loop) of the CRISPR polynucleotide can be at least 80%, 85%, 90%, 95%, 98%, 99%, or 100%. An antisense oligonucleotide whose sequence is fully or partially complementary to the cleavable element can be produced within the host cell or introduced into the host cell. Antisense oligonucleotides can be transfected into cells using polyethyleneimine (PEI) or other known transfection methods.

The one or more cleavable element of the CRISPR polynucleotide can comprise a miRNA responsive element. The length of the miRNA responsive element can be between about to about 30 nucleotides, e.g., about 20 to about 25 nucleotides in length. The length of the miRNA can be about 20 to about 24 nucleotides, e.g., about 21 to about 23 nucleotides, e.g., about 22 nucleotides in length. The degree of sequence complementarity between the miRNA and the miRNA responsive element in the CRISPR polynucleotide can be at least 80%, 85%, 90%, 95%, 98%, 99%, or 100%.

The cleavable element can comprise an miRNA response element (MRE), and an miRNA that is capable of binding to the MRE can be produced within the host cell or introduced into the host cell. The miRNA can be present in the form of an miRISC complex which can target the MRE and cleave the first cleavable element.

F. Site-Specific Chemical Nucleases

Specific cleavage of the CRISPR polynucleotide can be achieved by a chemical compound that has been designed to possess site-specific nuclease activity.

The chemical nuclease can be designed to have sequence-specific affinity to a CRISPR polynucleotide, e.g., CRISPR ON polynucleotide, CRISPR OFF polynucleotide, or CRISPR ON/OFF polynucleotide. For example, RNA cleaving tris(2-aminobenzimidazoles) can be attached to DNA oligonucleotides or 2'-O-methyloligoribonucleotide via disulfide or amide bonds to form organocatalytic nucleases showing RNA substrate and site selectivity (see e.g., Gnaccarini et. al, J. Am. Chem. Soc., 2006, 128 (24), pp 8063-8067]. In other examples, the site-specificity of the chemical RNAse (e.g., 1,10-phenanthroline moiety, neocuprine Zn (II), neamine) for the CRISPR polynucleotide can be achieved through the use of peptide nucleic acids (PNA), e.g., polyamide nucleic acid.

The site-specificity of the chemical RNAse (e.g., diethylenetriamine moiety) for the CRISPR polynucleotide can be achieved by a combined use of anti-sense oligonucleotides, peptides proteins or PNAs. In some examples, RNA-binding proteins can be chemically converted to sequence-specific nucleases by covalent attachment to a coordination complex, such as 1,10-phenanthroline-copper complex. See e.g., Chen et. al, Sigman DS. Science. 1987; 237(4819): 1197-201. In another example, site-specific cleavage of CRISPR polynucleotide can be achieved by the conjugation of Bleomycin-Fe (II) with EDTA or an oligonucleotide to form an artificial nuclease with specificity for the CRISPR polynucleotide.

Examples of chemical nucleases include 1,10-phenanthrolinecopper (Sigman et al., 1993), ferrous-ethylenediaminetetraacetic acid (EDTA), macrocylic lanthanide complexes, metalloporphyrins, metallic complexes of salens, uranyl acetate, octahedral metal complexes of rhodium (III), benzene diazonium tetrafluoroborate, aliphatic mono-amines-, diamines- and polyamines, aminoglycosides such as neomycin B and copper (II) aminoglycoside complexes etc. In some cases, the chemical nucleases can target the sugar moiety of nucleosides and catalyze oxidative cleavage by extracting a hydrogen atom from the sugar at the cleavage site.

G. Photochemical Cleavage

In some examples, photocaging groups can be used to render further control on the activity of the agent used for the cleavage of the CRISPR polynucleotide. For example, photolysis of photoactivatable or "caged" probes can be used for controlling the release of site-specific chemical nucleases described in this disclosure. In another example, a photocaging group can be used to block cleavage by a ribonuclease or restriction enzyme of the CRISPR polynucleotide, until released by photolysis, e.g., as shown in Bohacova et. al, Biomol. Chem., 2018. 16, 1527. In another example, a photocaging group on one or more of the nucleotides in the CRISPR polynucleotide can be used to mask the recognition sequence for an anti-sense nucleotide, until release by photolysis, thereby initiating cleavage of the CRISPR polynucleotide. In another example, the photocaging group can be attached to the cleavage agent, such as the anti-sense oligonucleotide, which upon photolysis, becomes available for binding to the CRISPR polynucleotide and initiating the formation of a RISC complex. In another example, the photocaging group can be used to mask a 'miRNA response element' for cleavage of the CRISPR polynucleotide until release by photolysis. In other aspects, without limitation, photocaging groups can be used with orthogonal treatment regimens for the cleavage of multiple cleavage elements with different cleavage characteristics.

Photocaging groups can be used for 'tagging' the cleavage reaction, wherein the tag can be amenable for detection and/or quantification by one or more methods. For example, a 2-nitro-benzyl based photocleavable group can be labeled further with a dye that is released upon photolysis, and can be used as a detectable marker for the 'efficiency' of activation of the CRISPR ON polynucleotide or for the deactivation of the CRISPR OFF polynucleotide etc. In another example, the ribonuclease protein that binds to the cleavable element of CRISPR polynucleotide can be tagged upon initiation of the 'cleavage event' by the release of a 'fluorescent tag' from photocaged nucleotide that was incorporated into the cleavable element, wherein measurement of the fluorescent tag can be a surrogate marker for the cleavage of the CRISPR polynucleotide.

Examples of photocaging groups that can be synthetically incorporated into the CRISPR polynucleotide include ortho-nitrobenzyl based caging groups that can by linked to a heteroatom (usually O, S or N) as an ether, thioether, ester (including phosphate or thiophosphate esters), amine or similar functional group by methods known in the art. Examples of 2-nitrobenzyle based caging groups include α-carboxy-2-nitrobenzyl, 1-(2-nitrophenyl)ethyl, 4,5-dimethoxy-2-nitrobenzyl, 1-(4,5-dimethoxy-2-nitrophenyl)ethyl, 5-carboxymethoxy-2-nitrobenzyl, nitrophenyl etc. Other examples of photoremovable protecting groups, include benzyloxycarbonyl, 3-nitrophenyl, phenacyl, 3,5-dimethoxybenzoinyl, 2,4-dinitrobenzenesulphenyl, Ethedium Monoazide, Bimane Azide and their respective derivatives.

Photolabile linkers described herein can be represented as several mesomeric forms. Where a single structure is drawn, any of the relevant mesomeric forms are intended. The coumarin linkers described herein represented by a structural formula can be shown as any of the related mesomeric forms. Exemplary mesomeric structures are shown below for Formula (I'):

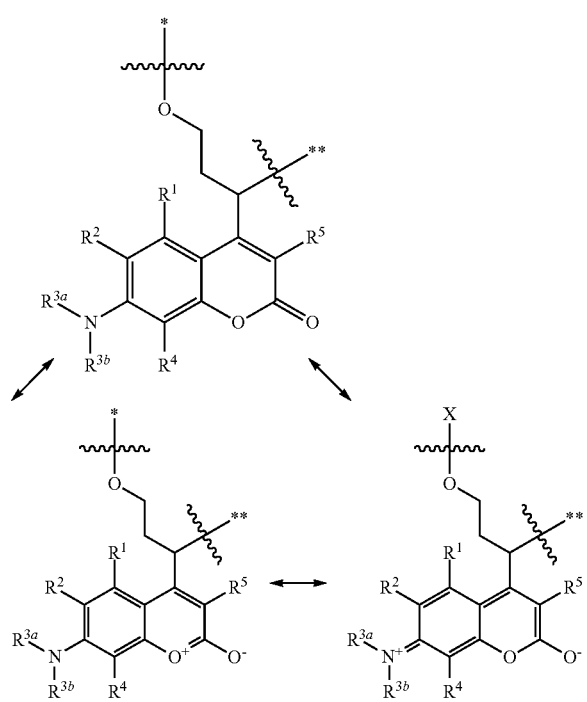

Photolabile protective groups can be attached to the hydroxy and phosphate or nucleobase in nucleosides and nucleotides. For example, photocaged derivatives of 2'-deoxy-5-(hydroxymethyl) uridine nucleoside, mono- and triphosphates protected by 2-nitrobenzyl-, 6-nitropiperonyl- and anthryl-9-methyl groups can be enzymatically incorporated into the polynucleotide, e.g., as described in Bohacova et. al, Org. Biomol. Chem., 2018, 16, 152. Photocleavage can occur through a variety of mechanisms such as hydrogen bond abstraction from sugar ring, direct electron transfer from the base to the photo excited cleaver or singlet oxygen production by transfer of energy from the photocleavage and formation of adducts.

H. Cleavage of Cleavable Element

The cleavable element(s) of the two or more (e.g., 2, 3, 4, 5, 6, 7, 8, 9 or 10) CRISPR polynucleotides can be cleaved by the same cleaving moiety. The cleavage of the two or more (e.g. 2, 3, 4, 5, 6, 7, 8, 9 or 10) different CRISPR polynucleotides can be induced by different external factors.

The cleavage inducing agent can be electromagnetic radiation. The cleavage inducing agent can be a particular wavelength of light in the visible spectrum. The cleavage element can be cleaved by UV light.

The wavelength of the light can range from 220-465 nm. The intensity of light in the exposure protocol can be about 5, 10, 15, 20, 25, 35, 40, 50, 70, 90, 110, 120, 140, 160, 175, 190, 200, 220, 240, 260 280, 300, 320, 340, 360, 380, 400, 420, 440, 460, 480, 500, 520, 540, 560, 580, 600, 620, 650, 675, 700, 720, 745, 765, 790, 810, 830, 850, 870, 900, 920, 945, 965, 985, 1000, 1025, 1050, 1080, 1100, 1125, 1150, 1175, 1200, 1240, 1275, 1290, 1320, 1350, 1380, 1400, 1420, 1450, 1470, 1490, 1520, 1540, 1560, 1600, 1630, 1650, 1670, 1700, 1720 or 1750 mW/cm$^2$. The intensity of light in the exposure protocol can range from about 70 mW/cm$^2$ to 100 mW/cm$^2$, 80 mW/cm$^2$ to 110 mW/cm$^2$, 90 mW/cm$^2$ to 120 mW/cm$^2$, 100 mW/cm$^2$ to 130 mW/cm$^2$, 110 mW/cm$^2$ to 140 mW/cm$^2$, 120 mW/cm$^2$ to 150 mW/cm$^2$, 130 mW/cm$^2$ to 160 mW/cm$^2$, 140 mW/cm$^2$ to 170 mW/cm$^2$, 150 mW/cm$^2$ to 180 mW/cm$^2$, 160 mW/cm$^2$ to 190 mW/cm$^2$, 170 mW/cm$^2$ to 200 mW/cm$^2$, 180 mW/cm$^2$ to 210 mW/cm$^2$, 190 mW/cm$^2$ to 220 mW/cm$^2$, 200 mW/cm$^2$ to 230 mW/cm$^2$, 210 mW/cm$^2$ to 240 mW/cm$^2$, 220 mW/cm$^2$ to 250 mW/cm$^2$, 230 mW/cm$^2$ to 260 mW/cm$^2$, 240 mW/cm$^2$ to 270 mW/cm$^2$, 250 mW/cm$^2$ to 280 mW/cm$^2$, 260 mW/cm$^2$ to 290 mW/cm$^2$, or 270 mW/cm$^2$ to 300 mW/cm$^2$. The wavelength of the light can range from about 320 nm to about 390 nm. The wavelength of the light can range from about 320 nm to 425 nm, 320 nm to 420 nm, 420 nm to 520 nm, 520 nm to 620 nm. 420 nm to 700 nm. The wavelength of light can be greater than about 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, or 700 nm. The wavelength of light can be less than about 700 nm, 690 nm, 680 nm, 670 nm, 660 nm, 650 nm, 640 nm, 630 nm, 620 nm, 610 nm, 600 nm, 590 nm, 580 nm, 570 nm, 560 nm, 550 nm, 540 nm, 530 nm, 520 nm, 510 nm, 500 nm, 490 nm, 480 nm, 470 nm, 460 nm, 450 nm, 440 nm, 430 nm, or 425 nm. The wavelength of light can range from about 420 nm to 430 nm, 430 nm to 440 nm, 440 nm to 450 nm, 450 nm to 460 nm, 460 nm, to 470 nm, 470 nm to 480 nm, 480 nm to 490 nm, 490 nm to 500 nm, 500 nm to 510 nm, 510 nm to 520 nm, 520 nm to 530 nm, 530 nm to 540 nm, 540 nm to 550 nm, 550 nm to 560 nm, 560 nm to 570 nm, 570 nm to 580 nm, 580 nm to 590 nm, 590 nm to 600 nm, 600 nm to 610 nm, 610 nm to 620 nm, 620 nm to 630 nm, 630 nm to 640 nm, 640 nm to 650 nm, 650 nm to 660 nm, 660 nm to 670 nm, 670 nm to 680 nm, 680 nm to 690 nm, or 690 nm to 700 nm. The power wattage of the light used in the exposure protocol can be about 50, 70, 80, 90, 100, 120, 140, 160, 175, 190, 210, 230, 250, 270, 290, 310, 330, 250, 370, 390, 420, 4450, 480, 500, 530, 550, 570, 600, 620, 650, 670, 700, 720, 750, 770, 800, 820, 850, 870, 900, 920, 950, 970, 1000, 1020, 1050, 1070, 1100, 1120, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400 4500, 4600, 4700, 4800, 4900, 5000, 5100, 5200, 5300, 5400, 5500, 5600, 5700, 5800, 5900, or 6000 W, as measured by an OAT 306 UV power meter.

The duration of exposure can be from 1 second to 30 minutes. The duration of exposure can be from 1 second to 30 seconds, 30 seconds to 60 seconds, 1 min to 5 min, 5 min to 10 min, min to 20 min, 20 min to 30 min, 30 min to 40 min, 40 min to 50 min, or 50 min to 1 hr. The duration of exposure can be greater than about one hour, 50 min, 40 min, 30 min, 20 min, 10 min, 5 min, 1 min, 30 seconds, or one second. The duration of exposure can be less than about two seconds, 30 seconds, 1 min, 5 min, 10 min, 20 min, 30 min, 40 min, 50 min, or 1 hour. The exposure protocol can comprise continuous exposure or pulsed exposure or both. The pulse exposure can be uniform or of varying durations.

The light source can be a broad spectrum light that has been filtered through a bandpass filter. The bandpass filter can be a 345 nm bandpass filter. The bandpass filter can be a 420 nm long pass filter. The light source can be an ultraviolet (UV) light. The light source can be a LED. The LED can emit ultraviolet light. The LED can emit visible light. The LED can emit infrared light.

VII. Functions of CRISPR Complexes

CRISPR complexes described herein can be used for different functions. The functions can include enzymatic activity, e.g., target specific nucleic acid editing. In some cases, catalytically dead CRISPR effector proteins can be used for form CRISPR complexes. In some cases, one of more functional domains can be covalently or noncovalently linked to a CRISPR complex, e.g., through a CRISPR polynucleotide or a CRISPR effector protein, or both.

A. CRISPR Polynucleotide Stem-Loops and RNA Binding Proteins

The CRISPR polynucleotide (e.g., sgRNA) can comprise one or more stem loops to which one or more stem-loop RNA binding proteins (RBPs) are capable of interacting. These stem loops can be positioned such that the interaction of the CRISPR polynucleotide (e.g., sgRNA) with the CRISPR effector protein (e.g., CRISPR enzyme) or binding of the CRISPR complex with a target DNA is not adversely affected. The one or more stem loops can lie outside the guide sequence of the CRISPR polynucleotide (e.g., the sgRNA). The one or more stem-loop RNA binding proteins can be, e.g., MS2, PP7, Qp, F2, GA, fr, JP501, M12, R17, BZ13, JP34, JP500, KU1, M11, MX1, TW18, VK, SP, Fl, ID2, NL95, TW19, AP205, S1, S1m, 7s, or PRR1.

In some cases, the stem-loop RNA binding protein (RBP) can act as an adaptor protein (i.e., intermediary) that can bind both to the stem-loop RNA and to one or more other proteins or polypeptides, or one or more functional domains. The adaptor protein can recruit effector proteins or fusions that can comprise one or more functional domains. In some cases, the RNA binding protein can be a fusion protein with one or more functional domains.

B. CRISRP Effector Proteins and Functional Domains.

In some cases, the one or more functional domains can be attached, directly or indirectly, to the CRISPR effector protein (e.g., CRISPR enzyme). One or more functional domains can be covalently fused to a CRISPR effector protein. The CRISPR effector protein can be a catalytically active Cas protein or a catalytically dead CRISPR protein.

C. Examples of Functional Domains

The one or more functional domains can be a nuclear localization sequence (NLS) or a nuclear export signal (NES).

The one or more functional domains can be a transcriptional activation domain. The transcriptional activation domain can be VP64, p65, MyoD1, HSF1, RTA, SETT/9, or a histone acetyltransferase.

The one or more functional domains can have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

The one or more functional domains can be a transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase, or histone tail protease.

In some cases, the functional domain can be linked to a dead CRISPR effector protein (e.g., dead-Cas9 enzyme). The functional domain linked to the dead CRISPR effector protein (e.g., dead-Cas9 enzyme) can used to bind to and/or activate a promoter or enhancer. One or more CRISPR polynucleotides comprising a guide sequence that can anneal to the promoter or enhancer can also be provided to direct the binding of a CRISPR complex comprising a CRISPR effector protein (e.g., dead-Cas9) to the promoter or enhancer.

D. Mutations in CRISPR Effector Protein

The CRISPR effector protein, e.g., Cas9, can comprise one or more mutations (and hence nucleic acid molecule(s) coding for same can have mutation(s)). The one or more mutations can be artificially introduced mutations and can be one or more mutations in a catalytic domain. Examples of catalytic domains with reference to a Cas9 enzyme can be RuvC I, RuvC II, RuvC III and HNH domains. The one or more mutations can render the one or more catalytic domains of Cas9 inactive. The one or more mutations can reduce the catalytic activity of Cas 9 0.1-fold, fold, 0.5 fold, 0.75 fold, 1 fold, 2 fold, 5 fold, 10 fold, 50 fold, 100 fold, or 1000 fold. In some cases, the one or more mutations can increase the catalytic activity of Cas9 0.1-fold, 0.25 fold, 0.5 fold, 0.75 fold, 1 fold, 2 fold, 5 fold, 10 fold, 50 fold, 100 fold, or 1000 fold.

E. RNA Aptamer for Delivery of CRISPR Polynucleotides to Cells

The CRISPR polynucleotide can be modified with a cell penetrating RNA aptamer. The cell penetrating RNA aptamer can improve the effective delivery of the CRISPR polynucleotide to a cell. The RNA aptamer can bind to a cell surface receptor and promote the entry of CRISPR polynucleotide into a cell. The cell penetrating aptamer can be designed to target a specific cell receptor in order to mediate cell-specific delivery.

F. Multiple CRISPR Complexes

In some cases, a system comprises one or more CRISPR complexes provided herein. A first and second (or more) CRISPR complexes can be used in an in vitro or in vivo method. The CRISPR effector proteins (e.g., CRISPR enzymes) in the first and second (and more) CRISPR complexes can be the same or different. In one example, an in vitro or in vivo system can comprise a plurality of CRISPR polynucleotides with different guide sequences and the same CRISPR effector protein (e.g., Cas9). In another example, an in vitro or in vivo system can comprise a CRISPR polynucleotide and a plurality of different CRISPR effector proteins (e.g., a mix of catalytically active and catalytically inactive CRISPR effector proteins).

G. Multiple CRISPR Polynucleotides, e.g., in a Cell

An in vitro system or an in vivo system, e.g., a host cell, can comprise two or more (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 6, 87, 88, 89, 90, 91, 92, 93, 94, 95, 96, 97, 98, 99 or 100) different CRISPR polynucleotides, wherein the nucleotide sequences of the guide sequence of the different CRISPR polynucleotides are independently fully or partially complementary to regions of two or more different target nucleic acids (e.g., DNAs). Multiple CRISPR polynucleotides (e.g. 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 6, 87, 88, 89, 90, 91, 92, 93, 94, 95, 96, 97, 98, 99 or 100 different CRISPR polynucleotides) can be used to cleave target sequences in one or more cell types simultaneously or non-simultaneously. The different CRISPR polynucleotides can have different relative positions of one or more cleavage elements, or the same relative positions of the one or more cleavage elements.

VIII. Expression of CRISPR Complex Components

In some cases, a CRISPR effector protein and/or a CRISPR polynucleotide provided herein can be expressed from a nucleic acid.

A. Expression of CRISPR Effector Protein and/or CRISPR Polynucleotide

In some cases, one or more expression vectors for expressing CRISPR polynucleotide and CRISPR effector protein (e.g., CRISPR enzyme) can be transfected into a host cells. The expression vector comprising a DNA sequence coding for the CRISPR polynucleotide can be transfected into the host cell first and then an expression vector comprising a DNA sequence coding for the CRISPR effector protein (e.g., CRISPR enzyme) can be transfected into the host cell. The expression vector comprising a DNA sequence coding for the CRISPR effector protein (e.g., CRISPR enzyme) and an expression vector comprising a DNA sequence coding for the inducible CRISPR polynucleotide can be transfected simultaneously into the host cell. A single (type of) expression vector comprising a DNA sequence coding for the CRISPR effector protein (e.g., CRISPR enzyme) and a DNA sequence coding for the inducible CRISPR polynucleotide can be transfected into the host cell. The host cell can be a host cell which endogenously expresses the CRISPR effector protein (e.g., CRISPR enzyme). A messenger RNA encoding the CRISPR effector protein (e.g., CRISPR enzyme) can also be used with a CRISPR polynucleotide, e.g., a sgRNA for gene editing. When a vector is used, it can contain an inducible promoter. Conditional promoter(s) and/or inducible promoter(s) and/or tissue specific promoter(s) can be RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. In some cases, a transgene encoding a CRISPR effector protein (e.g., CRISPR enzyme) can be integrated into a genome of cell.

A transgene expressing the CRISPR effector protein (e.g., CRISPR enzyme) can be introduced in a cell. A CRISPR effector protein (e.g., CRISPR enzyme, e.g., Cas9) transgene can be introduced into an isolated cell. A CRISPR complex transgenic cell can be obtained by isolating cells from a transgenic organism. A CRISPR effector protein (e.g., CRISPR enzyme, e.g., Cas9) transgene can be delivered to a eukaryotic cell by means of vector (e.g., AAV, adenovirus, lentivirus) and/or particle and/or nanoparticle delivery, as also described herein.

B. Inducible Expression of CRISPR Polynucleotide and/or CRISPR Effector Protein

In some cases, the CRISPR polynucleotide can be inducibly expressed. In some cases, the CRISPR effector protein (e.g., CRISPR enzyme) can be inducibly expressed. Inducing expression of the CRISPR polynucleotide and/or CRISPR effector protein (e.g., CRISPR enzyme) can result in formation of a CRISPR polynucleotide/CRISPR effector protein (e.g., CRISPR enzyme) complex that can be turned "on" at a desired time to target a target nucleic acid (e.g., target DNA) and to cleave that target nucleic acid (e.g., target DNA). The inducible complexes can be used to reduce off-target effects by limiting the active half-life of the complex or by achieving tissue-specific editing in model organisms or in human cells. The inducible complexes can be used to remove off-target effects, by optimizing duration of activity before exposure to cell-independent stimulus, as measured by deep sequencing. The inducible complexes can be used to obtain a maximized ratio of on:off-target editing efficiency, by optimizing the duration of activity before exposure to cell-independent stimulus, inducible tissue-specific editing can be used to observe phenotypic differences between edited and un-edited regions of the targeted tissues.

The inducible CRISPR polynucleotide and/or CRISPR effector protein (e.g., CRISPR enzyme) can be expressed within a host cell. The expression may be in any order.

IX. Applications

The CRISPR polynucleotides and CRISPR complexes described herein can be used in vitro or in vivo to cause a change in a cell or an organism. The CRISRP polynucleotide and CRISPR effector protein can be introduced as a complex or they can form a complex within the cell. The CRISPR polynucleotide and/or CRISPR effector protein can be passively introduced to a cell or introduced through a vehicle. The CRISPR polynucleotide and the CRISPR effector protein can be present in a buffer at the time of introduction.

In some cases, masks can be created to go over a cell culture. Masks can be created using a variety of techniques (laser cutting, 3D printing, photolithography, etc.). Masks can be designed to let light penetrate in a defined region. When used in conjunction with a CRISPR OFF complex comprising a photocleavable linker, editing in areas where the light (e.g., UV light) penetrates can be decreased, and editing in areas without exposure to light can be maintained. When used in conjunction with a CRISPR ON complex, editing in areas where the light (e.g., UV light) penetrates can be initiated.

Figure 14:
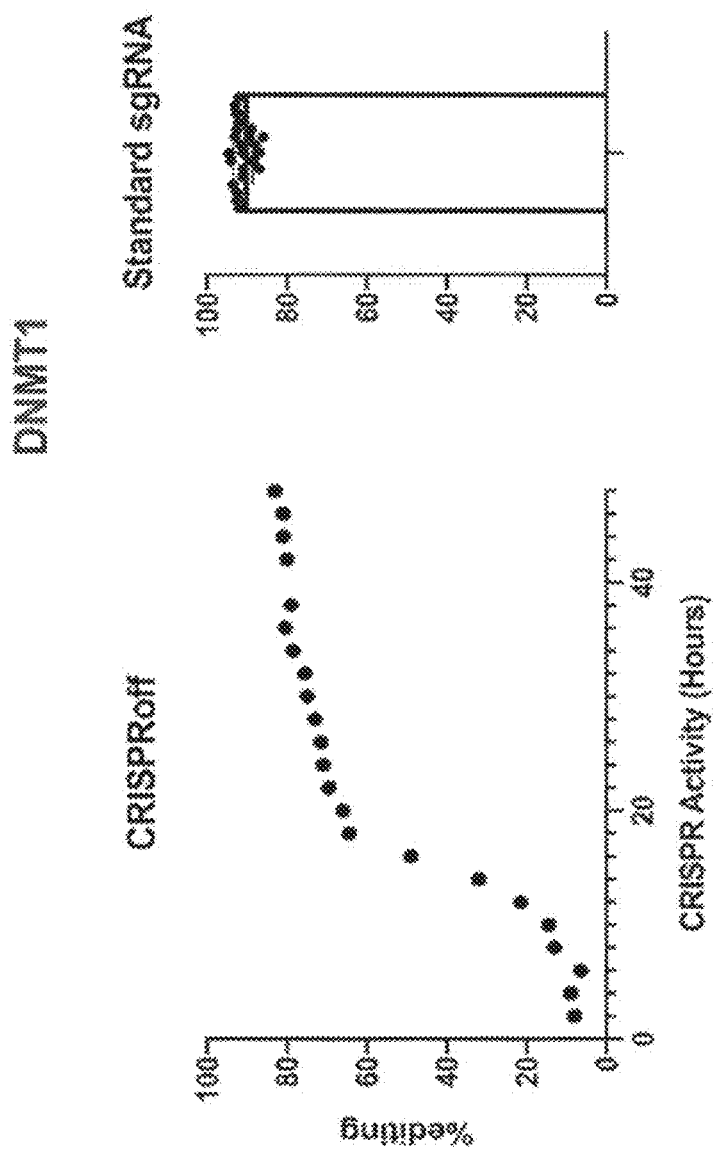
FIG. 14 shows time dependent editing activity of a CRISPR OFF complex targeting DNMT1 compared to a CRISPR complex comprising a standard sgRNA targeting DNMT1.
Figure 15:
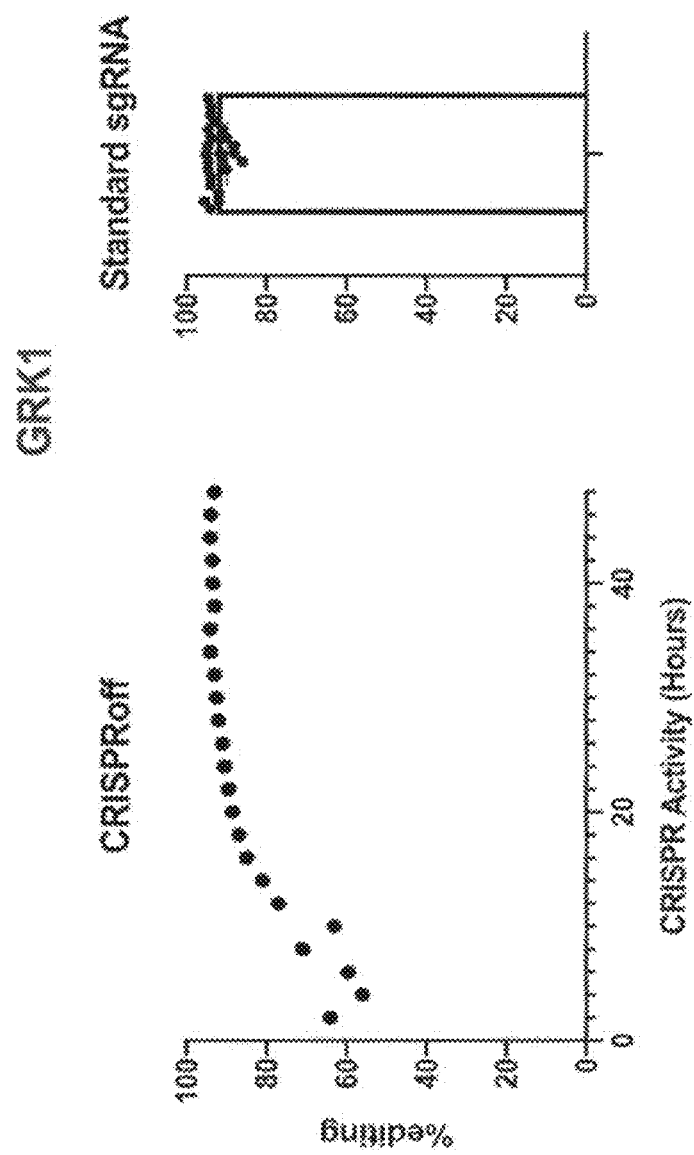
FIG. 15 shows time dependent editing activity of a CRISPR OFF complex targeting GRK1 compared to a CRISPR complex comprising a standard sgRNA targeting GRK1.
Figure 16:
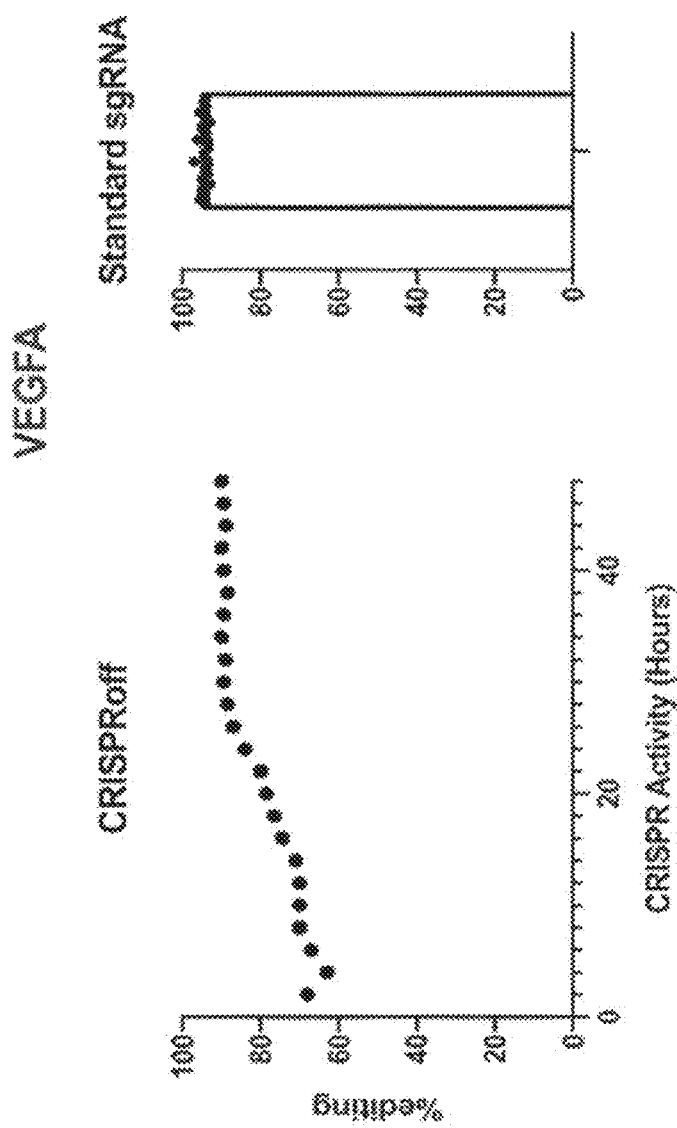
FIG. 16 shows time dependent editing activity of a CRISPR OFF complex targeting VEGFA compared to a CRISPR complex comprising a standard sgRNA targeting VEGFA.

In some cases, a CRISPR OFF complex activity can be time-dependent (e.g., as can be seen in Example 8, FIGS. 14-16). Cells can be exposed to a cleavage activator, such as UV light, at a time point prior to complete editing, resulting in a heterozygous clone. Alternatively, such a method can be used to target a diseased allele of a patient-derived cell line.

A. Nucleic Acid Editing

CRISPR complexes described herein can induce one or more mutations in a eukaryotic cell. The one or more mutations can include the introduction, deletion, or substitution of one or more nucleotides at each target sequence of cells via CRISPR polynucleotides (e.g., the guides RNAs or sgRNAs). The one or more mutations can be introduction, deletion, or substitution of about 1 to about 75 nucleotides at each target sequence of said cells. The one or more mutations can be the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell. The target sequence can be a gene and can include BUB1B, CAMK1, PRKAG3, STK3, CAMK1, Chr8q23, CEL, IRAK4, DNMT1, EMX1, FANCF, GRK1, PRGN, AAVS1, BUB1B, CXCR4, FAM163A, GAA, CRK1, IRAK4, MAPRE1, MIP, OMP, OPN1SW, PRKAG3, STK3, and VEGFA and VEGFA. (for example, as can be seen in Examples 5, 6, 9, 11 and 12)

The nucleic acid editing can target an endogenous regulatory control element (e.g., enhancer or silencer). The nucleic acid editing can target a promoter or promoter-proximal elements. These control elements can be located upstream or downstream of the transcriptional start site (TSS), starting from 200 bp from the TSS to 100 kb away. Targeting of known control elements can be used to activate or repress a gene of interest. A single control element can influence the transcription of multiple target genes. Targeting of a single control element can therefore be used to control the transcription of multiple genes simultaneously.

1. CRISPR ON Mechanism for Nucleic Acid Editing

In some cases, once the ON CRISPR polynucleotide and CRISPR effector protein are within a cell, a CRISPR complex can be formed. The CRISPR ON polynucleotide can comprise a polynucleotide leader sequence separated from a guide sequence by a photocleavable element. The cell can be exposed to UV radiation, resulting in cleavage of the cleavage element and release of the polynucleotide leader sequence. The CRISPR complex can then cleave target sequence. In some cases, a donor nucleic acid is also introduced into the cell, which can be used in homologous recombination at the cleavage site to introduce an edit to the nucleic acid.

2. CRISPR ON/OFF Mechanism for Nucleic Acid Editing

In some cases, the tunable modulation of the editing of a target gene in a target DNA in a host cell comprises the steps: (i) using viral or non-viral delivery methods or a combination thereof, described herein or known in the art, to introduce into the host cell: (a) a CRISPR polynucleotide comprising first and second cleavage elements, where the cleavage elements are susceptible to cleavage and where the nucleotide sequence of the guide sequence is fully or partially complementary to a target nucleic acid sequence, wherein the first cleavage element is position between a polynucleotide leader sequence and a 5' end of a guide sequence; and (b) a CRISPR effector protein (e.g., CRISPR enzyme, e.g., Cas9) with catalytic activity such that the CRISPR polynucleotide and the CRISPR enzyme form a CRISPR complex; and (ii) through exposure to UV light, inducing cleavage of the first sequence element in the polynucleotide, thereby releasing the polynucleotide leader sequence and activating higher target specific cleavage of the target gene by the CRISPR complex. Subsequently, the method can comprise (iii) inducing cleavage of the second sequence element, which can be located in scaffold sequence of the CRISPR polynucleotide, at a desired time through pulsed exposure to UV light, thereby cleaving the CRISPR polynucleotide and deactivating or lowering the target specific cleavage of the target gene by the CRISPR complex.

B. Gene Regulation

A CRISPR ON/OFF polynucleotide can be complexed with a CRISPR effector protein, which can be a catalytically dead Cas9. The catalytically dead Cas9 can be fused to a transcription activation domain (e.g., VP64). The fusion, e.g., Cas9-VP64 fusion, and can be used to tunably modulate the expression of a target gene or a chromatin region. For example, the polynucleotide leader sequence of the CRISPR ON/OFF polynucleotide can prevent efficient localization of the CRISPR complex to target gene via the guide sequence. Cleavage of the polynucleotide leader sequence can result in efficient targeting of the CRISPR complex to the target sequence via the guide sequence, which can result in transcriptional activation. Subsequently, a second cleavage agent can be exposed to the CRISPR polynucleotide that results in cleavage of the CRISPR polynucleotide and reduces or inhibits the ability of the CRISPR complex (or CRISPR effector protein, if the cleaved CRISPR polynucleotide has dissociated from the CRISPR effector protein) to activate transcription of the gene.

Targeting of regions with either an activation or repression system described herein can be followed by readout of transcription of either a) a set of putative targets (e.g., a set of genes located in closest proximity to the control element) or b) whole-transcriptome readout by e.g. RNAseq or microarray.

In another example, CRISPR complexes provided herein can be used to study the epistatic interactions of two or more target genes in the host cell. A method can comprise of the steps: (i) using viral or non-viral delivery methods or a combination thereof, introducing into the host cell: (a) a CRISPR polynucleotide comprising first and second cleavage elements, where the cleavage elements are susceptible to cleavage and where the nucleotide sequence of the guide sequence is fully or partially complementary to a first target nucleic acid sequence; (b) a CRISPR effector protein (e.g., CRISPR) enzyme with catalytic activity, such that the CRISPR polynucleotide (e.g., sgRNA) and the CRISPR enzyme form a CRISPR complex; and (ii) at the desired time, inducing the cleavage of the first cleavage element in the CRISPR polynucleotide and activating higher target specific cleavage of the target gene by the CRISPR complex and then (iii) inducing cleavage of the second cleavage element at a desired time, thereby deactivating or lowering the target specific cleavage of the target gene by the CRISPR complex.

The method can further comprise (i) using viral or non-viral delivery methods or a combination thereof to introduce into the host cell: (a) a second CRISPR polynucleotide comprising of the first and second cleavage elements, where the cleavage elements are susceptible to cleavage and where the nucleotide sequence of the guide sequence is fully or partially complementary to a region of a second target sequence (e.g., in a target gene); (b) a CRISPR enzyme with catalytic activity, such that the second CRISPR polynucleotide (e.g., sgRNA) and the CRISPR enzyme form a second CRISPR complex; and (ii) at the desired time, inducing the cleavage of the first cleavage element in the second CRISPR polynucleotide and activating higher target specific cleavage of the target gene by the CRISPR complex and then (iii) inducing cleavage of the second cleavage element at a desired time, thereby deactivating or lowering the target specific cleavage of the target gene by the second CRISPR complex.

Furthermore, the cleavage of the first cleavage element in the first and second CRISPR complex can be under control of a tissue specific promoter, e.g., a muscle specific promoter. For example, expression of genetically engineered endoribonuclease Cas6a/Csy4 in the cell can be placed under the control of a tissue-specific promoter (e.g., muscle) promoter that can be activated at given times to induce cleavage of the first cleavage element. The second cleavage element in the first and second CRISPR complex can be inducibly cleaved at a desired time by exposure to a given sequence-specific small molecule. The CRISPR enzyme can be a dCas9-fused with a domain with transcriptional activator or repressor activity and can be used to study the epistatic interactions between a given pair of genes in a specific tissue.

In another example, CRISPR complexes described herein can be used to induce orthogonal transcription of two or more target genes in one or more target DNAs in a host cell. The term "orthogonal" can mean independent, i.e., the two or more target genes can be independently regulated or independently transcribed. The method can comprise the steps of using viral or non-viral delivery methods or a combination thereof for introducing into the host cell: (a) two or more different inducible CRISPR polynucleotides comprising of first and second cleavage elements, where the first and second sequence elements are susceptible to cleavage and where the nucleotide sequence of the guide sequence is fully or partially complementary to one or more target DNAs in the vicinity of the two or more different target genes; (b) a catalytically-inactive CRISPR enzyme linked to a transcriptional activator domain, such that the different inducible CRISPR polynucleotides and the CRISPR enzyme form different CRISPR complexes, wherein the CRISPR complexes comprise one or more effector domains; and (ii) at the desired times, inducing the cleavage of the first cleavage element in the first and second polynucleotide and thus coordinating the expression of the target genes. The target DNAs can be adjacent regions within a single gene or control element.

X. Kits

A kit can comprise one or more of the components described herein. The kit can comprise a CRISPR polynucleotide described herein. The kit can comprise a CRISPR effector protein (e.g., a CRISPR enzyme, e.g., Cas9) described herein. The kit can comprise a CRISPR complex described herein comprising a CRISPR polynucleotide described herein and a CRISPR effector protein described herein. The kit can comprise a linker, for example a cleavable linker. The kit can comprise a photocleavable linker. The kit can comprise instructions. The kit can comprise a cell or organism comprising a CRISPR polynucleotide, CRISPR effector protein, or CRISPR complex described herein.

The kit comprises a genetic construct, e.g., vector system for expressing one or more CRISPR polynucleotides and/or one or more CRISPR effector proteins and instructions for using the kit. The kit can comprise a cell that comprises one or more genetic constructs (e.g., one or more vector systems) for expressing a CRISPR polynucleotide and/or CRISPR effector protein described herein.

The kit can comprise an excipient to generate a composition suitable for contacting a nucleic acid target with e.g., a CRISPR complex described herein. The composition can be suitable for contacting a nucleic acid target sequence within a genome. The composition can be suitable for delivering the composition (e.g., a CRISPR polynucleotide, e.g., a sgRNA, e.g., complexed with a CRISPR effector protein, e.g., a CRISPR enzyme, e.g. Cas9) to a cell. The composition can be suitable for delivering a CRISPR polynucleotide, e.g., a gRNA, or complexes thereof with CRISPR enzyme) to a subject. The excipient can be a pharmaceutically acceptable excipient.

The kit can comprise one or more reagents for use in cleaving one or more of the cleavable elements of the CRISPR polynucleotides described herein. The one or more reagents can be provided in any suitable container. The kit can comprise one or more reaction or storage buffers. The kit can comprise a reagent. The reagent can be provided in a form that is usable in a particular assay, or in a form that requires addition of one or more other components before use (e.g. in concentrate or lyophilized form). A reaction or storage buffer can be any buffer, e.g., sodium carbonate buffer, a sodium bicarbonate buffer, a borate buffer, a Tris buffer, a MOPS buffer, a HEPES buffer, or a combination thereof. The buffer can have a pH from about 7 to about 10.

The kit can comprise one or more polynucleotides corresponding to a guide sequence for insertion into a vector so as to operably link the guide sequence and a regulatory element. The kit can comprise a homologous recombination template polynucleotide.

XI. CRISPR Polynucleotide Synthesis

A CRISPR polynucleotide, for example the CRISPR ON polynucleotide, CRISPR OFF polynucleotide, or CRISPR ON/OFF polynucleotide can be synthesized by any method known to one of ordinary skill in the art. The CRISPR ON polynucleotide, CRISPR OFF polynucleotide, or CRISPR ON/OFF polynucleotide can be chemically synthesized. The CRISPR ON polynucleotide, CRISPR OFF polynucleotide, or CRISPR ON/OFF polynucleotide can be synthesized using 2'-0-thionocarbamate-protected nucleoside phosphoramidites. Methods of synthesis of polynucleotides are described in, e.g., Dellinger et al., J. American Chemical Society 133, 11540-11556 (2011); Threlfall et al., Organic & Biomolecular Chemistry 10, 746-754 (2012); and Dellinger et al, J. American Chemical Society 125, 940-950 (2003). Any of the modifications described herein can be combined and incorporate a CRISPR polynucleotide, for example CRISPR ON polynucleotide, CRISPR OFF polynucleotide, or CRISPR ON/OFF polynucleotide, for example, in the guide sequence and/or the sequence that binds a CRISPR effector protein (e.g., scaffold sequence). Alternatively, the CRISPR polynucleotides can be prepared by the phosphoramidite method described by Beaucage and Caruthers (Tetrahedron Lett., (1981) 22:1859-1862), or by the triester method according to Matteucci, et al., (J. Am. Chem. Soc, (1981) 103:3185), each of which is specifically incorporated herein by reference, or by other chemical methods using a commercial automated polynucleotide synthesizer.

The CRISPR polynucleotides can be chemically synthesized, e.g., according to the solid phase phosphoramidite triester method first described by Beaucage and Caruthers, Tetrahedron Lett. 22: 1859-1862 (1981), using an automated synthesizer, as described in Van Devanter et. al, Nucleic Acids Res. 12:6159-6168 (1984). Synthesis of the CRISPR polynucleotides can comprise introducing chemical modifications that employ special phosphoramidite reagents during solid phase synthesis.

A. sgRNA Linkage

A CRISPR polynucleotide that is a sgRNA can comprise a modified crRNA and tracrRNA sequence chemically linked or conjugated via a non-phosphodiester bond. The modified crRNA and tracrRNA sequence can be chemically linked or conjugated via a non-nucleotide loop. The modified crRNA and tracrRNA can be joined via a non-phosphodiester covalent linker. The covalent linker can be a chemical moiety selected from the group consisting of coumarin, carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

B. Cleavable Elements

The cleavable elements in the CRISPR polynucleotide herein can be provided with functional groups at each end that can be suitably protected or activated. The functional groups can be covalently attached via an ether, ester, carbamate, phosphate ester or amine linkage. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. Other methods of forming ether, carbamate or amine linkages are known to those of skill in the art and particular reagents and references can be found in such texts as March, Advanced Organic Chemistry, 4th Ed., Wiley-Interscience, New York, N.Y., 1992.

C. sgRNA Synthesis

The sgRNA comprising crRNA and tracrRNA can first be synthesized using a phosphoramidite synthetic protocol (Herdewijn, P., ed., Methods in Molecular Biology Col 288, Polynucleotide Synthesis: Methods and Applications, Humana Press, New Jersey (2012)). The sgRNA comprising crRNA and tracrRNA sequences can be functionalized to contain an appropriate functional group for ligation (see e.g., Hermanson, G. T., Bioconjugate Techniques, Academic Press (2013)). The functional group can be hydroxyl, amine, carboxylic acid, carboxylic acid halide, carboxylic acid active ester, aldehyde, carbonyl, chlorocarbonyl, coumarin, psoralen, diazirine, or azide. Once the modified tracr and the tracr mate sequences are functionalized, a covalent chemical bond or linkage can be formed between the two polynucleotides. The chemical bonds can be based on coumarin, carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

The sgRNA comprising crRNA and tracrRNA sequence and can be chemically synthesized. The sgRNA can be synthesized together in the form of a fusion or synthesized separately and chemically linked. The chemical synthesis can use automated using solid-phase polynucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

The sgRNA can be covalently linked with various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Polynucleotides (2008) 18: 305-19; Watts, et al., Drug. Discov. Today (2008) 13: 842-55; Shukla, et al., ChemMedChem (2010) 5: 328-49.

The sgRNA can be assembled using click chemistry. The crRNA tracrRNA and/or the sequence elements therein can be assembled by covalent linkage using a triazole linker. The sgRNA can be covalently linked by ligating a 5'-hexyne tracrRNA and a 3'-azide crRNA. Either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

XII. Administering CRISPR Polynucleotide to a Cell

Viral and non-viral mediated techniques can be used to introduce a CRISPR polynucleotide into a cell. The non-viral mediated techniques can be electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

A CRISPR polynucleotide, for example the CRISPR ON polynucleotide, CRISPR OFF polynucleotide, or CRISPR ON/OFF polynucleotide and related vectors can be delivered to a cell naked (i.e. free from agents which promote transfection). The naked CRISPR polynucleotides can be delivered to the cell using routes of administration known in the art and described herein.

XIII. Pharmaceutical Compositions: Formulation, Administration, Delivery and Dosing A CRISPR polynucleotide, for example the CRISPR ON polynucleotide, CRISPR OFF polynucleotide, or CRISPR ON/OFF polynucleotide, described herein, can be formulated in pharmaceutical compositions comprising one or more pharmaceutically acceptable excipients. The pharmaceutical compositions can comprise one or more additional active substances, e.g., therapeutically and/or prophylactically active substances. General considerations in the formulation and/or manufacture of pharmaceutical compositions can be found, for example, in Remington: The Science and Practice of Pharmacy 2 ed., Lippincott Williams & Wilkins, 2005 (incorporated herein by reference in its entirety).

A CRISPR polynucleotide, for example the CRISPR ON polynucleotide, CRISPR OFF polynucleotide, or CRISPR ON/OFF polynucleotide, described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide, primary construct, or mRNA to specific tissues or cell types); (5) increase the translation of encoded protein in vivo; and/or (6) alter the release profile of encoded protein in vivo.

The excipients can be solvents, dispersion media, diluents, or other liquid vehicles, dispersion or suspension aids, surface active agents, isotonic agents, thickening or emulsifying agents, preservatives, and/or emulsifiers, preservatives, buffering agents, lubricating agents, and/or oils. The excipients can be lipidoids, liposomes, lipid nanoparticles, polymers, lipoplexes, core-shell nanoparticles, peptides, proteins, cells transfected with polynucleotide, primary construct, or Cas nuclease mRNA (e.g., for transplantation into a subject), hyaluronidase, nanoparticle mimics and combinations thereof.

Relative amounts CRISPR polynucleotide, CRISPR effector protein, or nucleic acid encoding either, and the pharmaceutically acceptable excipient, and/or any additional ingredients in a pharmaceutical composition can vary, depending upon the identity, size, and/or condition of the subject treated and further depending upon the route by which the composition is to be administered. The composition can comprise between 0.1% and 100%, e.g., between 0.5 and 50%, between 1-30%, between 5-80%, at least 80% (w/w) CRISPR polynucleotide, CRISPR effector protein, or nucleic acid encoding either.

The synthesis of lipidoids has been extensively described and formulations containing these compounds are particularly suited for delivery of the modified CRISPR ON polynucleotide, CRISPR OFF polynucleotide, or CRISPR ON/OFF polynucleotide, described herein, and primary constructs (see Mahon et al., Bioconjug Chem. 2010 21:1448-1454; Schroeder et al., J Intern Med. 2010 267:9-21; Akinc et al, Nat Biotechnol. 2008 26:561-569; Love et al, Proc Natl Acad Sci USA. 2010 107: 1864-1869; Siegwart et al., Proc Natl Acad Sci USA. 201 1 108: 12996-3001; all of which are incorporated herein in their entireties). Different ratios of lipidoids and other components including, but not limited to, disteroylphosphatidyl choline, cholesterol and PEG-DMG, may be used to optimize the formulation of the polynucleotide, primary construct, or Cas nuclease mRNA for delivery to different cell types including, but not limited to, hepatocytes, myeloid cells, muscle cells, etc.

A CRISPR polynucleotide, for example the CRISPR ON polynucleotide, CRISPR OFF polynucleotide, or CRISPR ON/OFF polynucleotide, described herein, can be formulated using one or more liposomes, lipoplexes, or lipid nanoparticles (LNP). The pharmaceutical compositions can include liposomes. The pharmaceutical compositions described herein can include liposomes such as those formed from the synthesis of stabilized plasmid-lipid particles (SPLP) or stabilized nucleic acid lipid particle (SNALP) that have been previously described and shown to be suitable for polynucleotide delivery in vitro and in vivo (see Wheeler et al. Gene Therapy. 1999 6:271-281; Zhang et al. Gene Therapy. 1999 6: 1438-1447; Jeffs et al. Pharm Res. 2005 22:362-372; Morrissey et al, Nat Biotechnol. 2005 2: 1002-1007). The CRISPR polynucleotides may be formulated in a lipid vesicle which can have crosslinks between functionalized lipid bilayers.

A CRISPR polynucleotide, for example the CRISPR ON polynucleotide, CRISPR OFF polynucleotide, or CRISPR ON/OFF polynucleotide, described herein can be formulated in a lipid-polycation complex. The formation of the lipid-polycation complex can be accomplished by methods known in the art and/or as described in U.S. Pub. No. 20120178702, herein incorporated by reference in its entirety. The pharmaceutical composition can include at least one of the PEGylated lipids described in International Publication No. 2012099755, herein incorporated by reference.

The LNP formulation can be formulated by the methods described in International Publication Nos. WO2011 127255 or WO2008 103276, each of which is herein incorporated by reference in their entirety. The CRISPR polynucleotide can be encapsulated in LNP formulations as described in WO2011 127255 and/or WO2008103276; each of which is herein incorporated by reference in their entirety.

A CRISPR polynucleotide, for example the CRISPR ON polynucleotide, CRISPR OFF polynucleotide, or CRISPR ON/OFF polynucleotide, described herein, can formulated as a solid lipid nanoparticle. A solid lipid nanoparticle (SLN) can be spherical with an average diameter between 10 to 1000 nm. SLN can possess a solid lipid core matrix that can solubilize lipophilic molecules and can be stabilized with surfactants and/or emulsifiers. The lipid nanoparticle can be a self-assembly lipid-polymer nanoparticle (see Zhang et al, ACS Nano, 2008, 2 (8), pp 1696-1702; herein incorporated by reference in its entirety).

A CRISPR polynucleotide, for example the CRISPR ON polynucleotide, CRISPR OFF polynucleotide, or CRISPR ON/OFF polynucleotide, described herein, primary constructs, or the Cas nuclease mRNA can be encapsulated into a lipid nanoparticle or a rapidly eliminating lipid nanoparticle and the lipid nanoparticles or a rapidly eliminating lipid nanoparticle can then be encapsulated into a polymer, hydrogel and/or surgical sealant described herein and/or known in the art.

A CRISPR polynucleotide, for example the CRISPR ON polynucleotide, CRISPR OFF polynucleotide, or CRISPR ON/OFF polynucleotide, described herein, formulation for controlled release and/or targeted delivery can also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, The controlled release and/or targeted delivery formulation can comprise at least one degradable polyester which can contain polycationic side chains. The degradable polyester can be poly(serine ester), poly(L-lactide-co-L-lysine), poly(4-hydroxy-L-proline ester), and combinations thereof. The degradable polyesters can include a PEG conjugation to form a PEGylated polymer.

A CRISPR polynucleotide, for example the CRISPR ON polynucleotide, CRISPR OFF polynucleotide, or CRISPR ON/OFF polynucleotide can be encapsulated in a therapeutic nanoparticle. The therapeutic nanoparticle can be formulated for sustained release. The period of time can include hours, days, weeks, months and years. As a non-limiting example, the sustained release nanoparticle can comprise a polymer and a therapeutic agent, e.g., CRISPR polynucleotides described herein (see International Pub No. 2010075072 and US Pub No. US20100216804 and US20110217377, each of which is herein incorporated by reference in their entirety. The therapeutic nanoparticles can be formulated to be target specific. The therapeutic nanoparticles can include a corticosteroid (see International Pub. No. WO2011084518).

A CRISPR polynucleotide, for example the CRISPR ON polynucleotide, CRISPR OFF polynucleotide, or CRISPR ON/OFF polynucleotide, described herein, can be encapsulated in, linked to and/or associated with synthetic nanocarriers. The synthetic nanocarriers can be formulated by the methods described in International Pub Nos. WO2010005740, WO2010030763. The synthetic nanocarriers can contain reactive groups to release the CRISPR polynucleotides, described herein (see International Pub. No. WO20120952552 and US Pub No. US20120171229, each of which is herein incorporated by reference in their entirety).

The synthetic nanocarriers can be formulated for targeted release. The synthetic nanocarrier can be formulated to release the CRISPR polynucleotides at a specified pH and/or after a desired time interval. The synthetic nanoparticle can be formulated to release the polynucleotides, primary constructs and/or Cas nuclease mRNA after 24 hours and/or at a pH of 4.5 (see International Pub. Nos. WO2010138193 and WO2010138194 and US Pub Nos. US201 10020388 and US20110027217, each of which is herein incorporated by reference in their entireties).

The synthetic nanocarriers can be formulated for controlled and/or sustained release of the CRISPR polynucleotides described herein. The synthetic nanocarriers for sustained release can be formulated, e.g., as described herein and/or as described in International Pub No. WO2010138192 and US Pub No. 20100303850, each of which is herein incorporated by reference in their entireties.

A CRISPR polynucleotide, for example the CRISPR ON polynucleotide, CRISPR OFF polynucleotide, or CRISPR ON/OFF polynucleotide, described herein, can be formulated with or in a polymeric compound. The polymer can include at least one polymer polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, biodegradable block copolymer, biodegradable random copolymer, biodegradable polyester copolymer, biodegradable polyester block copolymer, biodegradable polyester block random copolymer, linear biodegradable copolymer, poly[a-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers or combinations thereof.

A CRISPR polynucleotide, for example the CRISPR ON polynucleotide, CRISPR OFF polynucleotide, or CRISPR ON/OFF polynucleotide, described herein, can be conjugated with another compound. The CRISPR polynucleotide can also be formulated as a nanoparticle using a combination of polymers, lipids, and/or other biodegradable agents, e.g., calcium phosphate. Components can be combined in a core-shell, hybrid, and/or layer-by-layer architecture, to allow for fine-tuning of the nanoparticle so the delivery of the CRISPR polynucleotide can be enhanced (Wang et al, Nat Mater. 2006 5:791-796; Fuller et al, Biomaterials. 2008 29: 1526-1532; DeKoker et al, Adv Drug Deliv Rev. 201 1 63:748-761; Endres et al., Biomaterials. 2011 32:7721-7731; Su et al., Mol Pharm. 2011 Jun. 6; 8(3):774-87; herein incorporated by reference in its entirety).

A CRISPR polynucleotide, for example the CRISPR ON polynucleotide, CRISPR OFF polynucleotide, or CRISPR ON/OFF polynucleotide, described herein, can be formulated with peptides and/or proteins in order to increase transfection of cells by the CRISPR polynucleotide. The peptides can be cell penetrating peptides and proteins and peptides that enable intracellular delivery can be used to deliver pharmaceutical formulations.

A CRISPR polynucleotide, for example the CRISPR ON polynucleotide, CRISPR OFF polynucleotide, or CRISPR ON/OFF polynucleotide, described herein, can be transfected ex vivo into cells, and subsequently transplanted into a subject. Examples of such vectors include primary nucleic acid constructs or synthetic sequences encoding CRISPR effector proteins or related polypeptides. The pharmaceutical compositions can include red blood cells to deliver modified RNA to liver and myeloid cells, virosomes to deliver modified RNA in virus-like particles (VLPs), and electroporated cells e.g., from MAXCYTE® (Gaithersburg, MD) and from ERYTECH® (Lyon, France) to deliver modified RNA.

Cell-based formulations of a CRISPR polynucleotide, for example the CRISPR ON polynucleotide, CRISPR OFF polynucleotide, or CRISPR ON/OFF polynucleotide, described herein, or related vector constructs can be used to ensure cell transfection (e.g., in the cellular carrier), alter the biodistribution of the CRISPR polynucleotide (e.g., by targeting the cell carrier to specific tissues or cell types), and/or increase the translation of encoded protein.

The compositions can also be formulated for direct delivery to an organ or tissue by, e.g., direct soaking or bathing, via a catheter, by gels, powder, ointments, creams, gels, lotions, and/or drops, by using substrates such as fabric or biodegradable materials coated or impregnated with the compositions, and the like.

A CRISPR polynucleotide, for example the CRISPR ON polynucleotide, CRISPR OFF polynucleotide, or CRISPR ON/OFF polynucleotide, described herein, and related sequences/polypeptides can be administered by any route which results in a therapeutically effective outcome. These include enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. Compositions can be administered in a way which allows them to cross the blood-brain barrier, vascular barrier, or other epithelial barrier.

A CRISPR polynucleotide, for example the CRISPR ON polynucleotide, CRISPR OFF polynucleotide, or CRISPR ON/OFF polynucleotide, described herein, can be used in a number of different scenarios in which delivery of a substance (the "payload") to a biological target is desired, for example delivery of detectable substances for detection of the target, or delivery of a therapeutic agent. The CRISPR polynucleotides and related vector constructs can be used in combination with one or more other therapeutic, prophylactic, diagnostic, or imaging agents.

A CRISPR polynucleotide, for example the CRISPR ON polynucleotide, CRISPR OFF polynucleotide, or CRISPR ON/OFF polynucleotide, described herein, and other primary constructs can be designed to include both a linker and a payload in any useful orientation. For example, a linker having two ends can be used to attach one end to the payload and the other end to the nucleobase, such as at the C-7 or C-8 positions of the deaza-adenosine or deaza-guanosine or to the N-3 or C-5 positions of cytosine or uracil. The payload can be a therapeutic agent such as a cytotoxin, radioactive ion, chemotherapeutic, or other therapeutic agent.

A CRISPR polynucleotide, for example the CRISPR ON polynucleotide, CRISPR OFF polynucleotide, or CRISPR ON/OFF polynucleotide, described herein, can be used to alter the phenotype of cells. The CRISPR polynucleotide or CRISPR effector protein encoding sequence can be used in therapeutics and/or clinical and research settings. A CRISPR polynucleotide, for example the CRISPR ON polynucleotide, CRISPR OFF polynucleotide, or CRISPR ON/OFF polynucleotide and related vector constructs and the proteins translated from them described herein can be used as therapeutic or prophylactic agents. For example, a CRISPR polynucleotide or Cas nuclease mRNA described herein (e.g. a modified mRNA encoding a CRISPR-related polypeptide or effector protein) can be administered to a subject and translated in vivo to direct the expression of a therapeutically relevant or prophylactic polypeptide in the subject.

The ability of a guide sequence (within a nucleic acid-targeting guide RNA or sgRNA) to direct sequence-specific binding of a nucleic acid-targeting complex to a target nucleic acid sequence can be assessed by any suitable assay. For example, the components of a nucleic acid-targeting CRISPR system sufficient to form a nucleic acid-targeting complex, including the guide sequence to be tested, can be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence. Cleavage of a target nucleic acid sequence can be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions.

Compositions provided herein can be used for treatment of any of a variety of diseases, disorders, and/or conditions, e.g., one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Standard abbreviations may be used, e.g., bp, base pair(s); kb, kilobase(s); nt, nucleotide(s); and the like.

Example 1: Generation and Functional Characterization of Modified Polynucleotide with Photocleavable Linker Four sgRNAs were synthesized. The sequences representing a part of the sgRNAs are provided below. Modification on the sgRNAs includes 2'-O-methyl analogs and 3' phosphorothioate internucleotide linkages at the first three 5' and 3' terminal RNA nucleotides.

"Control":
(SEQ ID NO: 1)
NNNNNNNNNNNNNNNNNNNNNNNGUUUUAGAGCUAGAAAUAGCAAGUUAAAAU

AAGGCUAGUCCGUUAUCAACUUGAAAAAGUGGCACCGAGUCGGUGCUUUU

"No $2^{nd}$":
(SEQ ID NO: 2)
GAAANNNNNNNNNNNNNNNNNNNNNNGUUUUAGAGCUAGAAAUAGCAAGUUA

AAAUAAGGCUAGUCCGUUAUCAACUUGAAAAAGUGGCACCGAGUCGGUGC

UUUU

"3 bp Stem":
(SEQ ID NO: 3)
UGAGAAAUCANNNNNNNNNNNNNNNNNNNNNNGUUUUAGAGCUAGAAAUAGC

AAGUUAAAAUAAGGCUAGUCCGUUAUCAACUUGAAAAAGUGGCACCGAGU

CGGUGCUUUU

"6 bp Stem":
(SEQ ID NO: 4)
CACUGAGAAAUCAGUGNNNNNNNNNNNNNNNNNNNNNNGUUUUAGAGCUAGA

AAUAGCAAGUUAAAAUAAGGCUAGUCCGUUAUCAACUUGAAAAAGUGGCA

CCGAGUCGGUGCUUUU

The first sgRNA ("Control" or "Mods") is a sgRNA lacked a polynucleotide leader sequence 5' of the guide sequence. The second sgRNA ("No $2^{nd}$" or "No Secondary") had a polynucleotide leader sequence 5' of the guide sequence that was designed to not form a stem loop, followed by a photocleavable linker, 3-(4,4'-Dimethoxytrityl)-1-(2-nitrophenyl)-propan-1-yl-[(2-cyanoethyl)-(N,N-diisopropyl)]-phosphoramidite (www.glenresearch.com/data/ProductInfo.php?item=10-4920) inserted between the 3' end of the polynucleotide leader sequence and 5' of the guide sequence. Two additional sgRNAs were synthesized with an added polynucleotide leader sequence designed to form a stem loop before the 5' base of the guide sequence, followed by a 3-(4,4'-Dimethoxytrityl)-1-(2-nitrophenyl)-propan-1-yl-[(2-cyanoethyl)-(N,N-diisopropyl)]-phosphoramidite (http://www.glenresearch.com/data/ProductInfo.php?item=10-4920) photocleavable linker inserted between the 3' end of the added polynucleotide leader sequence and the 5' base of the guide sequence. The third sgRNA ("3 bp Stem") had a polynucleotide leader sequence designed to form a 3 bp stem loop and the fourth sgRNA ("6 bp Stem") had polynucleotide leader sequence designed to form a 6 bp stem loop. The four types of sgRNA were then exposed to the UVA light (320-390 nm) using conditions known to be sufficient for photocleaving sgRNA in vitro.

FIG. 2 is a gel image run on a fragment analyzer using the small RNA analysis kit from Advanced Analytical, depicting the four sgRNA after exposure to UV light for 0 minutes, 5 minutes, 10 minutes, or 15 minutes. All images from a set time point were run on the same gel in adjacent lanes i.e. all 10 minute samples were run next to each other. Samples from different time points were run on different gels to allow testing of multiple sgRNA target sites. Comparison between conditions was primarily based on qualitative observation. After 5 minutes of exposure to UV light the second, third, and fourth sgRNAs showed a banding pattern consistent with cleavage of the polynucleotide leader sequence. The banding patterns after 10 minutes and 15 minutes of exposure were also consistent with cleavage of the polynucleotide leader sequence from the second, third, and fourth sgRNAs.

Figure 3:
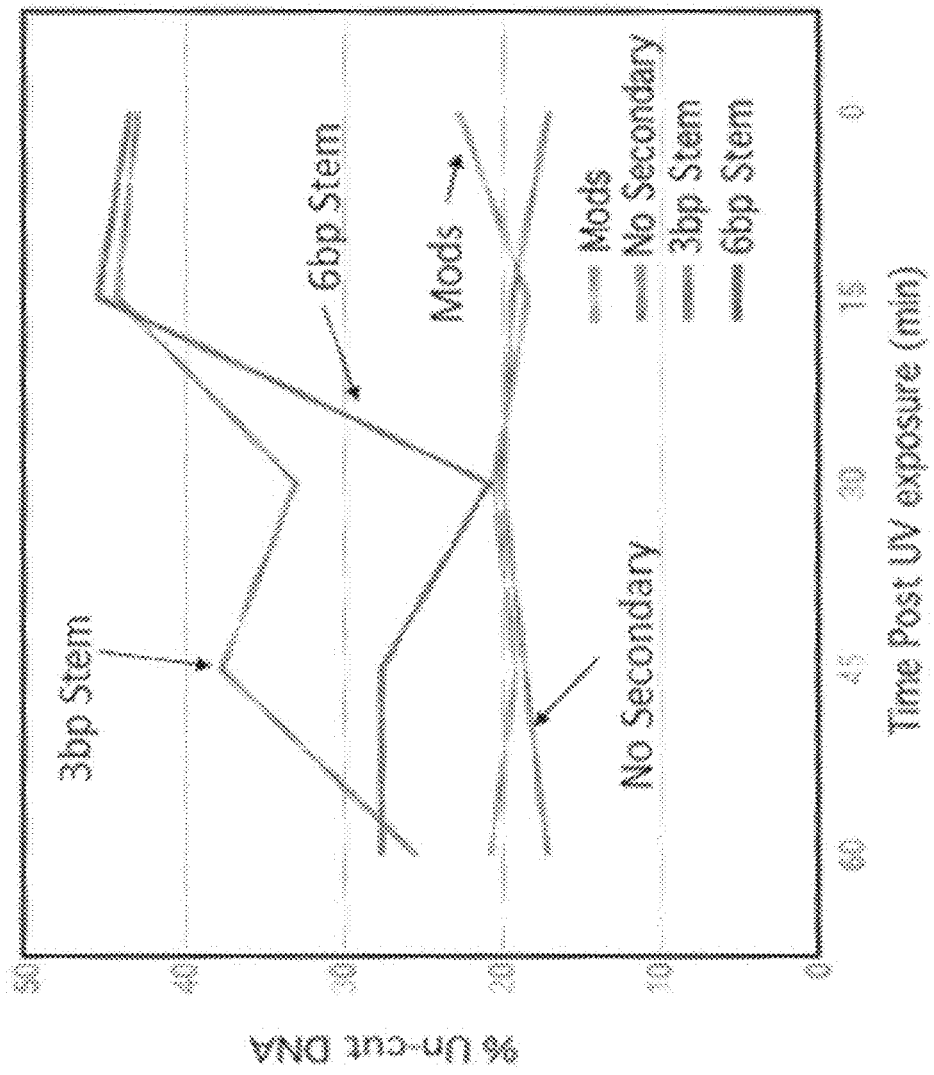
FIG. 3 shows the efficacy of in vitro CRISPR-ON sgRNA activation of target DNA cleavage. CRISPR-ON sgRNAs with 5' cleavable stem-loop were incubated with target DNA (human FANCF) for one hour and exposed to cleavage agent, UVA light (320-390 nm) at regular intervals. "Mods" is a sgRNA modified to include 2'-O-methyl analogs and 3' phosphorothioate internucleotide linkages at the first three 5' and 3' terminal RNA nucleotides, and lacking any 5' addition of bases to the guide sequence. Standard modification on sgRNAs includes. The "No Secondary" condition uses a sgRNA with a non-stem forming 5' addition to the guide sequence. The "3 bp stem" and the "6 bp stem" conditions use sgRNAs with sequences at the 5' end of the sgRNA designed to form stem regions of 3 and 6 bp, respectively.

Example 2: Characterization of Target DNA Cutting Efficiency Upon sgRNA Activation As described above, the four sgRNAs were complexed with spCas9 and incubated with target DNA for an appropriate duration in vitro. The four sgRNAs were then each exposed to UV light (320-390 nm) at 175 mW/cm$^2$ for the indicated periodic intervals, shown in FIG. 3. UV-mediated cleavage of the sgRNAs with designed stems ("3 bp Stem" and "6 bp Stem") served to activate the CRISPR complex resulting in the cutting of the target specific DNA. The target DNA was then run on a fragment analyzer to demonstrate CRISPR-mediated cutting. FIG. 3 shows an example of sgRNA-Cas9 CRISPR complex incubated with target DNA (FANCF) and exposed to the cleavage agent at regular intervals. At 0 minutes post exposure, the third and fourth sgRNAs ("3 bp Stem" and "6 bp Stem") showed decreased cutting efficiency compared to the first and second sgRNAs. After 15 min of exposure to the cleavage agent, the activated sgRNAs registered an increase in cutting efficiency of target DNA. Measurement of the ratio of uncut to cut DNA showed a decrease from ~45% at 15 minutes exposure to ~20% at 30 minutes of exposure for "6 bp Stem." In comparison, the first sgRNA lacking 5' polynucleotide leader sequence ("Mods") or a 5' secondary structure ("No Secondary") did not exhibit activation with cleavage agent, as measured by ratio of uncut to cut DNA. "Mods" is a modified synthetic sgRNA with 2'-O-methyl analogs and 3' phosphorothioate internucleotide linkages at the first three 5' and 3' terminal RNA nucleotides, lacking any 5' addition of bases to the guide sequence, and the "No Secondary" condition uses an sgRNA with a non-stem forming 5' addition to the guide sequence. The "3 bp Stem" and the "6 bp Stem" conditions use sgRNAs with regions designed to form stems of 3 and 6 bp length at the 5' end of the sgRNA, respectively.

Example 3: Generation and Characterization of Deactivatable sgRNA

Six sgRNAs were synthesized. The sequences representing a part of the sgRNAs are provided below. Modification on sgRNAs includes 2'-O-methyl analogs and 3' phosphorothioate internucleotide linkages at the first three 5' and 3' terminal RNA nucleotides.

```
Control:
                                        (SEQ ID NO: 1)
NNNNNNNNNNNNNNNNNNNNNGUUUUAGAGCUAGAAAUAGCAAGUUAAAAU

AAGGCUAGUCCGUUAUCAACUUGAAAAAGUGGCACCGAGUCGGUGCUUUU 21
                                        (SEQ ID NO: 5)
NNNNNNNNNNNNNNNNNNNNN*UUUUAGAGCUAGAAAUAGCAAGUUAAAAU

AAGGCUAGUCCGUUAUCAACUUGAAAAAGUGGCACCGAGUCGGUGCUUUU 24
                                        (SEQ ID NO: 6)
NNNNNNNNNNNNNNNNNNNNNGUU*UAGAGCUAGAAAUAGCAAGUUAAAAU

AAGGCUAGUCCGUUAUCAACUUGAAAAAGUGGCACCGAGUCGGUGCUUUU 50
                                        (SEQ ID NO: 7)
NNNNNNNNNNNNNNNNNNNNNGUUUUAGAGCUAGAAAUAGCAAGUUAAAA
```

```
                                        (SEQ ID NO: 8)
*AAGGCUAGUCCGUUAUCAACUUGAAAAAGUGGCACCGAGUCGGUGCUUUU

U 57
                                        (SEQ ID NO: 9)
NNNNNNNNNNNNNNNNNNNNNGUUUUAGAGCUAGAAAUAGCAAGUUAAAAU

AAGGCU*

(SEQ ID NO: 10)
GUCCGUUAUCAACUUGAAAAAGUGGCACCGAGUCGGUGCUUUU 74
                                        (SEQ ID NO: 11)
NNNNNNNNNNNNNNNNNNNNNGUUUUAGAGCUAGAAAUAGCAAGUUAAAA

UAAGGCUAGUCCGUUAUCAACUUG (SEQ ID NO: 12)
*AAAAGUGGCACCGAGUCGGUGCUUUU
```

Figure 4:
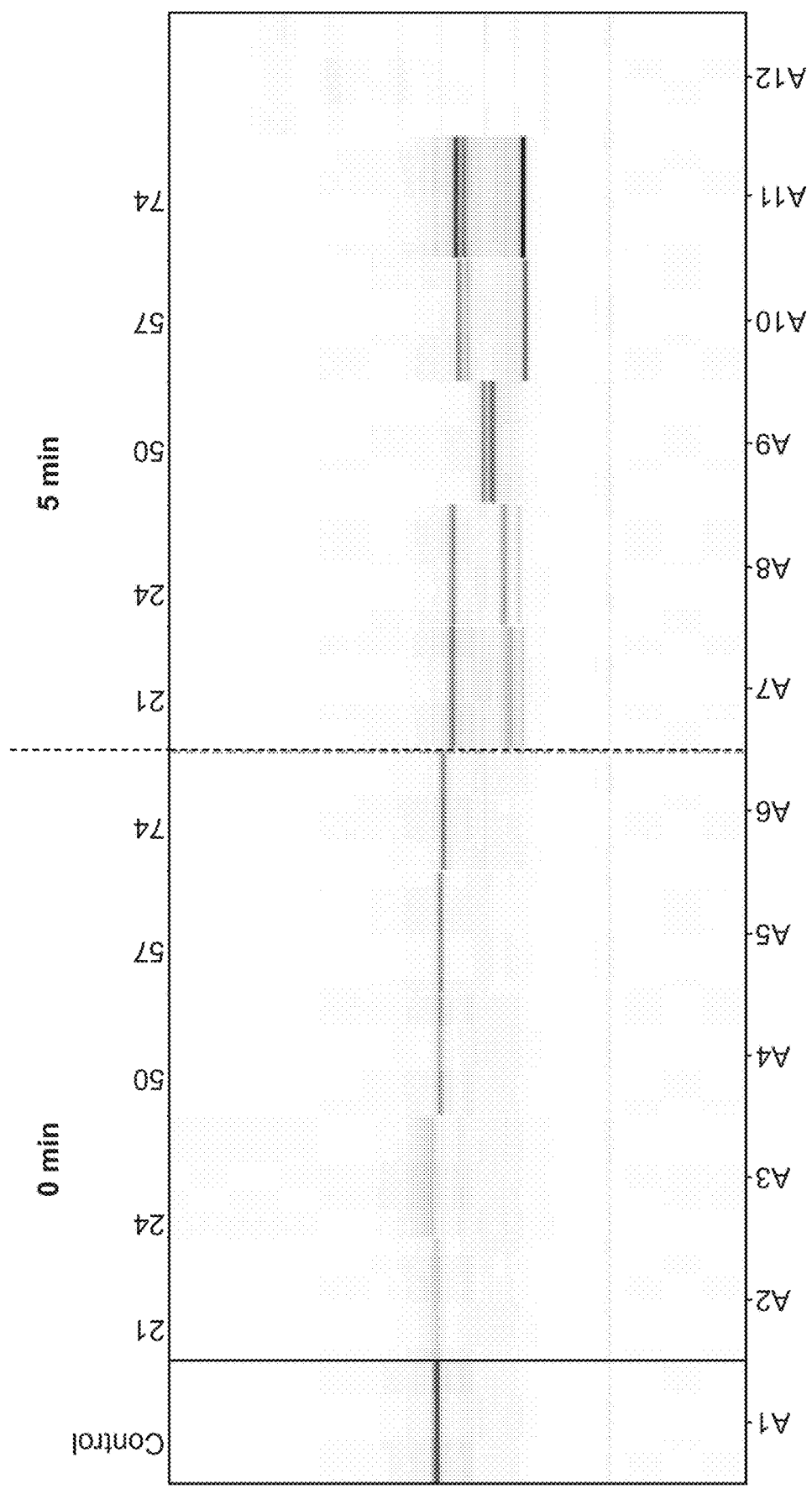
FIG. 4 shows the efficacy of cleavage of deactivatable CRISPR-OFF sgRNA variants. sgRNAs with five different cleavage points were subjected to cleavage agent (UV light) for 0 (left) or 5 (right) minutes.

The first sgRNA ("Control") did not comprise a photocleavable element. The second, third, fourth and fifth sgRNAs had photocleavable bonds at positions 21, 24, 50, 57 and 74 from the 5' end of the sgRNA Five of the sgRNAs were then exposed to UV light for 5 minutes. FIG. 4 is an image of a gel depicting the five sgRNAs after exposure to UV light, run using fragment analyzer from Advanced Analytical. All samples were run with small RNA kit according to manufacturer protocol. After 5 minutes of exposure to UV light, all five sgRNAs showed a banding pattern consistent with cleavage at the respective positions of the photocleavable bond.

Example 4: Rapid Generation of Genome Edited Cell Lines

Figure 5:
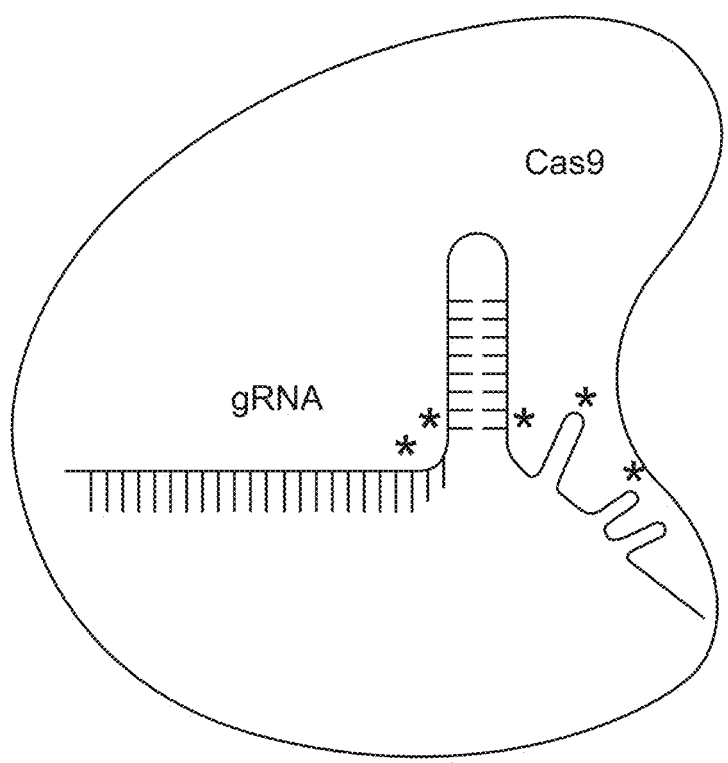
FIG. 5 is a schematic illustrating positions of cleavable linkers in sgRNA.
Figure 6:
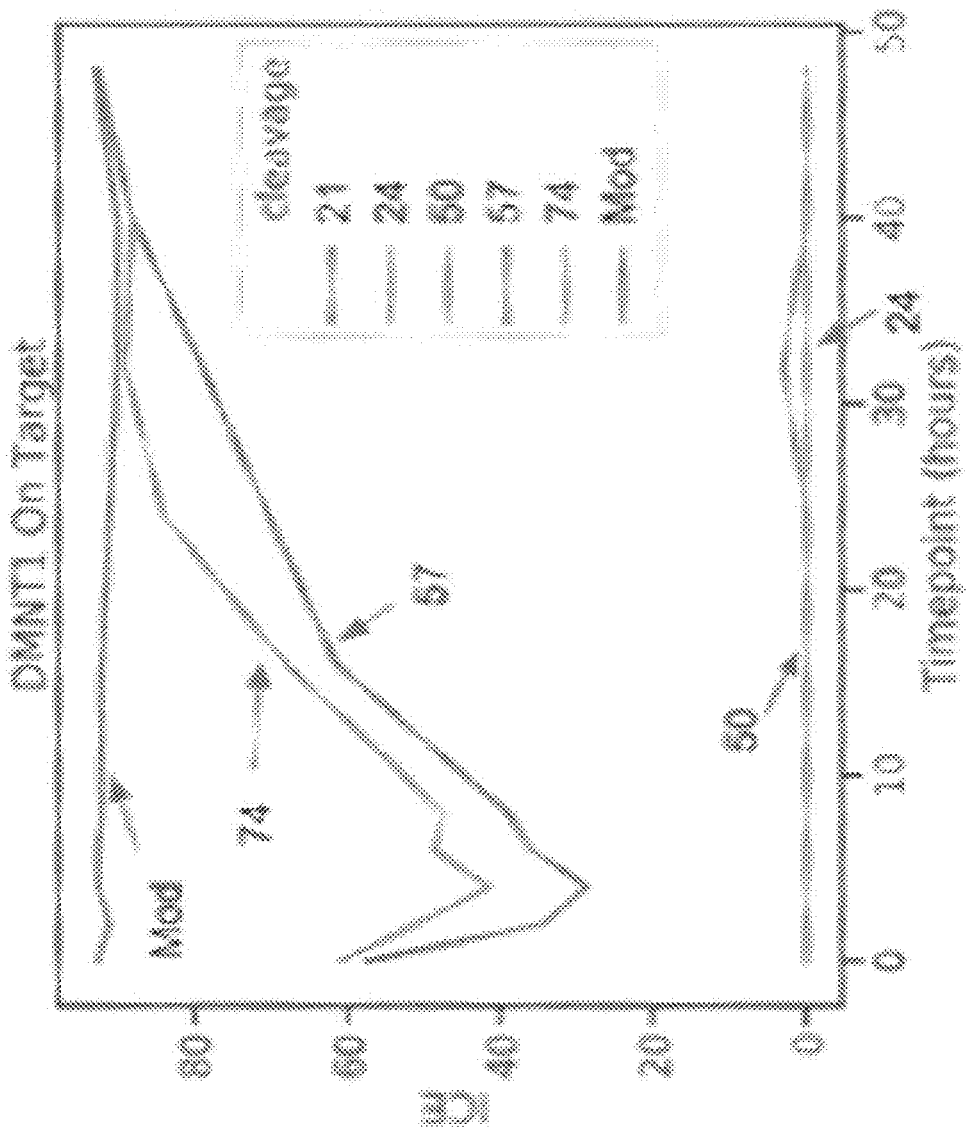
FIG. 6 shows a schematic of time-dependent CRISPR-OFF deactivation of genome editing efficiency in cells. Cells transfected with deactivatable sgRNA variants were treated with UV light at time points after RNP delivery and were allowed 48 total hours post RNP delivery to edit, repair, and recover. After 48 hours genomic DNA was harvested from all samples and analyzed for the presence of indels. Two CRISPR-OFF sgRNAs (57 and 74) displayed time dependent deactivation of genome editing efficiency.

HEK 293T cells expressing Cas9 were transfected with sgRNAs comprising photocleavable linkers and subjected to cleavage agent. FIG. 5 shows a schematic of programmable genome editing efficiency with six different sgRNAs targeting DNMT1. The first sgRNA ("Mod") lacked a photocleavable site. The second, third, fourth and fifth sgRNAs had photocleavable bond at positions 21, 24, 50, 57 and 74 from 5' end of the sgRNA (b21, b24, b50, b57, and b74, respectively). sgRNA:Cas9 mixture [9:1 ratio] was introduced into the cells. The cells were exposed to the cleavage agent every two hours for 48 hours. Each sample was kept in the dark until the designated time point, then exposed once to UV light to induce cleavage. Cells were then left in dark until 48 hours post transfection. All samples were harvested 48 hours post transfection. After 48 hours post-transfection, genomic DNA was harvested from all samples and analyzed for presence of insertions and deletions using standard procedures known in the art. ICE (Inference of CRISPR Editing) measured the amount of gene editing by analyzing Sanger sequencing traces and mapping level of sequence breakdown to determine indel formation frequencies, similar to as described in Brinkmann et al. 2014 Nucleic Acids Research and Hsiau et al. "Inference of CRISPR Edits from Sanger Trace Data", Jan. 14, 2019 bioRxiv. The graph in FIG. 6 represents editing efficiency. Samples were amplified using PCR and submitted for sequencing. After sequencing the number of sequences which are wild-type or edited following amplification were analyzed by ICE. Editing is expressed by percentage of sequences that are not wildtype.

sgRNAs with photocleavable bonds at positions 57 and 74 display time dependent deactivation of genome editing efficiency.

Example 5: Generation of Edited HEK 293 Cell Lines

HEK 293 cells were transfected with Cas9 and sgRNAs comprising photocleavable (PC) linkers and were subjected to UV light to cleave the linker. Cas9 was complexed with 12 different sgRNAs comprising PC linker phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 (CRISPR OFF) with target binding regions targeting BUB1B (AGTGAAGC-CATGTCCCTGGA) (SEQ ID NO: 13), CAMK1 (sg1: TGCCAGGATCACCTCCGAGA) (SEQ ID NO: 14), PRKAG3 (sg1—AGCAAGAAAACAGCAGCTCA (SEQ ID NO: 15); sg2—AGCAAGAAAACAGCAGCUCA) (SEQ ID NO: 16), STK3 (sg1—TCCTGAAGATCTGATT-CAAC (SEQ ID NO: 17); sg2—AAAGCAATA-CACAAGGAATC (SEQ ID NO: 18); sg3—CCAT-AATGCAGCAATGTGAC (SEQ ID NO: 19); 4—UUUAAUUGCGACAACUUGAC (SEQ ID NO: 20)), IRAK4 (GTCCTGTCTTTGTCACAGAA (SEQ ID NO: 21)), and Chr8q23(sg1—AGTCTACTATGAGTTTTCTG (SEQ ID NO: 22); sg2—TTATAGTTACGATGTTTGAT (SEQ ID NO: 23); sg3—AAGCCTCAAATTAGGAGAAA (SEQ ID NO: 24)) to produce 12 experimental populations. Cas9 was also complexed with 12 different sgRNAs without photocleavable linkers (standard) with the target binding regions described above. To form each of the 24 complex solutions, 10 μmol of Cas9 protein was mixed with 30 pmol of sgRNA. Each solution was diluted to 20 μL using transfection buffer and allowed to mix for 15 minutes at room temperature. HEK293 cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 μL. The cell suspension was then added to the precomplexed Cas9 sgRNA solution and transfected. Each experimental population was split into two wells to form paired replicates of control and treatment cells. Four hours after transfection, treatment cells were exposed to UV light for one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by percentage of sequences that are not wildtype.

Figure 7:
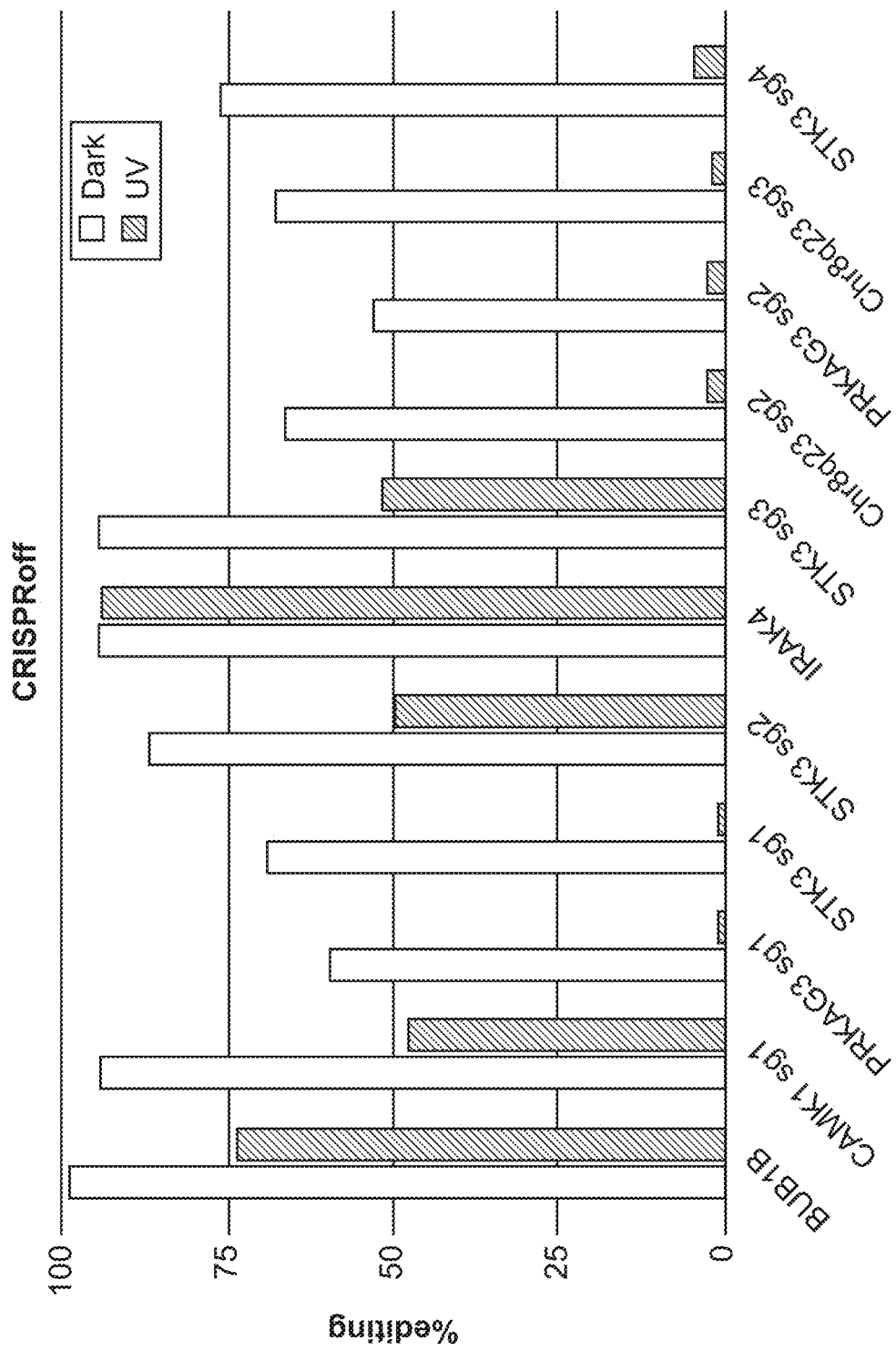
FIG. 7 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 7 shows a graph of the editing efficiency of Cas9 with the 12 different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 8:
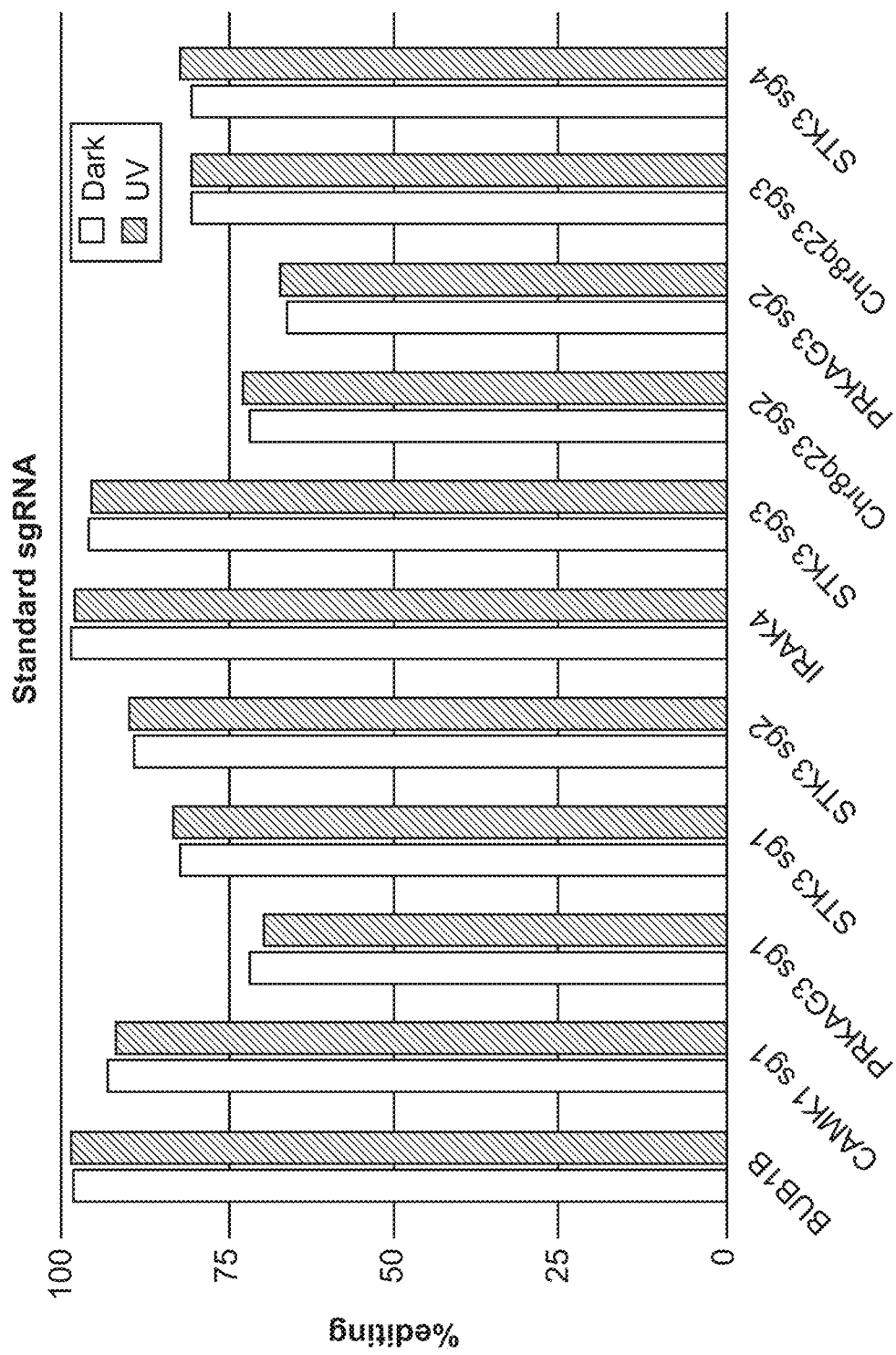
FIG. 8 shows results of an experiment ran as a control for the experiment corresponding to FIG. 7, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 8 shows the editing efficiency of Cas9 with 12 different standard sgRNAs without a photocleavable linker, with the same target binding region as the sgRNAs in FIG. 7. The grey bars indicate the editing efficiency of the Cas9 in complex with the standard sgRNA without UV light exposure. The black bars indicate the editing efficiency of the Cas9 in complex with standard sgRNA after UV light exposure.

Example 6: Generation of Edited U2OS Cell Lines

U2OS cells were transfected with Cas 9 and sgRNAs comprising photocleavable linkers and were subjected to UV light to cleave the linker. Cas9 was complexed with six different sgRNAs comprising phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 (CRISPR OFF) with target binding regions targeting DNMT1(GGAGTGAGG-GAAACGGCCCC (SEQ ID NO: 25)), EMX1 (GAGTCCGAGCAGAAGAAGAA) (SEQ ID NO: 26), FANCF(GCTGCAGAAGGGATTCCATG) (SEQ ID NO: 27), GRK1(GCCGTCAAAGCTGCCTCGGG) (SEQ ID NO: 28), PRGN(CAGATGCCTGCTCAGTGTTG) (SEQ ID NO: 29), and VEGFA(GGTGAGT-GAGTGTGTGCGTG) (SEQ ID NO: 30) to produce six experimental populations. Cas9 was also complexed with six different sgRNAs without photocleavable linkers (standard) with the target binding regions described above. To form each of the 12 complex solutions, 10 pmol of Cas9 protein was mixed with 30 pmol of sgRNA. Each solution was diluted to 20 μL using transfection buffer and allowed to mix for 15 minutes at room temperature. U2OS cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 μL. The cell suspension was then added to the precomplexed Cas9 sgRNA solution and transfected. Each experimental population was split into two wells to form paired replicates of control and treatment cells. Four hours after transfection, treatment cells were exposed to UV light for one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by percentage of sequences that are not wildtype.

Figure 9:
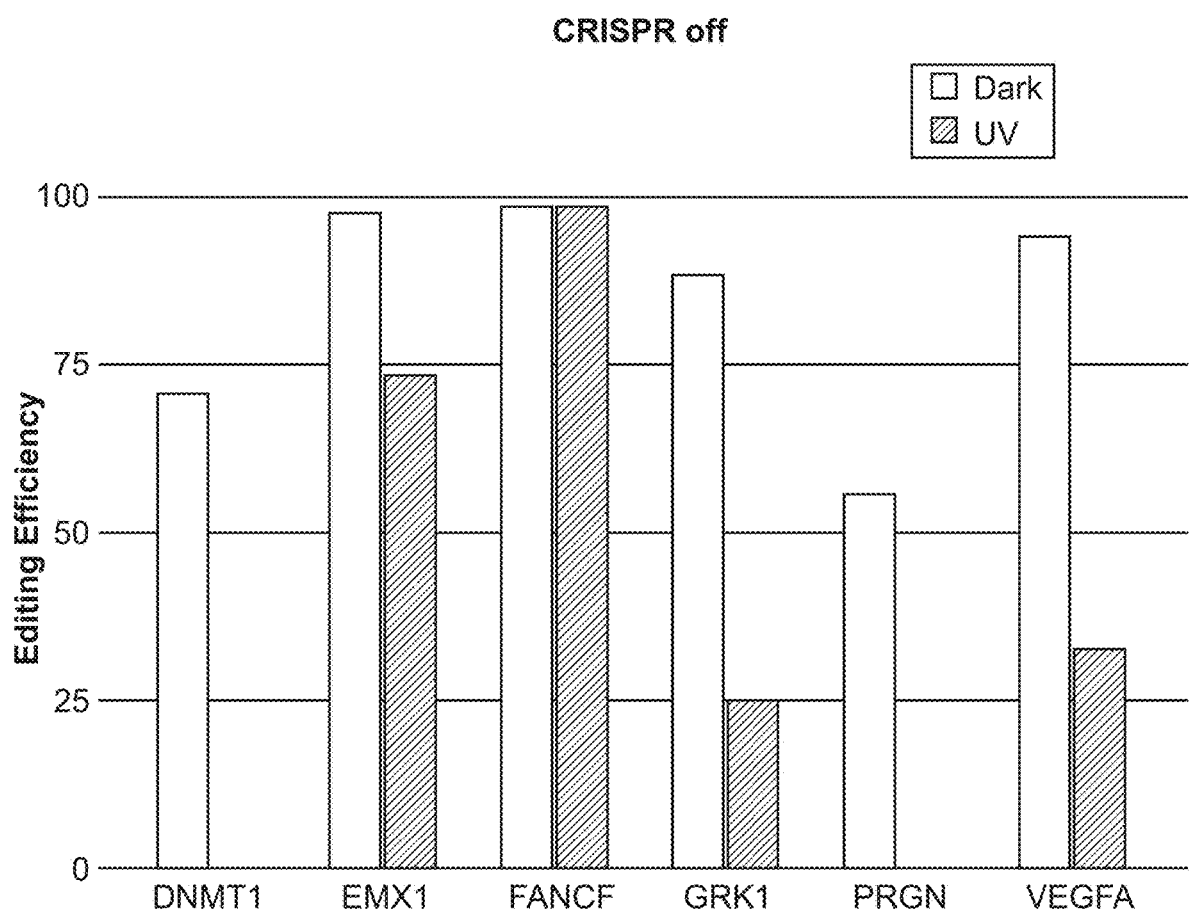
FIG. 9 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 9 shows a graph of the editing efficiency of Cas9 with the six different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 10:
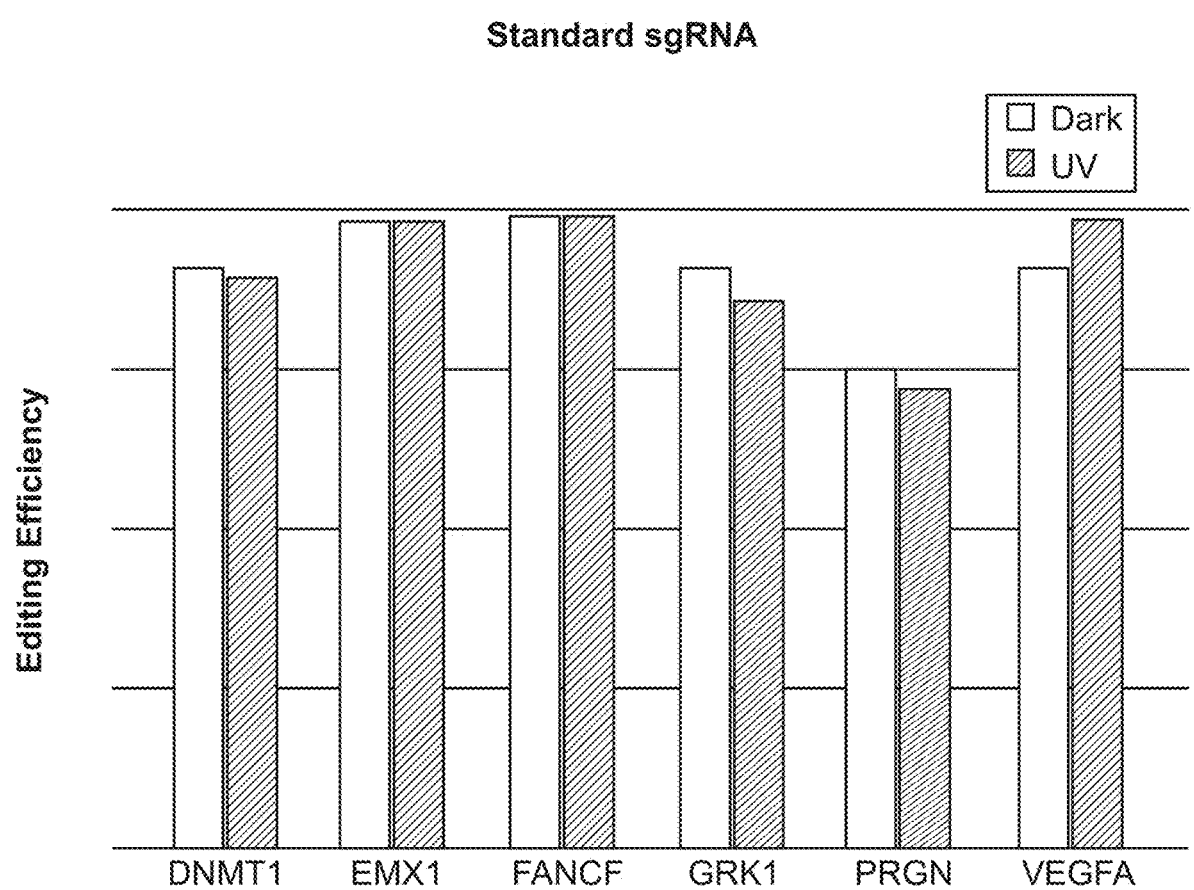
FIG. 10 shows results of an experiment ran as a control for the experiment corresponding to FIG. 9, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 10 shows the editing efficiency of Cas9 with six different standard sgRNAs without a photocleavable linker, with the same target binding region as the sgRNAs in FIG. 9. The grey bars indicate the editing efficiency of the Cas9 in complex with the standard sgRNA without UV light exposure. The black bars indicate the editing efficiency of the Cas9 in complex with standard sgRNA after UV light exposure.

Example 7: Analysis of Off-Target Editing by CRISPR-OFF Cas9 Complexes in HEK293T Cells without Exposure to UV Light FIG. 13 includes graphs depicting the percentage of editing at the off-target sites known to have a high degree of off-target editing for the sgRNAs targeting DNMT1, FANCF, and VEGFA described above.

The sequences used are as follows, where * indicates the location of a linker (3-(4,4'-Dimethoxytrityl)-1-(2-nitrophenyl)-propan-1-yl-[(2-cyanoethyl)-(N,N-diisopropyl)]-phosphoramidite):

```
DNMT1
On-target sgRNA:
                                        (SEQ ID NO: 31)
GGAGTGAGGGAAACGGCCCCGTTTTAGAGCTAGAAATAGCAAGTTAAAAT

AAGGCTAGTCCGTTATCAACTTGAAAAAGTGGCACCGAGTCGGTGCTTTT

On-target CRISPR OFF:
                                        (SEQ ID NO: 32)
GGAGTGAGGGAAACGGCCCCGTTTTAGAGCTAGAAATAGCAAGTTAAAAT

AAGGCT (SEQ ID NO: 33)
*GTCCGTTATCAACTTG (SEQ ID NO: 34)
*AAAAGTGGCACCGAGTCGGTGCTTTT

Off-Target 1:
                                        (SEQ ID NO: 35)
GGAGGGAGGGAAACAGCCCC FANCF
On-target sgRNA:
                                        (SEQ ID NO: 36)
GCTGCAGAAGGGATTCCATGGTTTTAGAGCTAGAAATAGCAAGTTAAAAT

AAGGCTAGTCCGTTATCAACTTGAAAAAGTGGCACCGAGTCGGTGCTTTT

On-target CRISPR OFF:
                                        (SEQ ID NO: 37)
GCTGCAGAAGGGATTCCATGGTTTTAGAGCTAGAAATAGCAAGTTAAAAT

AAGGCT (SEQ ID NO: 33)
*GTCCGTTATCAACTTG (SEQ ID NO: 34)
*AAAAGTGGCACCGAGTCGGTGCTTTT

Off-Target 2:
                                        (SEQ ID NO: 38)
GCTGCAGAAGGGATTCCAAG VEGFA
On-target sgRNA:
                                        (SEQ ID NO: 39)
GGTGAGTGAGTGTGTGCGTGGTTTTAGAGCTAGAAATAGCAAGTTAAAAT

AAGGCTAGTCCGTTATCAACTTGAAAAAGTGGCACCGAGTCGGTGCTTTT

On-target CRISPR OFF:
                                        (SEQ ID NO: 40)
GGTGAGTGAGTGTGTGCGTGGTTTTAGAGCTAGAAATAGCAAGTTAAAAT

AAGGCT (SEQ ID NO: 33)
*GTCCGTTATCAACTTG (SEQ ID NO: 34)
*AAAAGTGGCACCGAGTCGGTGCTTTT
```

Off-Target 3: GCTGAGTGAGTGTATGCGTG (SEQ ID NO: 41)

Figure 13:
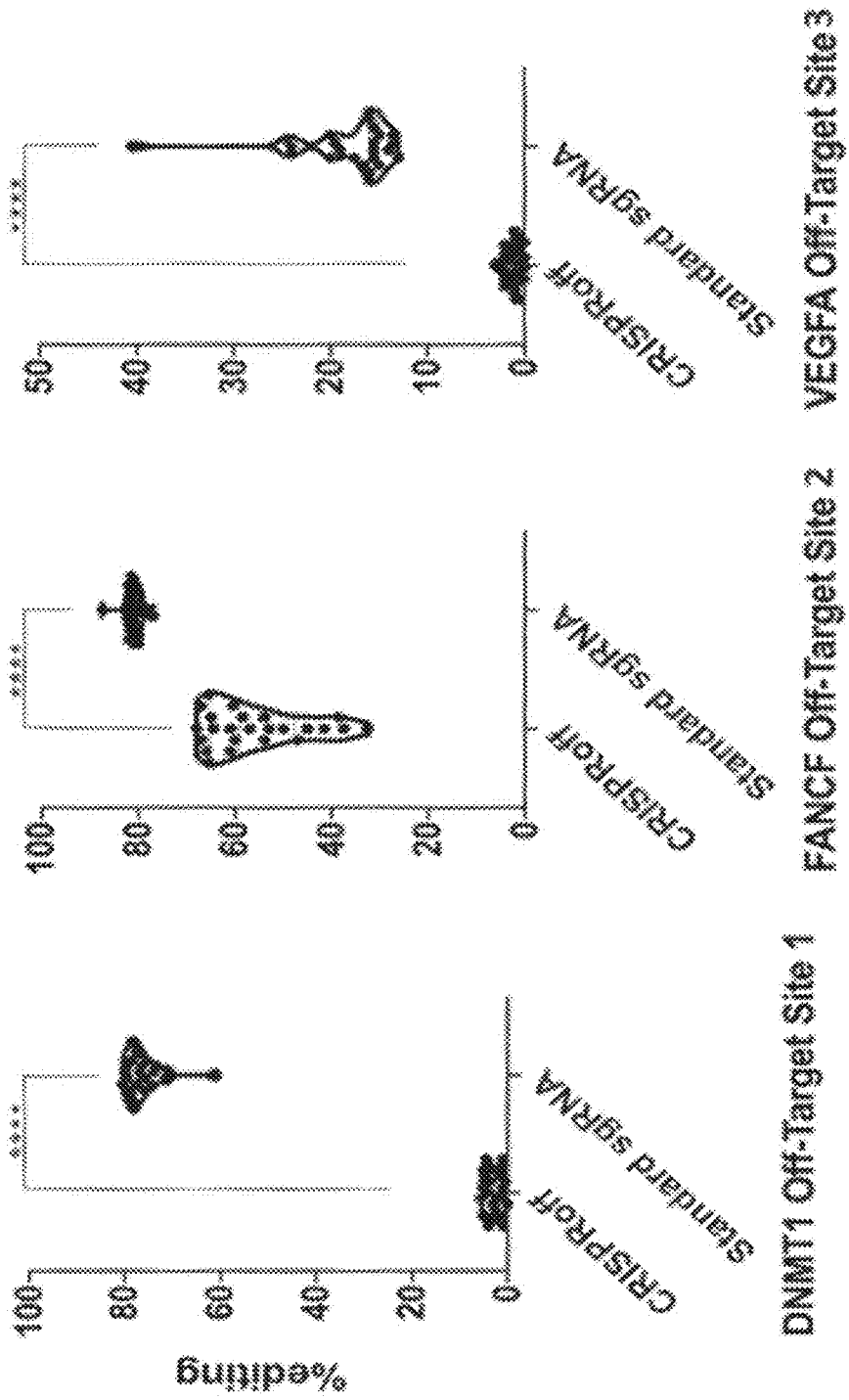
FIG. 13 shows a series of scatterplots comparing off-target editing activity using either CRISPR OFF sgRNAs or modified sgRNAs at top predicted off-target sites across three gene targets. CRISPR OFF sgRNAs caused significantly fewer off-target indels than sgRNAs modified only to include 2'-O-methyl analogs and 3' phosphorothioate internucleotide linkages at the first three 5' and 3' terminal RNA nucleotides. (****$p<0.0001$, Student's unpaired t-test, n=24 technical replicates)

ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. CRISPR ribonucleoproteins (RNPs) were formed using a 30pmol:10pmol ratio between sgRNA:Cas9. RNPs were then transfected into HEK293T cells. 48 hours post-transfection, cells were harvested and genomic DNA was harvested from the cells in n=24 biological replicates. The cells were not exposed to UV light. Editing is expressed by percentage of sequences that are not wildtype. The X axis indicates whether the off-target editing was produced by a Cas9 in complex with an sgRNA comprising 3-(4,4'-Dimethoxytrityl)-1-(2-nitrophenyl)-propan-1-yl-[(2-cyanoethyl)-(N,N-diisopropyl)]-phosphoramidite ("CRISPRoff"), or by a Cas9 in complex with a sgRNA without a 3-(4,4'-Dimethoxytrityl)-1-(2-nitrophenyl)-propan-1-yl-[(2-cyanoethyl)-(N,N-diisopropyl)]-phosphoramidite ("standard sgRNA"). The Y axis indicates the percentage of the off-target site that was edited. As can be seen in FIG. 13, the off-target editing observed for a CRISPR enzyme complexed with a sgRNA targeting DNMT1 without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001; the off-target editing observed for a CRISPR enzyme complexed with a sgRNA targeting FANCF without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001; the off-target editing observed for a CRISPR enzyme complexed with a sgRNA targeting VEGFA without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001. The editing efficiency at the target site of each of the aforementioned CRISPR-OFF sgRNAs was the same or 1-3% lower than of the editing efficiency at the target site of each of the aforementioned standard sgRNAs as measured by ICE as described above. The results illustrate that use of the sgRNAs with the 3-(4,4'-Dimethoxytrityl)-1-(2-nitrophenyl)-propan-1-yl-[(2-cyanoethyl)-(N,N-diisopropyl)]-phosphoramidite in the nexus and stem loop 1 in editing assays results in lower off-target editing activity relative to use of the sgRNAs lacking the 3-(4,4'-Dimethoxytrityl)-1-(2-nitrophenyl)-propan-1-yl-[(2-cyanoethyl)-(N,N-diisopropyl)]-phosphoramidite in the nexus and stem loop 1.

Example 8: Analysis of Time-Dependent Activity of Cas9 in Complex with CRISPR OFF in U2OS Cells FIGS. 14-16 are graphs depicting a time-dependent activity of Cas 9 in complex with "CRISPRoff" targeting DNMT1, GRK1, and VEGFA contrasted against the activity of Cas9 in complex with "standard sgRNA." Cells were exposed to UV light every two hours for 48 hours. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv.

Example 9: Generation of Edited K562 Cell Lines

K562 cells were transfected with Cas9 and sgRNAs comprising photocleavable linkers and were subjected to UV light to cleave the linker. Cas9 was complexed with two different sgRNAs comprising phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 (CRISPR OFF) with target binding regions targeting EMX1 (GAGTCCGAGCAGAAGAAGAA) and GRK1(GCCGTCAAAGCTGCCTCGGG) to produce two experimental populations. Cas9 was also complexed with 2 different sgRNAs without photocleavable linkers (standard) with the target binding regions described above. To form each of the 4 complex solutions, 10 pmol of Cas9 protein was mixed with 30 pmol of sgRNA. Each solution was diluted to 20 µL using transfection buffer and allowed to mix for 15 minutes at room temperature. K562 cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 µL. The cell suspension as then added to the precomplexed Cas9 sgRNA solution and transfected. Each experimental population was split into two wells to form paired replicates of control and treatment cells. Four hours after transfection, treatment cells were exposed to UV light for one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by the percentage of sequences that are not wildtype.

Figure 11:
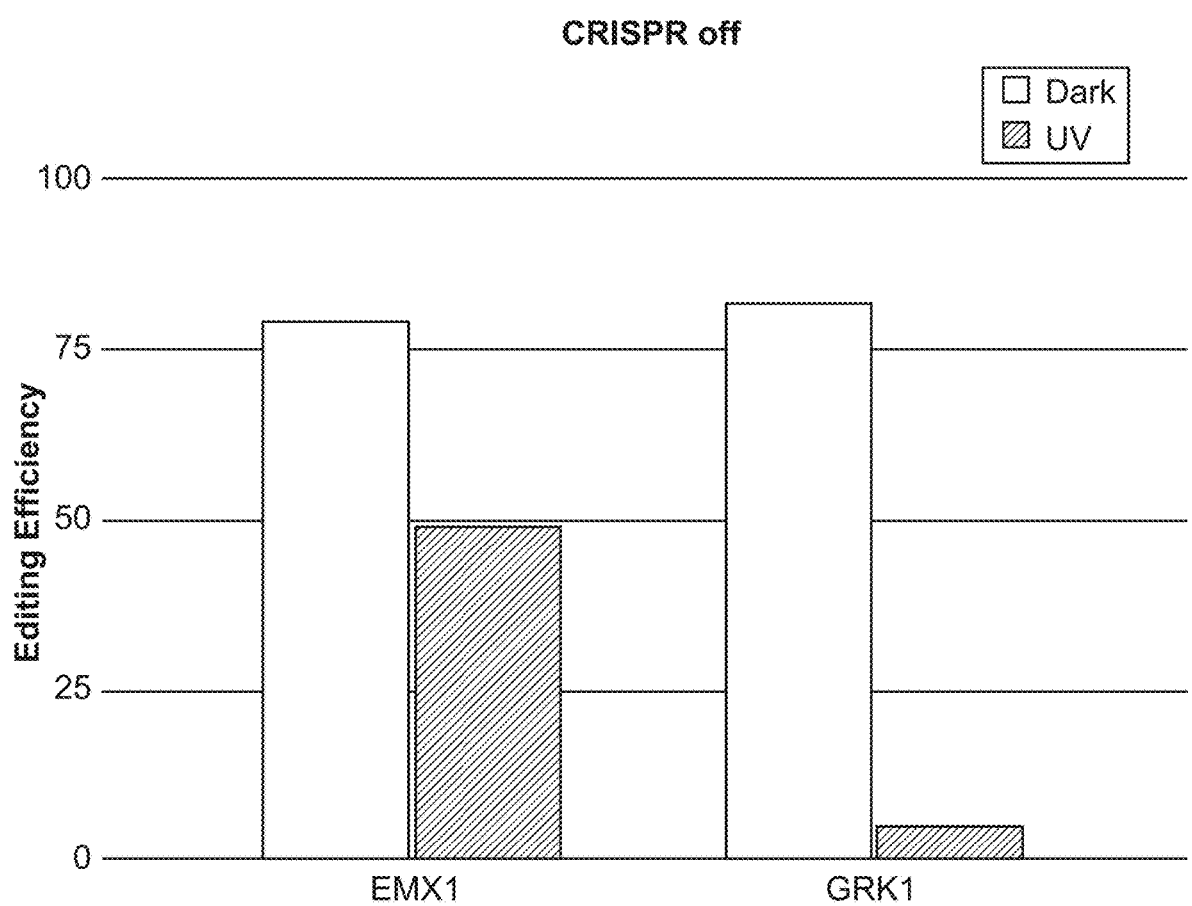
FIG. 11 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 11 shows a graph of the editing efficiency of Cas9 with two different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 12:
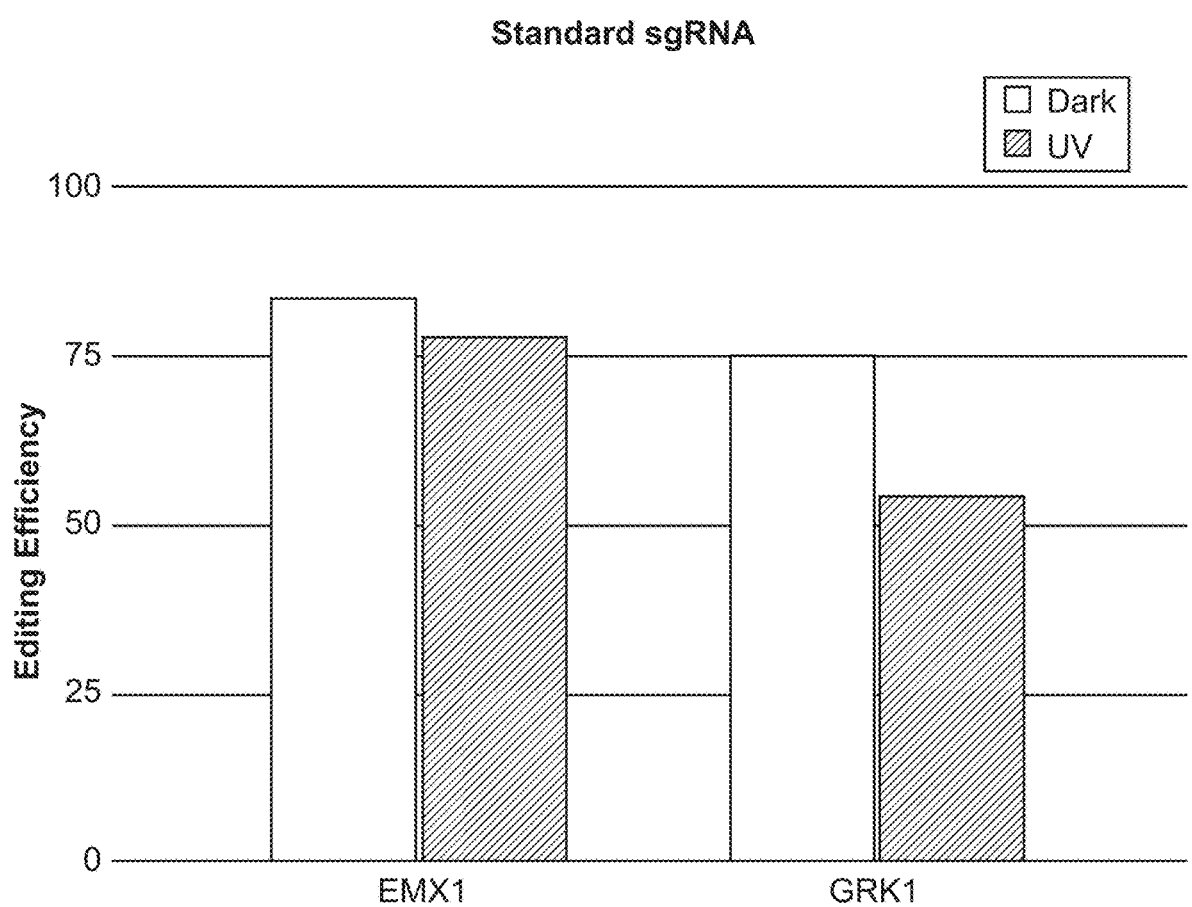
FIG. 12 shows results of an experiment ran as a control for the experiment corresponding to FIG. 11, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 12 shows the editing efficiency of Cas9 with 2 different standard sgRNAs without a photocleavable linker, with the same target binding region as the sgRNAs in FIG. 11. The grey bars indicate the editing efficiency of the Cas9 in complex with the standard sgRNA without UV light exposure. The black bars indicate the editing efficiency of the Cas9 in complex with standard sgRNA after UV light exposure.

Example 10: Transcriptional Regulation

A modified activatable (CRISPR ON) sgRNA polynucleotide comprising a 5' polynucleotide leader sequence that forms a 10 bp stem loop is complexed to an inactive Cas9 nuclease (dCas9) fused with a transcription activator domain of VP64. A photocleavable element is inserted 3' of the polynucleotide leader sequence and immediately 5' of the guide sequence. The CRISPR complex comprising the sgRNA complexed with dCas9 fusion enzyme is transfected into HEK 293T cells. The 5' polynucleotide leader sequence renders the CRISPR complex unable to efficiently anneal to the promoter of the target sequence complementary to the guide sequence. The target gene has relatively low transcriptional activity. At a desired time, the transfected cell is exposed to UV light, resulting in cleavage of the photocleavable bond and release of the polynucleotide leader sequence. The CRISPR complex now more efficiently binds to the promoter of the target sequence, and more efficient transcription of the target sequence results.

Example 11: Analysis of On-Target Editing by CRISPR-OFF Cas9 Complexes in HEK293 Cells with and without Exposure to UV Light Human embryonic kidney cells (HEK293) were maintained between passage 5-20 in Advanced Modified Eagles Medium (Life Technologies) and 10% v/v FBS. Cells were passaged biweekly at a 1:8 ratio with TrypLE (Life Technologies).

HEK 293 cells were transfected with Cas9 and sgRNAs comprising photocleavable (PC) linkers and were subjected to light filtered with a 345 nm bandpass filter to cleave the linker. Cas9 was complexed with 23 different sgRNAs comprising a photocleavable linker (1-(7-(diethylamino)-2-oxo-2H-chromen-4-yl)propyl), incorporated at positions 57 and 74 (CRISPR OFF) with target binding regions targeting AAVS1 (GGGGCCACUAGGGACAGGAU (SEQ ID NO: 42)), BUB1B(AGUGAAGCCAUGUCCCUGGA (SEQ ID NO: 43)), CAMK1_sg1(UGCCAGGAUCACCUCCGAGA (SEQ ID NO: 44), CAMK1_sg2 (GCGUCCUCUUAUCUUCUGCC (SEQ ID NO: 45)), CEL (AACCAGUUGCAGGCGCCCCA (SEQ ID NO: 46)), Chr8q23_sg1(UUAUAGUUACGAUGUUUGAU (SEQ ID NO: 47)), CXCR4(GAUAACUACACCGAGGAAAU (SEQ ID NO: 48)), DNMT1(GGAGUGAGGGAAACGGCCCC (SEQ ID NO: 49)), EMX1(GAGUCCGAGCAGAAGAAGAA (SEQ ID NO: 50)), FAM163A (CUGCAGGGCUCGCUGGUGAG (SEQ ID NO: 51)), FANCF(GCUGCAGAAGGGAUUCCAUG (SEQ ID NO: 52)), GAA(AGGAGCCGGUGGGAGCAGGG (SEQ ID NO: 53)), GRK1(GCCGUCAAAGCUGCCUCGGG (SEQ ID NO: 54)), ITGA7 (GGUGCUGGAGGGCGAGGCUG (SEQ ID NO: 55)), IRAK4(GUCCUGUCUUUGUCACAGAA (SEQ ID NO: 56)), MAPRE1(UUCUCUGCAGAUAAUUCCUG (SEQ ID NO: 57)), MIP (GCUGGGGUCCUCACUGCGCU (SEQ ID NO: 58)), OMP(GAACUGUAGCCGCUGCUGCU (SEQ ID NO: 59)), OPN1SW(ACAGGGGCAAUGUGGUACUG (SEQ ID NO: 60)), PRGN(CAGAUGCCUGCUCAGUGUUG (SEQ ID NO: 61)), PRKAG3(AGCAAGAAAACAGCAGCUCA (SEQ ID NO: 16)), STK3_sg1(AAAGCAAUACACAAGGAAUC (SEQ ID NO: 62)), STK3_sg2

(CCAUAAUGCAGCAAUGUGAC (SEQ ID NO: 63)), and VEGFA(GGUGAGUGAGUGUGUGCGUG (SEQ ID NO: 64)) to produce 23 experimental populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 345 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 22:
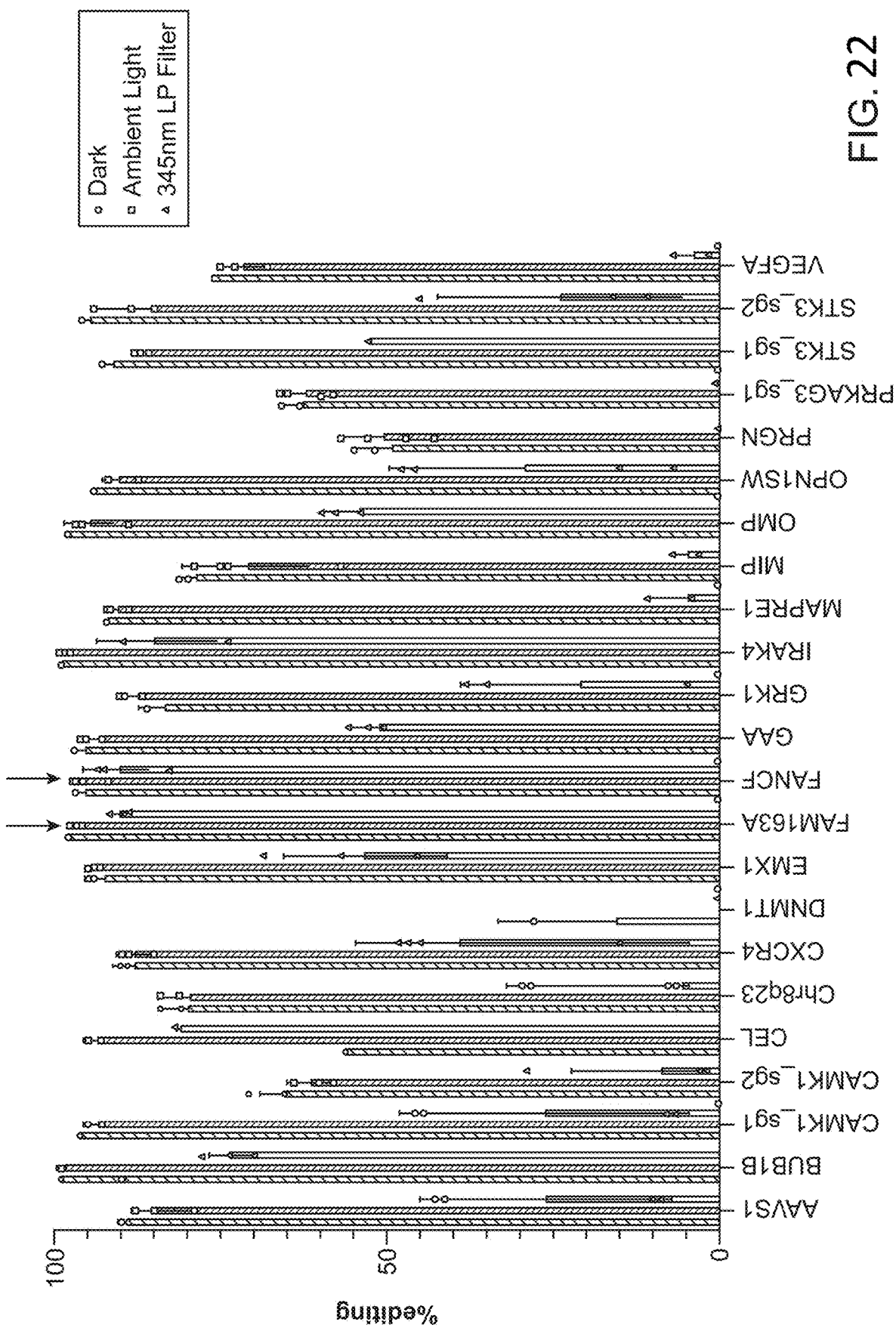
FIG. 22 is a graph comparing the performance, quantified as percent editing, of 23 guide RNAs in HEK293 cells, targeting 23 different target sites, comprising the photocleavable sites of FIG. 18, comparing three conditions: without light, with ambient light, or with light at a wavelength greater than 345 nm.

FIG. 22 shows a graph of the editing efficiency of Cas9 with the 23 different CRISPR OFF sgRNAs. From left to right, for each sgRNA: the black bars (circles), indicate the editing efficiency of the Cas9 in complex with the CRISPR OFF sgRNA without light exposure; the grey bars (squares), indicate the editing efficiency of the Cas9 in complex with CRISPR OFF sgRNA after ambient light exposure; the light grey bars (triangles), indicate the editing efficiency of the Cas9 in complex with CRISPR OFF sgRNA after exposure to light with wavelengths greater than 345 nm. As is pointed out with arrows, FANCF and FAM163 sites show no decrease in editing following exposure. The lamp used was 600W, intensity was 90-120 mW/cm$^2$. Cas9 from Aldevron, with a nuclear localization signal (NLS-Sp.Cas9-NLS), was used in all experiments.

Figure 23:
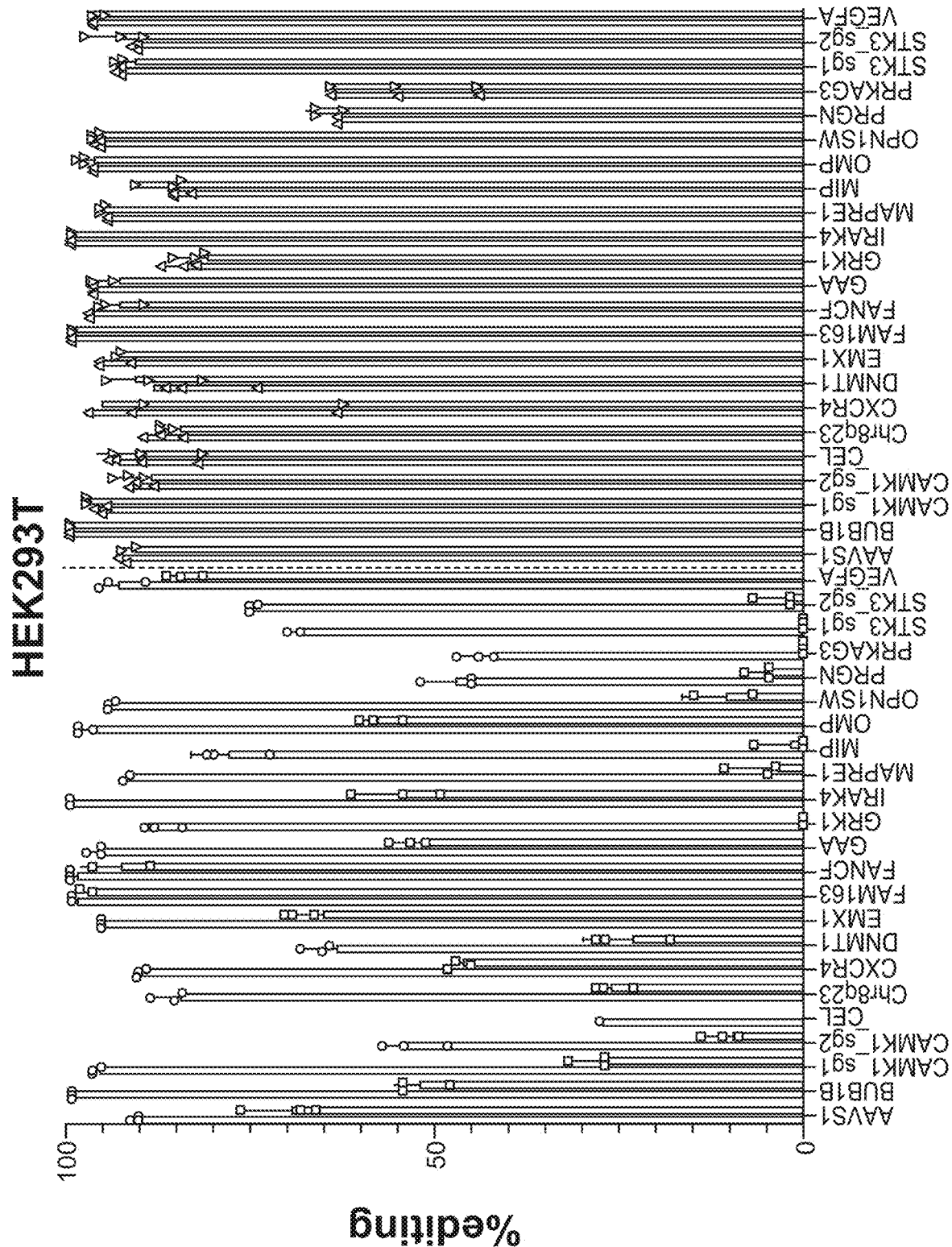
FIG. 23 is a graph comparing the performance, quantified as percent editing, of 23 guide RNAs in HEK293 cells, targeting 23 different target sites, comprising photocleavable linkers at positions 57 and 74, comparing three conditions: without light, with ambient light, or with light at a wavelength greater than 345 nm as compared to sgRNA without photocleavable sites.

FIG. 23 shows a graph of the editing efficiency of Cas9 with the 26 different CRISPR OFF sgRNAs as compared to unmodified sgRNAs with the same target binding sequence.

Figure 30:
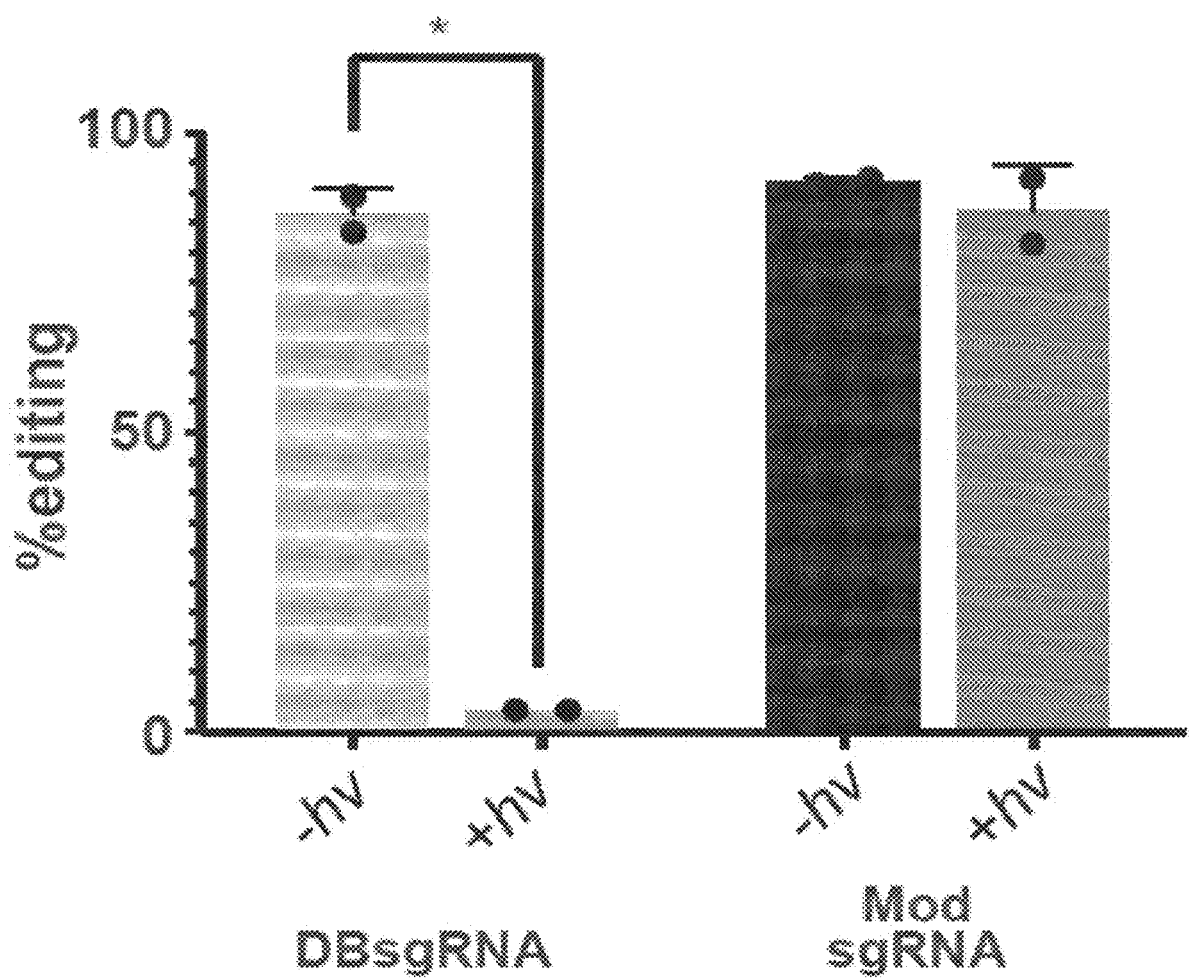
FIG. 30 is a graph showing that the percent editing by the polynucleotide of FIG. 18 significantly decreases upon exposure to light as compared to an sgRNA without photocleavable linkers.

FIG. 30 shows a graph demonstrating the decrease in percent editing observed in cells expressing CRISPR OFF in complex with a Cas9 after exposure to light as compared to cells expressing CRISPR OFF in complex with Cas9 without exposure to light and cells expressing Cas9 in complex with standard sgRNA with and without exposure to light.

Figure 31:
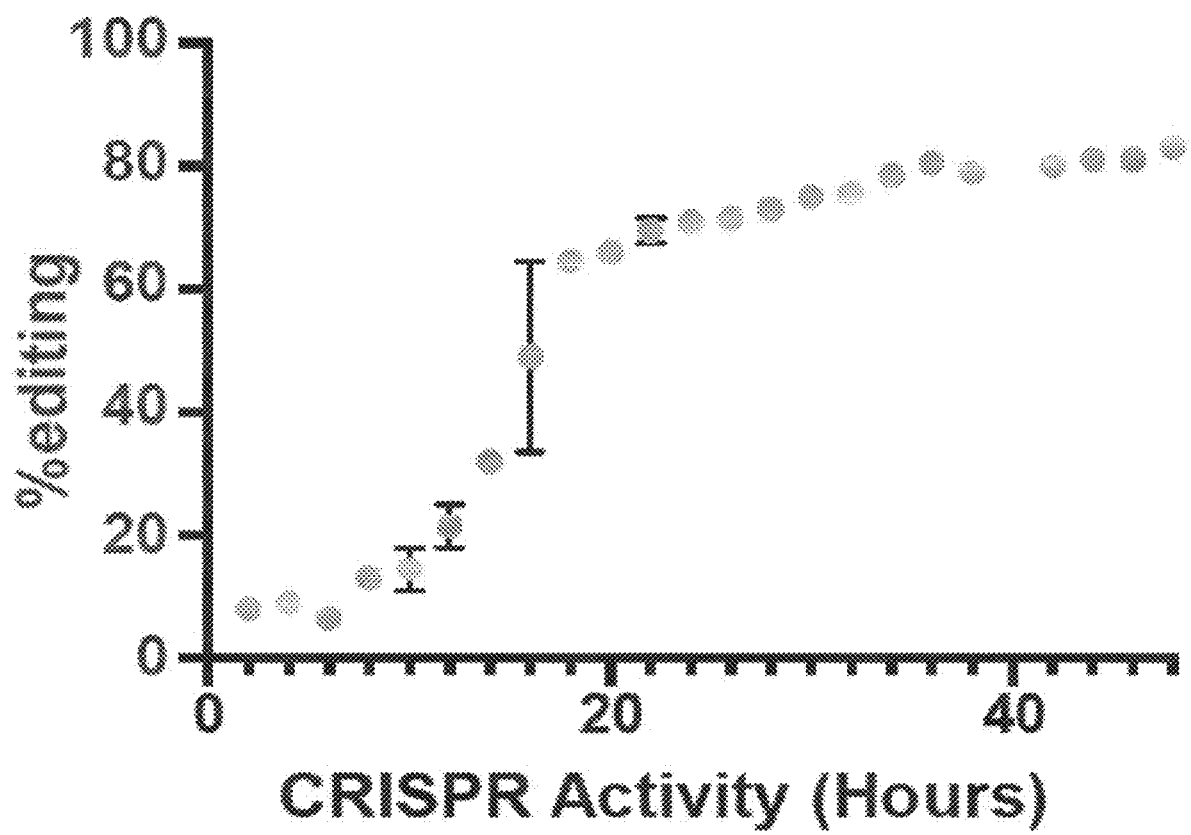
FIG. 31 is a graph showing the change in percent editing activity observed in HEK293 cells by the polynucleotide of FIG. 18 in complex with a Cas9 nuclease over time, with each time point representing the time at which a population of HEK293 cells tested were exposed to light.

FIG. 31 shows a graph demonstrating the increase in percent editing observed over increasing periods of time before the Cas9-CRISPR OFF complex expressed by the cell tested is inactivated with light.

Figure 37:
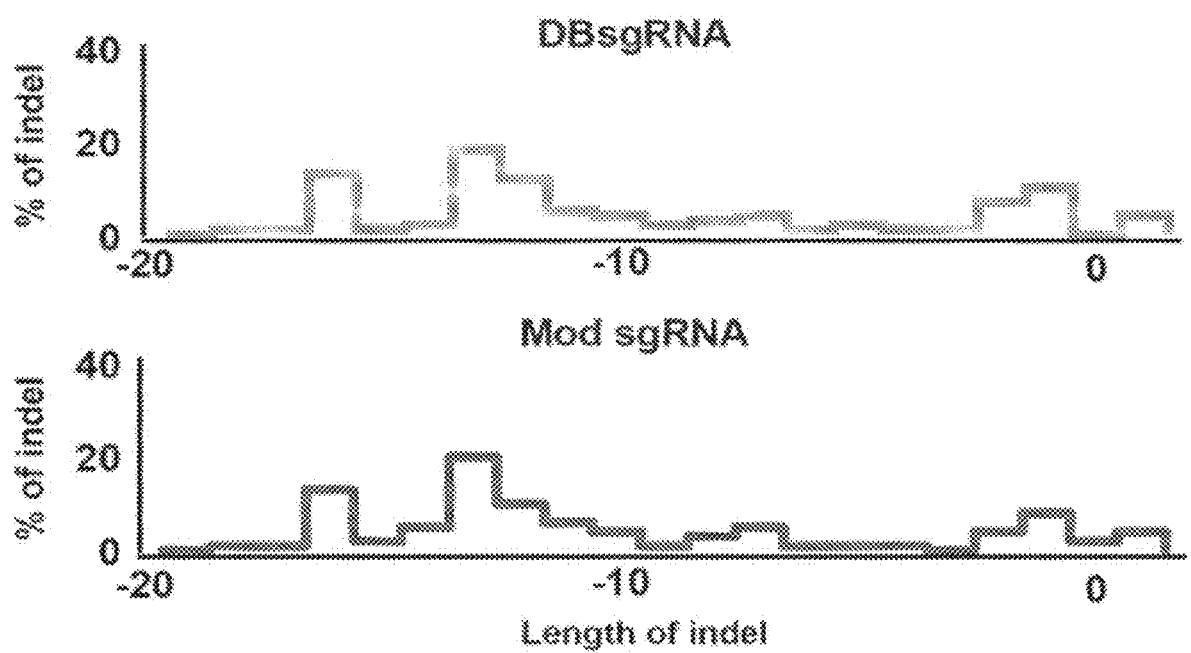
FIG. 37 is an indel profile of the CRISPR OFF polynucleotide in complex with a Cas9 nuclease targeting CAMK1 as compared to a standard sgRNA in complex with a Cas9 nuclease.

FIG. 37 is an indel profile of the aforementioned polynucleotide in complex with a Cas9 nuclease targeting CAMK1 as compared to a standard sgRNA in complex with a Cas9 nuclease.

Figure 35:
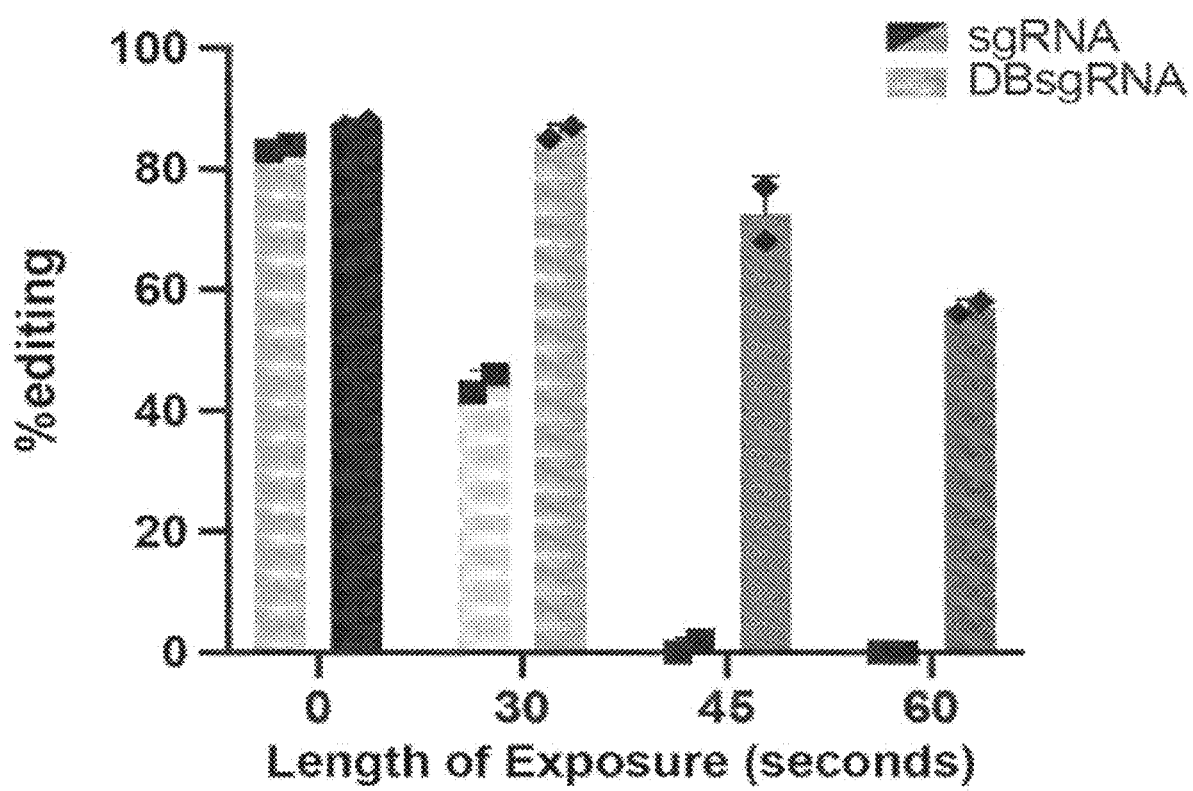
FIG. 35 shows a graph of the effect of light exposure duration on the ablation of editing, wherein complete ablation is achieved between 45-60 seconds.

FIG. 35 shows a graph of the effect of light exposure duration on the ablation of editing, wherein complete ablation is achieved between 45-60 seconds.

Figure 36:
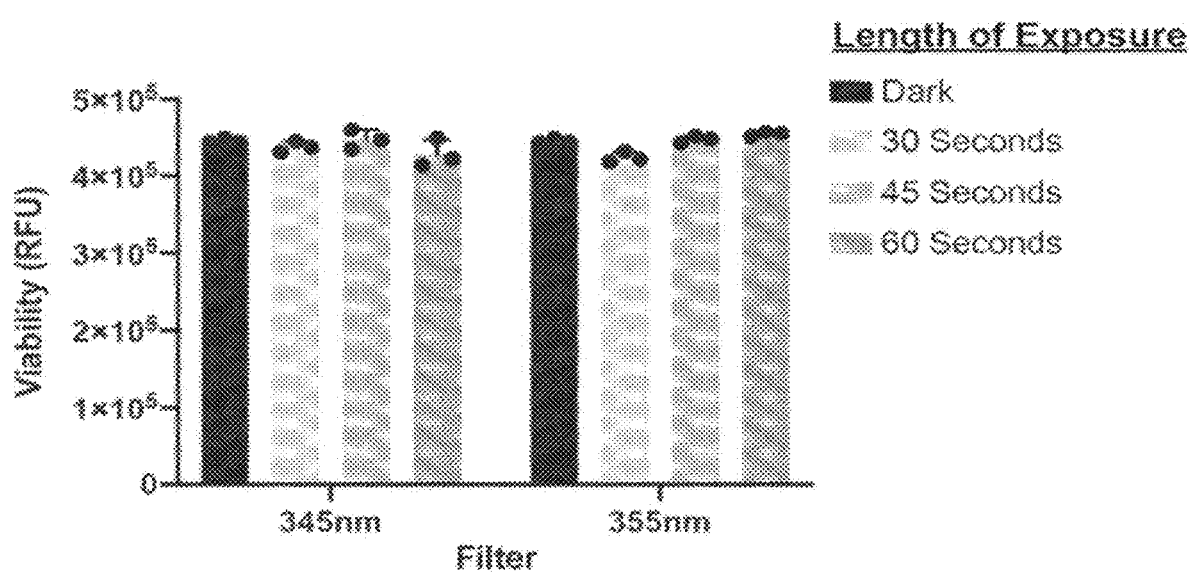
FIG. 36 is a graph showing the effect of increasing exposure time of cells to wide spectrum light on cell viability.

FIG. 36 is a graph showing the effect of increasing exposure time of cells to wide spectrum light on cell viability.

TABLE 1

Target Sequence Primers

| Target | Primer F | Primer R | Primer Seq |
|---|---|---|---|
| AAVS1 | GCCCCTATGTCCAC TTCAGG (SEQ ID NO: 65) | CTCAGGTTCTGGGAG AGGGT (SEQ ID NO: 89) | CTCCATCGTAAGCAAACCTT AGAGG (SEQ ID NO: 112) |
| BUB1B | AGAAATCCTCCCAC TTCGGC (SEQ ID NO: 66) | GCAGATTCTTGTGCC AGTGC (SEQ ID NO: 90) | CAGCTAACAAAGAAGCTTAG GCATATAATA (SEQ ID NO: 113) |
| CAMKI_sg1 | ACAACCCTGCCAAG TGGAAA (SEQ ID NO: 67) | ACTAGGGGAGGGTCA TCCAC (SEQ ID NO: 91) | CATTTTATAAAGGGGCAATTT AAGGCTTAG (SEQ ID NO: 114) |
| CAMK1_sg2 | ACAACCCTGCCAAG TGGAAA (SEQ ID NO: 67) | ACTAGGGGAGGGTCA TCCAC (SEQ ID NO: 91) | CATTTTATAAAGGGGCAATTT AAGGCTTAG (SEQ ID NO: 114) |
| CEL | CTGAGGGTGTAGAG GGGAGG (SEQ ID NO: 68) | GTTCTACCTGGCACC TGTCC (SEQ ID NO: 92) | CCTGAGAGCTCATGAACAAG CAT (SEQ ID NO: 115) |
| Chr8q23_sg1 | CTCGTCAAAACAAG GGTAAGCA (SEQ ID NO: 69) | GTTTGAGTTGACCAA ACGCA (SEQ ID NO: 93) | CAAGGGTAAGCAAAGAAATA AAATCTCTTC (SEQ ID NO: 116) |
| Chr8q23_sg2 | ACCTGTCACATTGC TGCATT (SEQ ID NO: 70) | GTTTGAGTTGACCAA ACGCA (SEQ ID NO: 93) | TTGATTATTTCCTGAAGATCT GATTCAACA (SEQ ID NO: 117) |
| CXCR4 | TTGTGCCCTTAGCC CACTAC (SEQ ID NO: 71) | CCAGAAGGGAAGCG TGATGA (SEQ ID NO: 94) | GTACTTGTCCGTCATGCTTCT CAGTTT (SEQ ID NO: 118) |
| DNMT1 | GATCAAGCTTTGTA TGTTGGCCAA (SEQ ID NO: 72) | AATCCAGAATGCACA AAGTACTGC (SEQ ID NO: 95) | GATCAAGCTTTGTATGTTGG CCAA (SEQ ID NO: 72) |

TABLE 1-continued

Target Sequence Primers

| Target | Primer F | Primer R | Primer Seq |
|---|---|---|---|
| EMX1 | CAGCTCTGTGACCC TTTGTTTG (SEQ ID NO: 73) | ACTAAACTACAGTGG TGCCTGG (SEQ ID NO: 97) | CAGCTCTGTGACCCTTTGTTT G (SEQ ID NO: 73) |
| FAM163A | GAGTGGTGGGAGGG GAAAAG (SEQ ID NO: 74) | CATGTCAGCCGTCCG TATGT (SEQ ID NO: 97) | CTTGCAAAGCTGGGATTAGA AACTT (SEQ ID NO: 119) |
| FANCF | GATATTTCCAAAGC GAAAGGAAGC (SEQ ID NO: 75) | ATCAGAGAGTCCTCC TGGAGATTT (SEQ ID NO: 98) | GATATTTCCAAAGCGAAGG AAGC (SEQ ID NO: 75) |
| GAA | GGTGAGTCTCCTCC AGGACT (SEQ ID NO: 76) | CAGACTGTGCAAGTG CTCTG (SEQ ID NO: 99) | CTTTTCTCGCCCTTCCTTCTG G (SEQ ID NO: 120) |
| GRK1 | GTCTCTCTCGTCCA GCAAGGG (SEQ ID NO: 77) | ATGTCTTTCCAGAGC TCCAGGG (SEQ ID NO: 100) | GTCTCTCTCGTCCAGCAAGG G (SEQ ID NO: 77) |
| ITGA7 | GGTTGTCGCCAAAC CTTCAC (SEQ ID NO: 78) | GGGATTGGGGAGTCA AGAGC (SEQ ID NO: 101) | GAGTCAAGAGCACAAGAAAC ATGAGAACAT (SEQ ID NO: 121) |
| IRAK4 | GCTTCTTGTGTGTGC TGTGAG (SEQ ID NO: 79) | GCCTGTGATTGCTGC ACAAA (SEQ ID NO: 102) | CAAGTTTCTAGTTTAACTTTT TCACAACCA (SEQ ID NO: 122) |
| MAPRE1 | GGTACTCTTGAAGG CAAACTGC (SEQ ID NO: 80) | CGCTGAATGAATATC TGGAACGC (SEQ ID NO: 103) | ACTGCATGAAACTTGCTTTA TAAATTAGG (SEQ ID NO: 123) |
| MIP | TCAGCCAACCATTA CCGTGT (SEQ ID NO: 81) | TAAAGGGGACTGTCC ACCCA (SEQ ID NO: 104) | CATTACCGTGTTGAGTGCTA GGTTTC (SEQ ID NO: 124) |
| OMP | TTGAGAACTGAGTG GGGCTG (SEQ ID NO: 82) | GCGTGTCATGAGGTT GGTGA (SEQ ID NO: 105) | TTGAGAACTGAGTGGGGCTG (SEQ ID NO: 82) |
| OPN1SW | CCCCTAACCCCTTTT TCCCC (SEQ ID NO: 83) | GTTTTGTGGGTGGG AGGAT (SEQ ID NO: 106) | CTAACCCCTTTTTCCCCTGCA GTAC (SEQ ID NO: 125) |
| PRGN | TGAGCTGGGTGGCC TTAACA (SEQ ID NO: 84) | CATTGGCAGGGCCCT TTTATC (SEQ ID NO: 107) | CCAGATGGTCAGTTCTGCCC (SEQ ID NO: 126) |
| PRKAG3_sg1 | ATGTAGGGAGACTG AGGCCA (SEQ ID NO: 85) | GCCCATTGGAAGCTT GCAAA (SEQ ID NO: 108) | TTGGGTCCAACTCTGTGTTAT GGAG (SEQ ID NO: 127) |
| STK3_sg1 | ACGGCAAAACCCTG TCTCAA (SEQ ID NO: 86) | TCCACAGAAAACTCA TAGTAGACTT (SEQ ID NO: 109) | AAACAAGGGTAAGCAAAGA AATAAAATCTC (SEQ ID NO: 128) |
| STK3_sg2 | AAGCCATCCTCATC TGCCTT (SEQ ID NO: 87) | ACACAAGGAATCCG GTCAAGT (SEQ ID NO: 110) | GGAGAAACCCATCTCTACTA AAAATACAAA (SEQ ID NO: 129) |
| VEGFA | GAAGCAACTCCAGT CCCAAATATG (SEQ ID NO: 88) | GTTCACAGCCTGAAA ATTACCCAT (SEQ ID NO: 11) | GAAGCAACTCCAGTCCCAAA TATG (SEQ ID NO: 88) |

Example 12: Analysis of On-Target Editing by CRISPR-OFF Cas9 Complexes in U2OS Cells with and without Exposure to UV Light U2OS cells were maintained between passage 5-15 in RPMI 1640 supplemented with 10% v/v FBS. Cells were passaged weekly at a 1:4 ratio with TrypLE. All cells were maintained at 37° C. and 5% CO2.

U2OS cells were transfected with Cas9 and sgRNAs comprising photocleavable (PC) linkers and were subjected to light filtered with a 345 nm bandpass filter to cleave the linker. Cas9 was complexed with 18 different sgRNAs comprising a photocleavable linker (1-(7-(diethylamino)-2-oxo-2H-chromen-4-yl)propyl), incorporated at positions 57 and 74 (CRISPR OFF) with target binding regions targeting AAVS1 (GGGGCCACUAGGGACAGGAU (SEQ ID NO: 41)), BUB1B(AGUGAAGCCAUGUCCCUGGA (SEQ ID NO: 43)), CAMK1_sg1(UGCCAGGAUCACCUCCGAGA (SEQ ID NO: 44)), CAMK1_sg2 (GCGUCCUCUUAUC-UUCUGCC (SEQ ID NO: 45)), Chr8q23_sg1 (UUAUAGUUACGAUGUUUGAU (SEQ ID NO: 47)), Chr8q23_sg2(AGUCUACUAUGAGUUUUCUG (SEQ ID NO: 130)), DNMT1(GGAGUGAGGGAAACGGCCCC (SEQ ID NO: 49)), EMX1(GAGU-CCGAGCAGAAGAAGAA (SEQ ID NO: 50)), FAM163A (CUGCAGGGCUCGCUGGUGAG (SEQ ID NO: 51)), FANCF(GCUGCAGAAGGGAUUCCAUG (SEQ ID NO: 52)), GRK1(GCCGUCAAAGCUGCCUCGGG (SEQ ID NO: 54)), ITGA7 (GGUGCUGGAGGGCGAGGCUG (SEQ ID NO: 55)), IRAK4(GUCCUGUCUUUGU-CACAGAA (SEQ ID NO: 56)), PRGN(CAGAUGCCUG-CUCAGUGUUG (SEQ ID NO: 61)), PRKAG3 (AGCAAGAAAACAGCAGCUCA (SEQ ID NO: 16)), STK3_sg1(AAAGCAAUACACAAGGAAUC (SEQ ID NO: 62)), STK3_sg2(CCAUAAUGCAGCAAUGUGAC (SEQ ID NO: 63)), and VEGFA(GGUGAGUGAGUGU-GUGCGUG (SEQ ID NO: 64)) to produce 18 experimental populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 345 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 24:
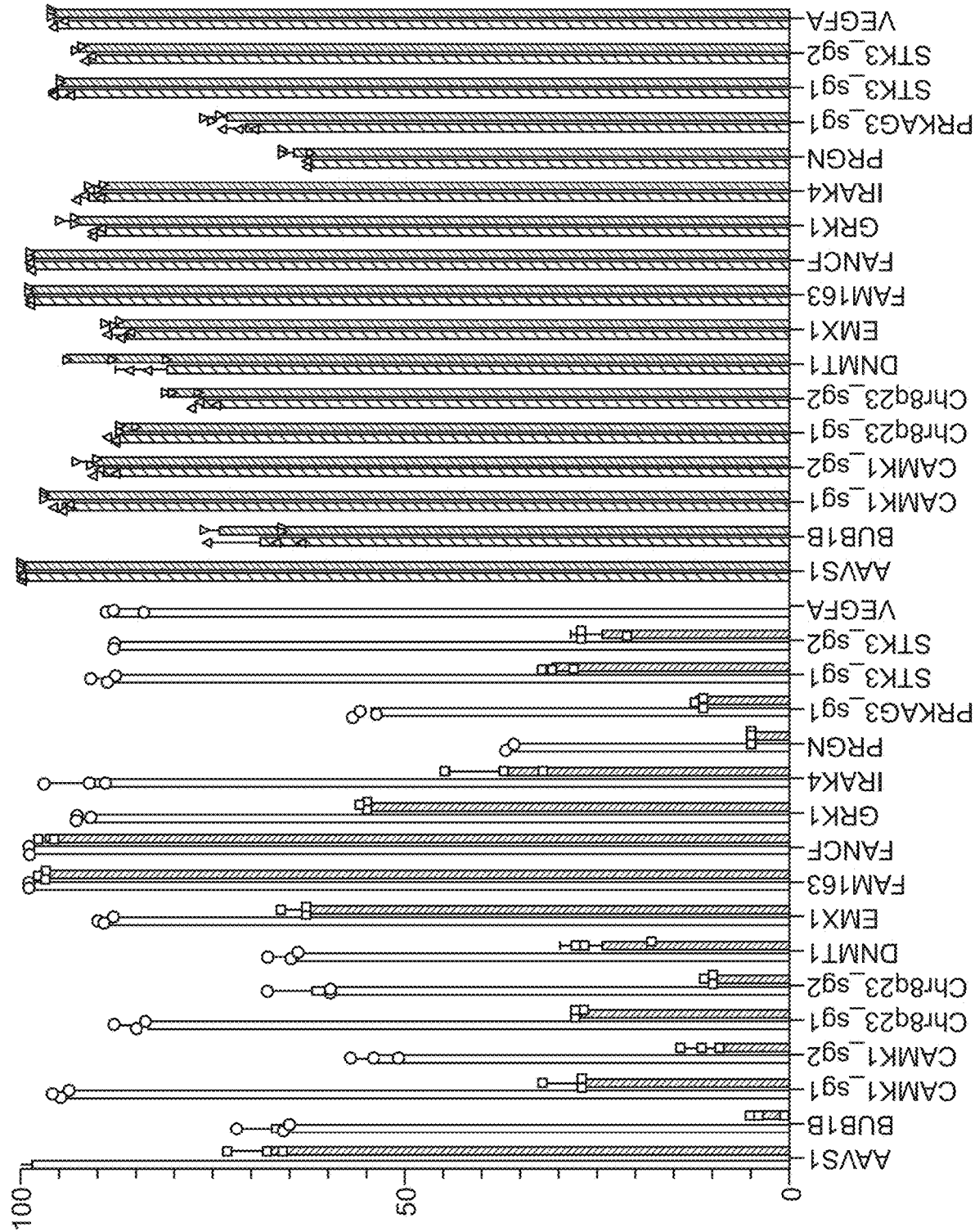
FIG. 24 is a graph comparing the performance, quantified as percent editing, of 18 guide RNAs in Hep3B cells, targeting 18 different target sites, comprising photocleavable linkers at positions 57 and 74, comparing three conditions: without light, with ambient light, or with light at a wavelength greater than 345 nm as compared to sgRNA without photocleavable sites.

FIG. 24 shows a graph of the editing efficiency of Cas9 with the 18 different CRISPR OFF sgRNAs as compared to unmodified sgRNAs with the same target binding sequence.

Example 13: Analysis of On-Target Editing by CRISPR-OFF Cas9 Complexes in Hep3b Cells with and without Exposure to UV Light Hep3B cells were maintained between passage 5-20 in Advanced Modified Eagles Medium (Life Technologies) and 10% v/v FBS. Cells were passaged biweekly at a 1:8 ratio with TrypLE (Life Technologies).

Hep3b cells were transfected with Cas9 and sgRNAs comprising photocleavable (PC) linkers and were subjected to light filtered with a 345 nm bandpass filter to cleave the linker. Cas9 was complexed with 23 different sgRNAs comprising a photocleavable linker (1-(7-(diethylamino)-2-oxo-2H-chromen-4-yl)propyl) incorporated at positions 57 and 74 (CRISPR OFF) with target binding regions targeting AAVS1 (GGGGCCACUAGGGACAGGAU (SEQ ID NO: 41)), BUB1B(AGUGAAGCCAUGUCCCUGGA (SEQ ID NO: 43)), CAMK1_sg1(UGCCAGGAUCACCUCCGAGA (SEQ ID NO: 44)), CAMK1_sg2 (GCGUCCUCUUAUC-UUCUGCC (SEQ ID NO: 45)), CEL (AACCAGUUGCAGGCGCCCCA (SEQ ID NO: 46)), Chr8q23_sg1(UUAUAGUUACGAUGUUUGAU (SEQ ID NO: 47)), CXCR4(GAUAACUACACCGAGGAAAU (SEQ ID NO: 48)), EMX1(GAGU-CCGAGCAGAAGAAGAA (SEQ ID NO: 50)), FAM163A (CUGCAGGGCUCGCUGGUGAG (SEQ ID NO: 51)), FANCF(GCUGCAGAAGGGAUUCCAUG (SEQ ID NO: 52)), GAA(AGGAGCCGGUGGGAGCAGGG (SEQ ID NO: 53)), GRK1(GCCGUCAAAGCUGCCUCGGG (SEQ ID NO: 54)), ITGA7 (GGUGCUGGAGGGCGAGGCUG (SEQ ID NO: 55)), IRAK4(GUCCUGUCUUUGU-CACAGAA (SEQ ID NO: 56)), MAPRE1(UUCU-CUGCAGAUAAUUCCUG (SEQ ID NO: 57)), MIP (GCUGGGGUCCUCACUGCGCU (SEQ ID NO: 58)), OMP(GAACUGUAGCCGCUGCUGCU (SEQ ID NO: 59)), OPN1SW(ACAGGGGCAAUGUGGUACUG (SEQ ID NO: 60)), PRGN(CAGAUGCCUGCUCAGUGUUG (SEQ ID NO: 61)), PRKAG3(AGCAAGAAAACAGCAG-CUCA (SEQ ID NO: 16)), STK3_sg1(AAAGCAAUA-CACAAGGAAUC (SEQ ID NO: 62)), STK3_sg2 (CCAUAAUGCAGCAAUGUGAC (SEQ ID NO: 63)), and VEGFA(GGUGAGUGAGUGUGUGCGUG (SEQ ID NO: 64)) to produce 23 experimental populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 420 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 25:
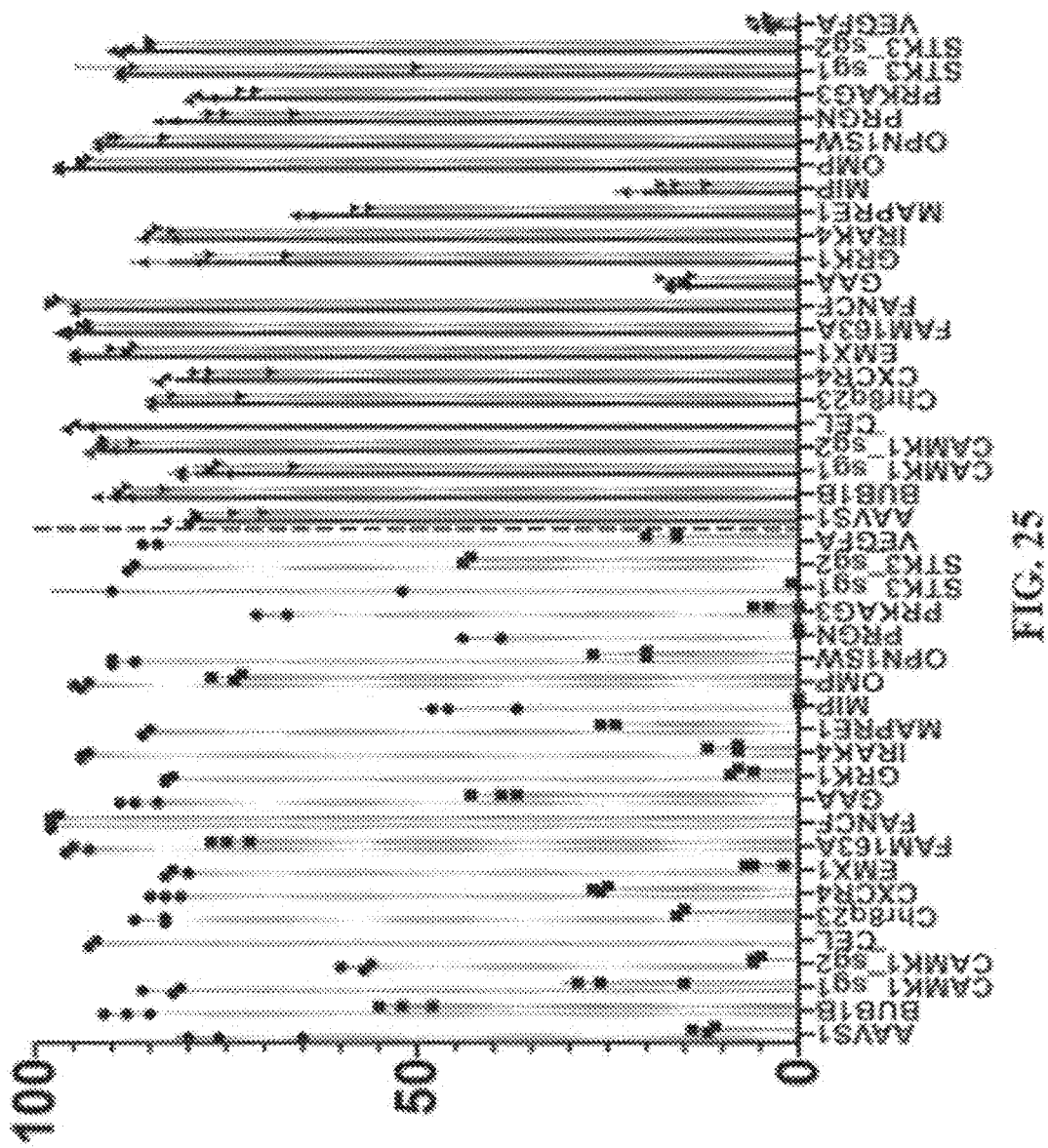
FIG. 25 is a graph comparing the performance, quantified as percent editing, of 13 guide RNAs in U2OS cells, targeting 13 different target sites, comprising photocleavable linkers at positions 57 and 74, comparing three conditions: without light, with ambient light, or with light at a wavelength greater than 345 nm as compared to sgRNA without photocleavable sites.

FIG. 25 shows a graph of the editing efficiency of Cas9 with the 23 different CRISPR OFF sgRNAs as compared to unmodified sgRNAs with the same target binding sequence.

Figure 18:
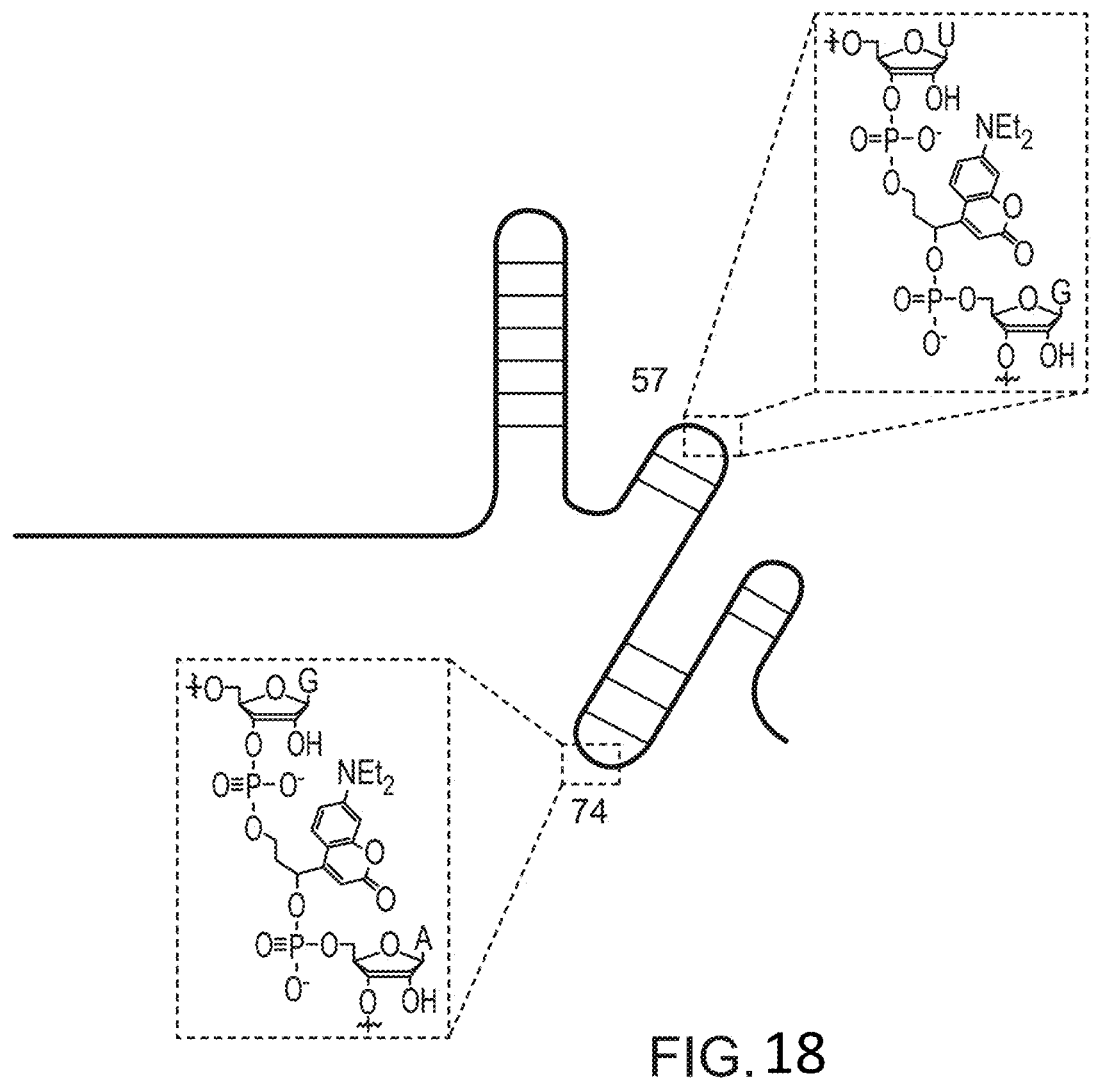
FIG. 18 illustrates exemplary positions at which a modification comprising a coumarin linker can be made to a CRISPR polynucleotide.
Figure 19:
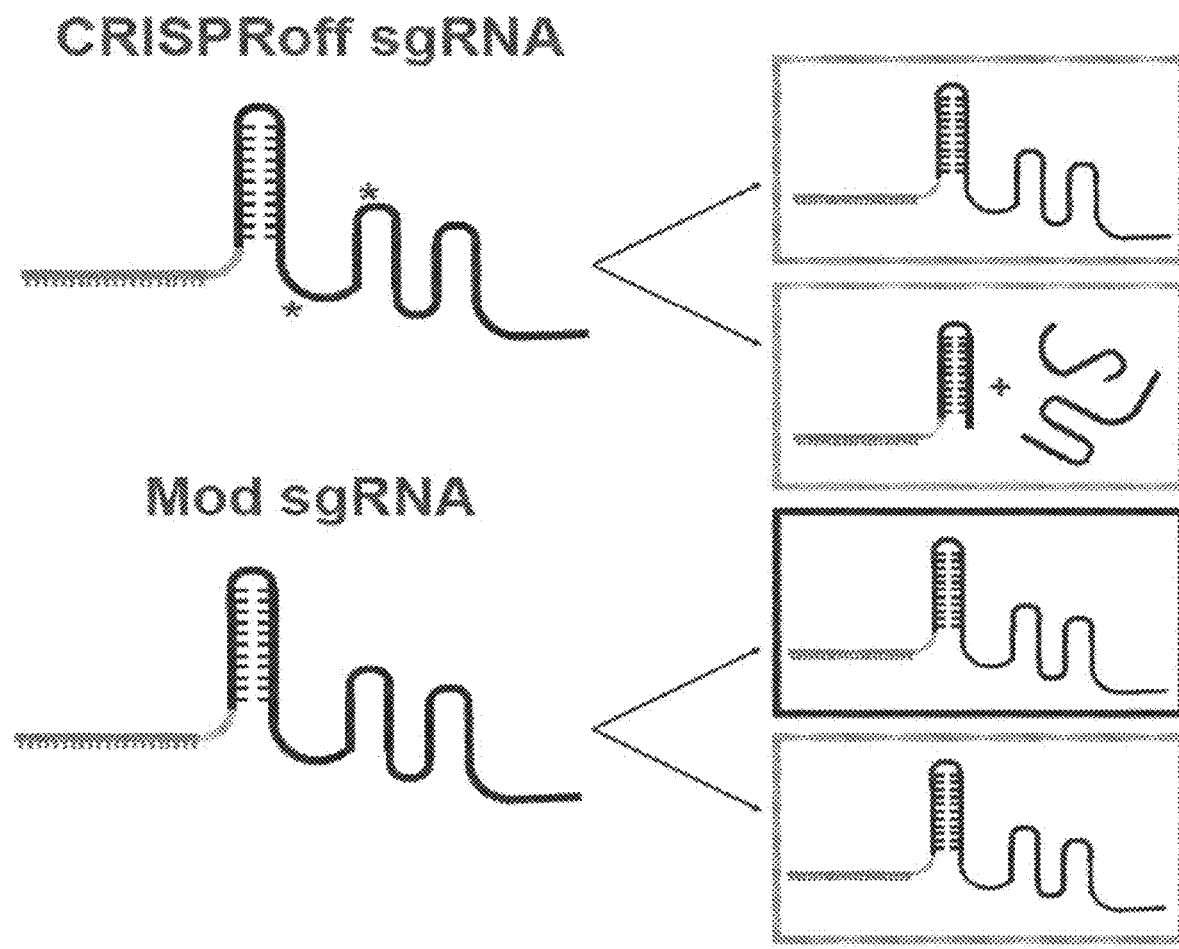
FIG. 19 illustrates exemplary positions at which a modification comprising a cleavable linker can be made to CRISPR polynucleotide as compared to a modified sgRNA without cleavable linkers.

Example 14: Exposure of CRISPR OFF sgRNA with a Coumarin Linker to Visible Light FIG. 18 is a diagram of a CRISPR polynucleotide comprising a coumarin linker, diethylaminocoumarin (1-(7-(diethylamino)-2-oxo-2H-chromen-4-yl)propyl) at positions 57 and 74 of an sgRNA. The coumarin linker is significantly red-shifted and can be used to cleave oligonucleotides using visible light. Coumarin linker release occurs through the formation of a tight ion pair, followed by a reaction of coumarinylmethyl cation with water and other available nucleophiles.

Electrospray Ionization

RNA samples in TE buffer (3 uM) were analyzed by mass spectrometry (Agilent 1290 Infinity II liquid chromatography system (LC) coupled with Agilent 6530B Q-TOF mass spectrometer (MS)) in a negative ion polarity mode. LC is performed with gradient elution (buffer A: 50 mM HFIP; 15 mM Hexylamine 2% MeOH; buffer B: MeOH, 0.75 mL/min, 2-95% B in 1.05 min) on a Acquity UPLC BEH C18 VanGuard Pre-column (1.7 um, 2.1×5 mm). Electrospray ionization performed with a dual ESI source (gas temp 325° C., drying gas 12 L/min, nebulizer 40 psi, Vcap 4 kV, fragmentor 250, skimmer 65). Data acquired in 100-3200 m/z range and deconvoluted in 4000-35000 m/z range.

Figure 20A:
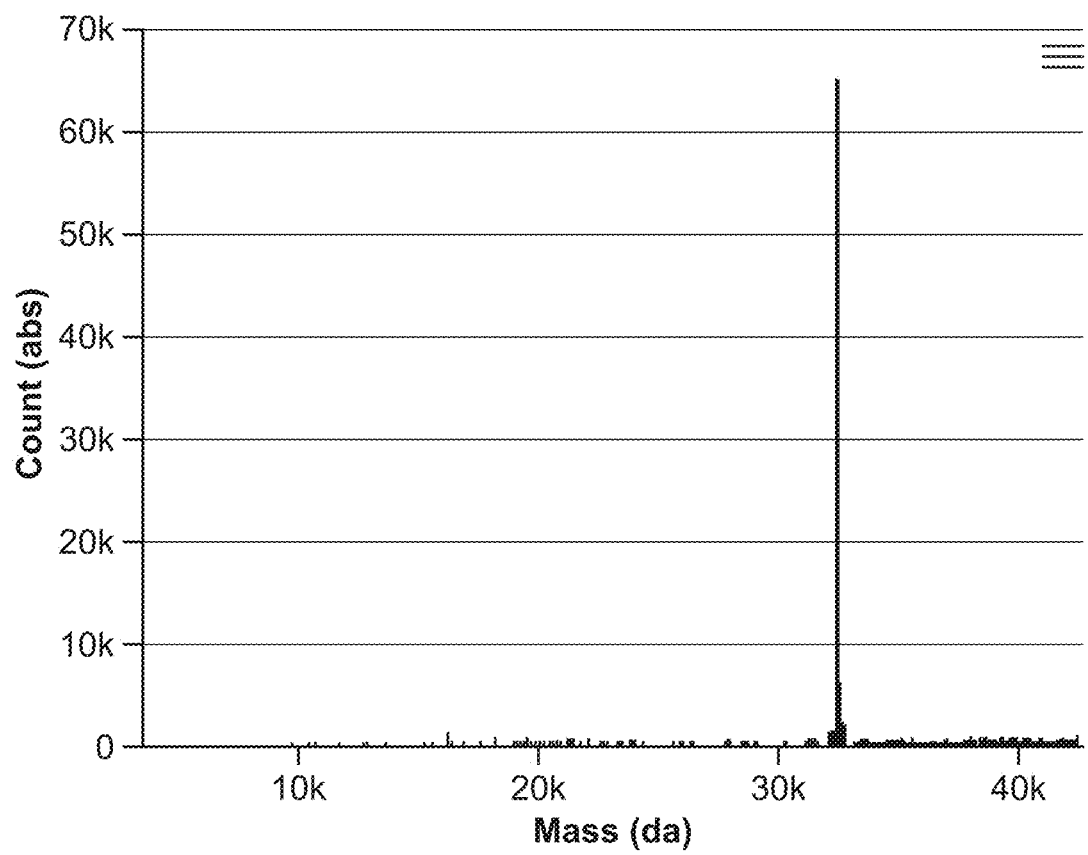
FIG. 20A is an Electrospray Ionization (ESI) Mass Spectrometry trace of an intact CRISPR polynucleotide of FIG. 18 demonstrating that fragmentation is not observed in the absence of light.

FIG. 20A is an ESI trace of the CRISPR OFF sgRNA described above, targeting VEGFA (GGUGAGUGAGUGUGUGCGUG (SEQ ID NO: 64)) before exposure to light.

Figure 20B:
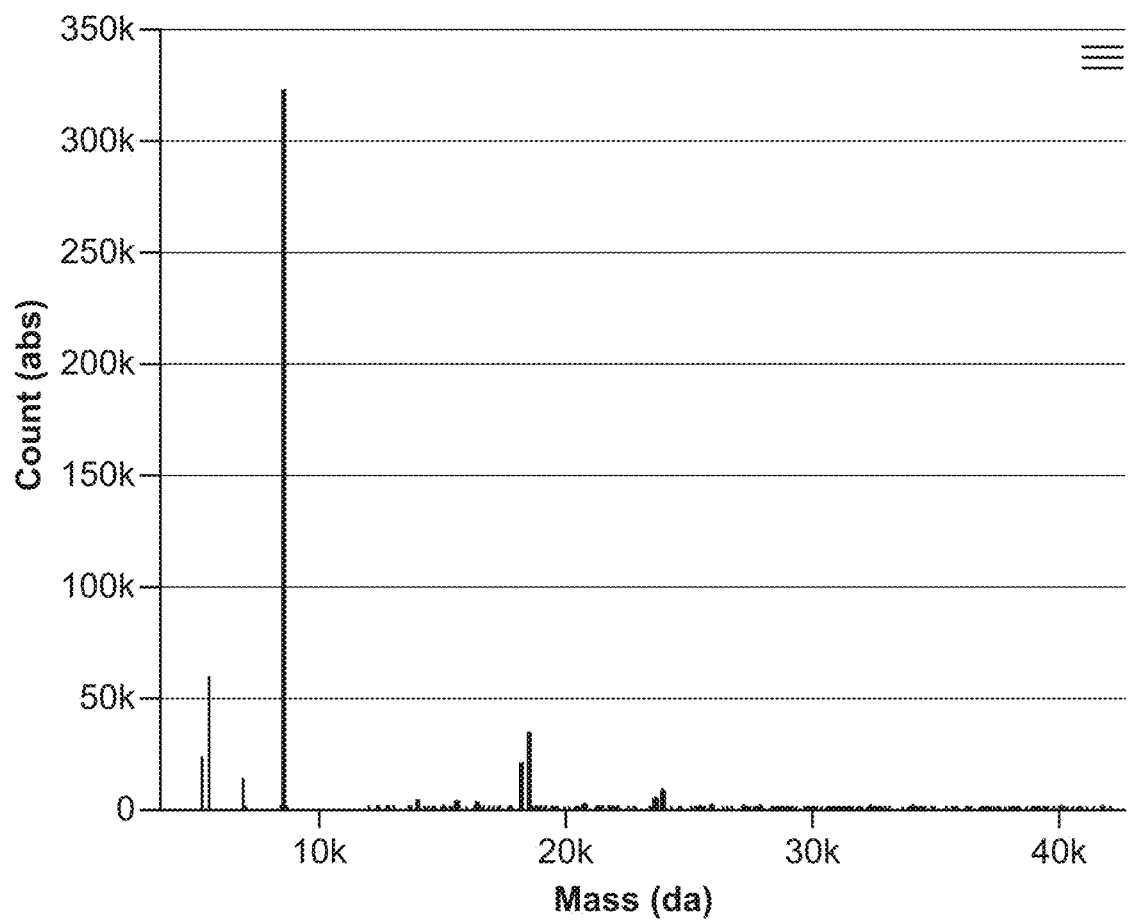
FIG. 20B is an Electrospray Ionization (ESI) Mass Spectrometry trace of a CRISPR polynucleotide of FIG. 18 following photocleavage, demonstrating that the polynucleotide is cleaved at both photocleavable sites upon exposure to light at a wavelength greater than 420 nm.
Figure 21:
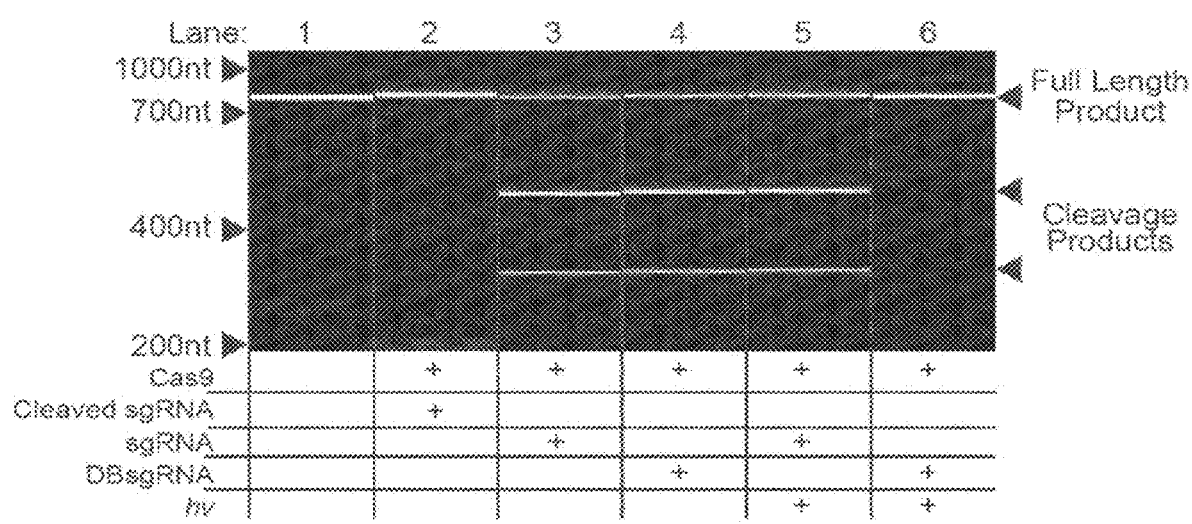
FIG. 21 is picture of a gel showing the comparison of polynucleotide fragments corresponding to the fragments created after the cleavage of photocleavable linkers at positions 57 and 74 after exposure to UV light, fragments created after exposure to UV light, and intact sgRNA.

FIG. 20B is an ESI trace of the CRISPR OFF sgRNA described above after exposure to light filtered through a 420 nm longpass filter. CRISPR OFF sgRNA not subjected to the light retained the same molecular weight as unmodified sgRNA. Fragmentation was not observed for CRISPR OFF sgRNA not subjected to light. FIG. 20B demonstrates that the CRISPR off sgRNA was cleaved at both photocleavable sites upon exposure to 420 nm light.

Example 15: Exposure of CRISPR OFF sgRNA with a UV Cleavable Linker to UV Light

Electrospray Ionization

RNA samples in TE buffer (3 uM) were analyzed by mass spectrometry (Agilent 1290 Infinity II liquid chromatography system (LC) coupled with Agilent 6530B Q-TOF mass spectrometer (MS)) in a negative ion polarity mode. LC is performed with gradient elution (buffer A: 50 mM HFIP; 15 mM Hexylamine 2% MeOH; buffer B: MeOH, 0.75 mL/min, 2-95% B in 1.05 min) on an Acquity UPLC BEH C18 VanGuard Pre-column (1.7 um, 2.1×5 mm). Electrospray ionization performed with a dual ESI source (gas temp 325° C., drying gas 12 L/min, nebulizer 40 psi, Vcap 4 kV, fragmentor 250, skimmer 65). Data acquired in 100-3200 m/z range and deconvoluted in 4000-35000 m/z range.

Figure 41A:
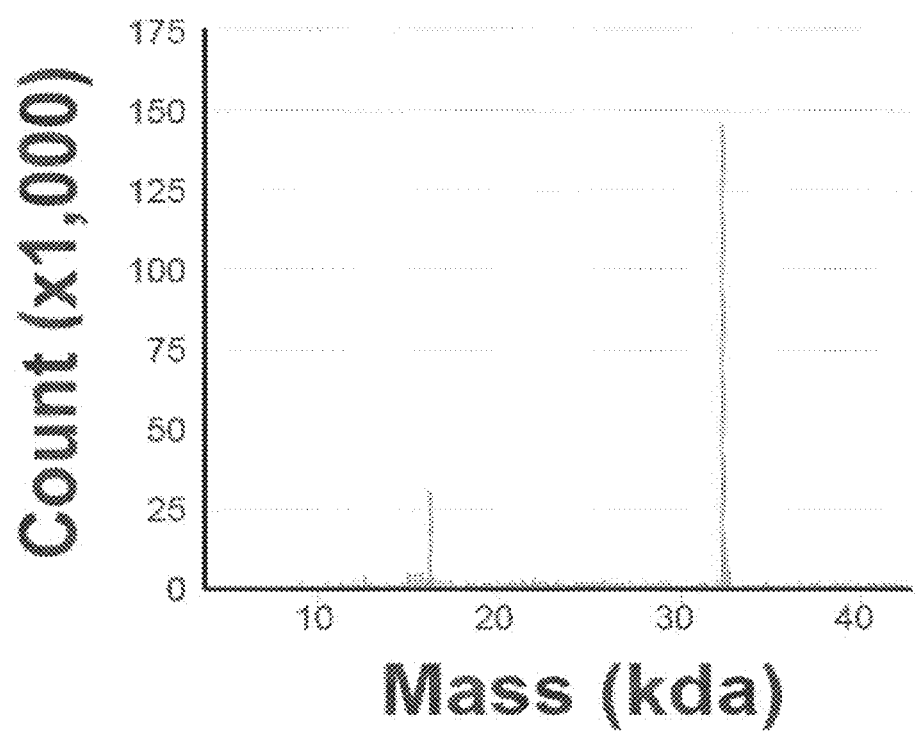
FIG. 41A is an Electrospray Ionization (ESI) Mass Spectrometry trace of an intact CRISPR OFF polynucleotide with photocleavable linkers at positions 57 and 74, demonstrating that fragmentation is not observed in the absence of light.

FIG. 41A is an ESI trace of the CRISPR OFF sgRNA targeting VEGFA (GGUGAGUGAGUGUGUGCGUG (SEQ ID NO: 64)) with photocleavable linkers at positions 57 and 74 before exposure to UV light.

Figure 41B:
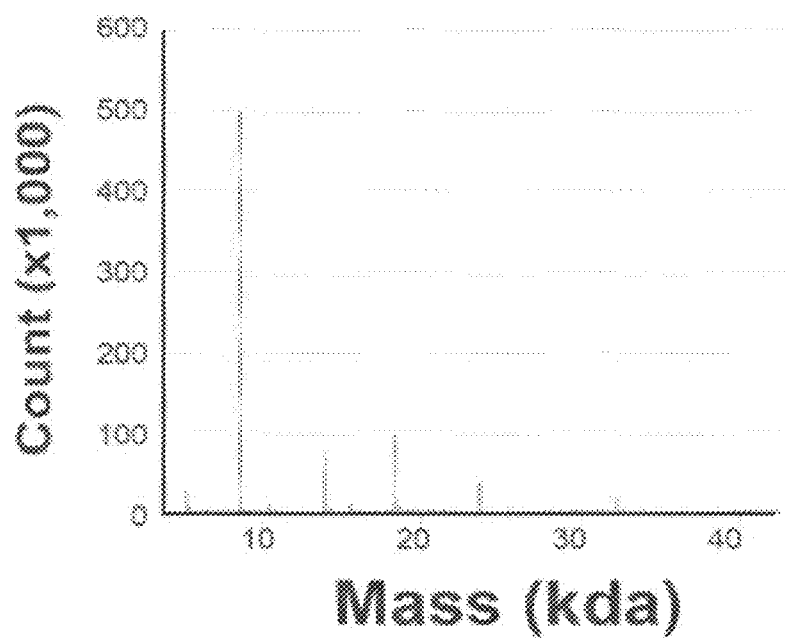
FIG. 41B is an Electrospray Ionization (ESI) Mass Spectrometry trace of a CRISPR OFF polynucleotide with photocleavable linkers at positions 57 and 74, following photocleavage, demonstrating that the polynucleotide is cleaved at both photocleavable sites upon exposure to light at a wavelength greater than 345 nm.

FIG. 41B is an ESI trace of the CRISPR OFF sgRNA of FIG. 41A after exposure to light filtered through a 345 nm bandpass filter. CRISPR OFF sgRNA not subjected to the light retained the same molecular weight as unmodified sgRNA. FIG. 41B demonstrates that the CRISPR off sgRNA was cleaved at both photocleavable sites upon exposure to 345 nm light.

Example 16: Inactivation of Cas9 in Complex with CRISPR OFF sgRNA with UV Light 10 pmol NLS-Cas9-NLS protein (Aldevron) was combined with 30 pmol synthetic sgRNAs in 20 μL total volume and allowed to complex for 10 minutes. During this incubation, cells were harvested and counted. To the RNP solution 5 μL of cell solution at a concentration of 4*10$^4$ cells/μL was added and gently mixed.

Cell+RNP solution was transfected using the 4D-Nucleofector system (Lonza) in the 20 μL format. Transfections were done according to manufacturer protocol. Following transfection, cells were recovered in culture media and plated into 96-well plates.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Figure 38:
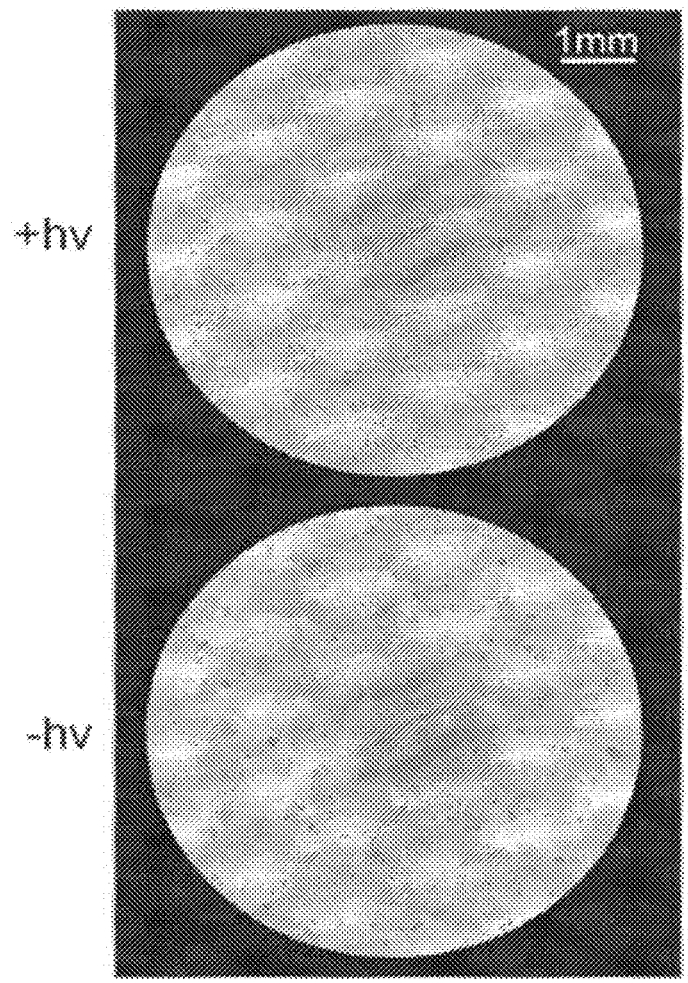
FIG. 38 is a picture of a cell culture wherein the polynucleotide of FIG. 18 in complex with a Cas9 nuclease is used to target an essential gene. The cell culture exposed to light (+hv) demonstrates a higher confluency than the cell culture not exposed to light indicating that the lack of inactivation caused a high degree of cell death.

FIG. 38 is a picture of a cell culture wherein CRISPR OFF in complex with a Cas9 nuclease is used to target an essential gene. The cell culture exposed to light (+hv) demonstrates a higher confluency than the cell culture not exposed to light indicating that the lack of inactivation caused a high degree of cell death.

Figure 26:
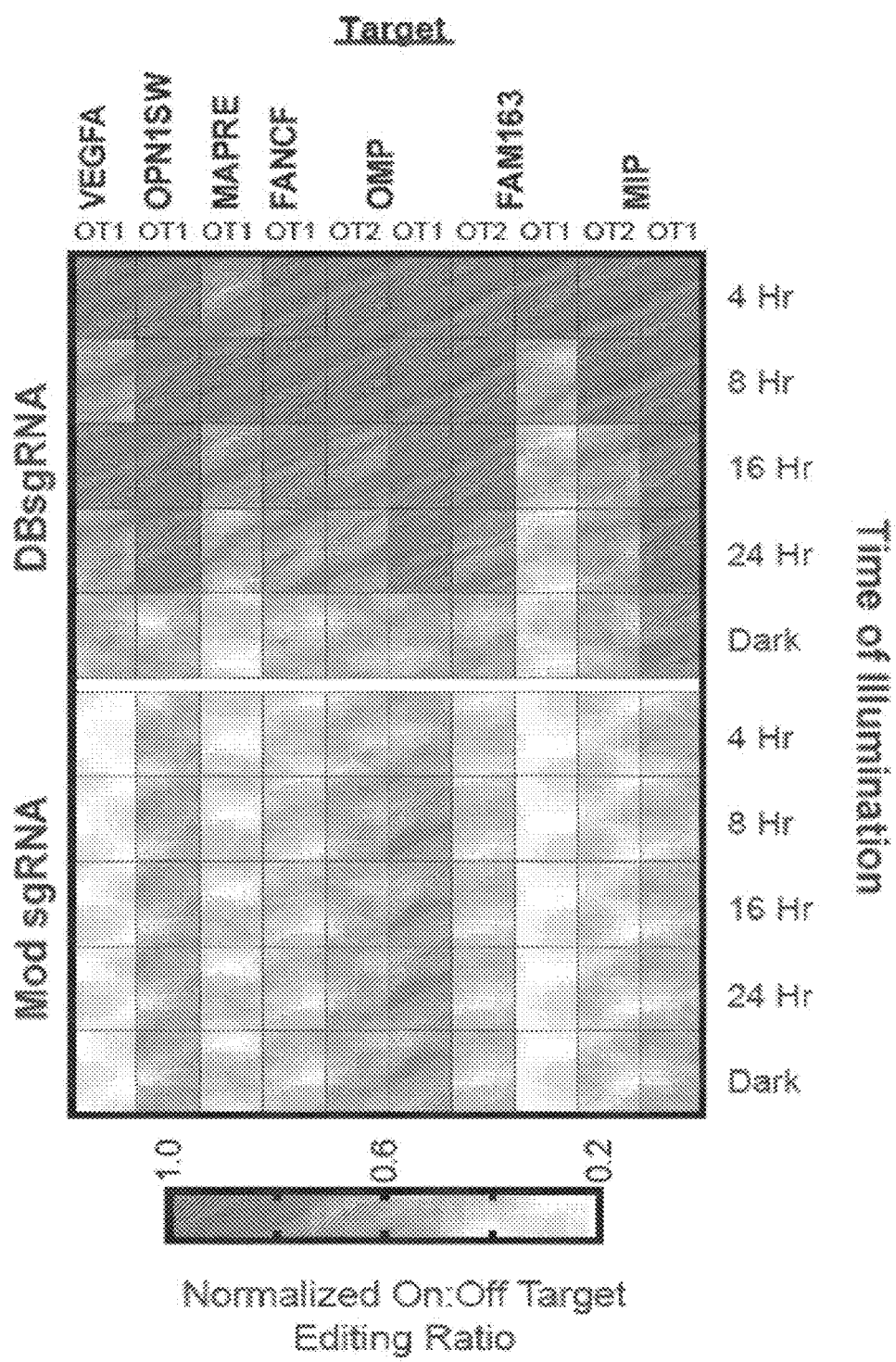
FIG. 26 illustrates relationship between the amount of time that a sgRNA is active and the ratio of on-target editing to off-target editing, demonstrated by an increase in off-target editing the longer sgRNA is allowed to be active, with unmodified sgRNA as the control.

FIG. 26 shows the modulation of the ratio of on-target editing to off-target editing by inactivation of the CRISPR OFF sgRNA before off-target editing occurs, compared to the ratio seen with standard sgRNA. Inactivation of the CRISPR OFF sgRNA was achieved by illuminating cells at discrete times post transfection. Target sites were chosen that had significant levels of off-target editing at one or two sites within the genome as can be seen in Table 2.

Figure 39:
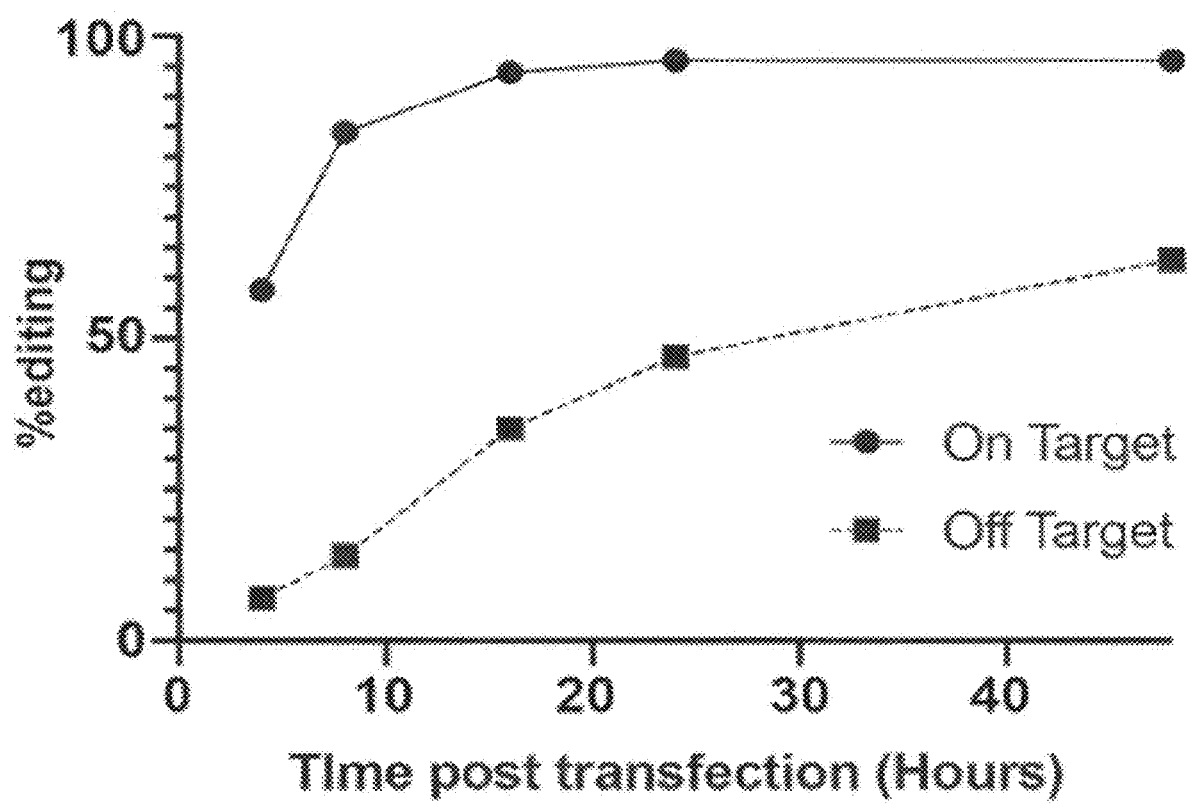
FIG. 39 is a graph showing the ratio of on-target:off-target editing at various time points post transfection.

FIG. 39 is a graph showing the ratio of on-target:off-target editing at the various time points in HEK293 cells post transfection.

TABLE 2

| Off-target sites | |
|---|---|
| Target | Target Sequence |
| MIP_OT1 | AGTGGGGTCCTCACTGCACT (SEQ ID NO: 131) |
| MIP_OT2 | TGTGGGGCACTCACTGCGCT (SEQ ID NO: 132) |
| FAM163_OT1 | CTGCAGGGCCCGCTGGAGAG (SEQ ID NO: 133) |
| FAM163_OT2 | CTGCAGGGGACACTGGTGAG (SEQ ID NO: 134) |
| OMP_OT1 | AGGCTGTAGCCCCTGCTGCT (SEQ ID NO: 135) |
| OMP_OT2 | GAACTACAGCCACTGCTGCT (SEQ ID NO: 136) |
| FANCF_OT1 | GCTGCAGAAGGGATTCCAAG (SEQ ID NO: 38) |
| MAPRE_OTI | ATCTCTGCAGATAATCCCTG (SEQ ID NO: 137) |
| OPNISW_OTI | TTAGAGGCAATGTGGTACTG (SEQ ID NO: 138) |
| VEGFA_OT1 | TGTGGGTGAGTGTGTGCGTG (SEQ ID NO: 139) |

TABLE 3

Off-target sequencing primers

| Target | Primer F | Primer R | Primer Seq |
|---|---|---|---|
| MIP_OT1 | CTCACAGCAAGGTCGACCAC (SEQ ID NO: 140) | CACCCCTACACACTGCCTTT (SEQ ID NO: 150) | CATTCGAAATCCTATGCTGAGCTTTCATAG (SEQ ID NO: 160) |
| MIP_OT2 | CGGCTCCAGTGCTCTTTCTT (SEQ ID NO: 141) | GGAGGGTACGCAAGGTTTGG (SEQ ID NO: 151) | GCCTTTCTGACTCCCATCCTTC (SEQ ID NO: 161) |
| FAM163_OT1 | GTGGATAGGAGCATCTGCCC (SEQ ID NO: 142) | GTGGGAGAAGGAGGTCATGC (SEQ ID NO: 152) | CCTCCCCATATGCTTGGAGTAAG (SEQ ID NO: 162) |
| FAM163_OT2 | GCCCACATTTGCACTGACTC (SEQ ID NO: 143) | GATCATGGTGATGTGCGCAC (SEQ ID NO: 153) | AGACAAGACACCACAGCAATTCCAATTTTG (SEQ ID NO: 163) |
| OMP_OT1 | AGATCCTGGGGGTCTCTGTG (SEQ ID NO: 144) | CGCCTGCTTATCATTTGGGC (SEQ ID NO: 154) | GAACTAGAGACTTATGAGTGGTTCTAAGAT (SEQ ID NO: 164) |
| OMP_OT2 | TTGCAACACCAGGGCTTTCT (SEQ ID NO: 145) | CTTCACAGGCTTCAGGGAGG (SEQ ID NO: 155) | TAGCATTTCCTTCTTTAGAGGTTGATTATG (SEQ ID NO: 165) |
| FANCF_OT1 | AGTTTCACATCCCTGTCTTACCTC (SEQ ID NO: 146) | AGACTCACAACATCCATCAGAACA (SEQ ID NO: 156) | AGTTTCACATCCCTGTCTTACCTC (SEQ ID NO: 146) |
| MAPRE_OT1 | ACAGTTTGTGGGCTTTTTGGT (SEQ ID NO: 147) | GCATTCTGCCCTGTTTGTGG (SEQ ID NO: 157) | CATTTTGAGCAAGGTCAGAAGGAC (SEQ ID NO: 166) |
| OPN1SW_OT1 | TGGCCATAGGAAGCACAGTC (SEQ ID NO: 148) | ATGATCCCCTGTCTCTGCT (SEQ ID NO: 158) | CTACCTCCCTCTCCTTAGCTTCTC (SEQ ID NO: 167) |
| VEGFA_OT1 | AGGGACTTGAGTATCTGCAGTTTT (SEQ ID NO: 149) | TGAAGAGATATCTGCACCCTCATG (SEQ ID NO: 159) | AGGGACTTGAGTATCTGCAGTTTT (SEQ ID NO: 149) |

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Example 17: GFP Knockout Using Cas9-CRISPR OFF 10 pmol NLS-Cas9-NLS protein (Aldevron) was combined with 30 pmol synthetic sgRNAs in 20 uL total volume and allowed to complex for 10 minutes. During this incubation, cells were harvested and counted. To the RNP solution 5 μL of cell solution at a concentration of 4*10⁴ cells/4 was added and gently mixed.

Cell+RNP solution was transfected using the 4D-Nucleofector system (Lonza) in the 20 μL format. Transfections were done according to manufacturer protocol. Following transfection, cells were recovered in culture media and plated into 96-well plates.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Figure 27:
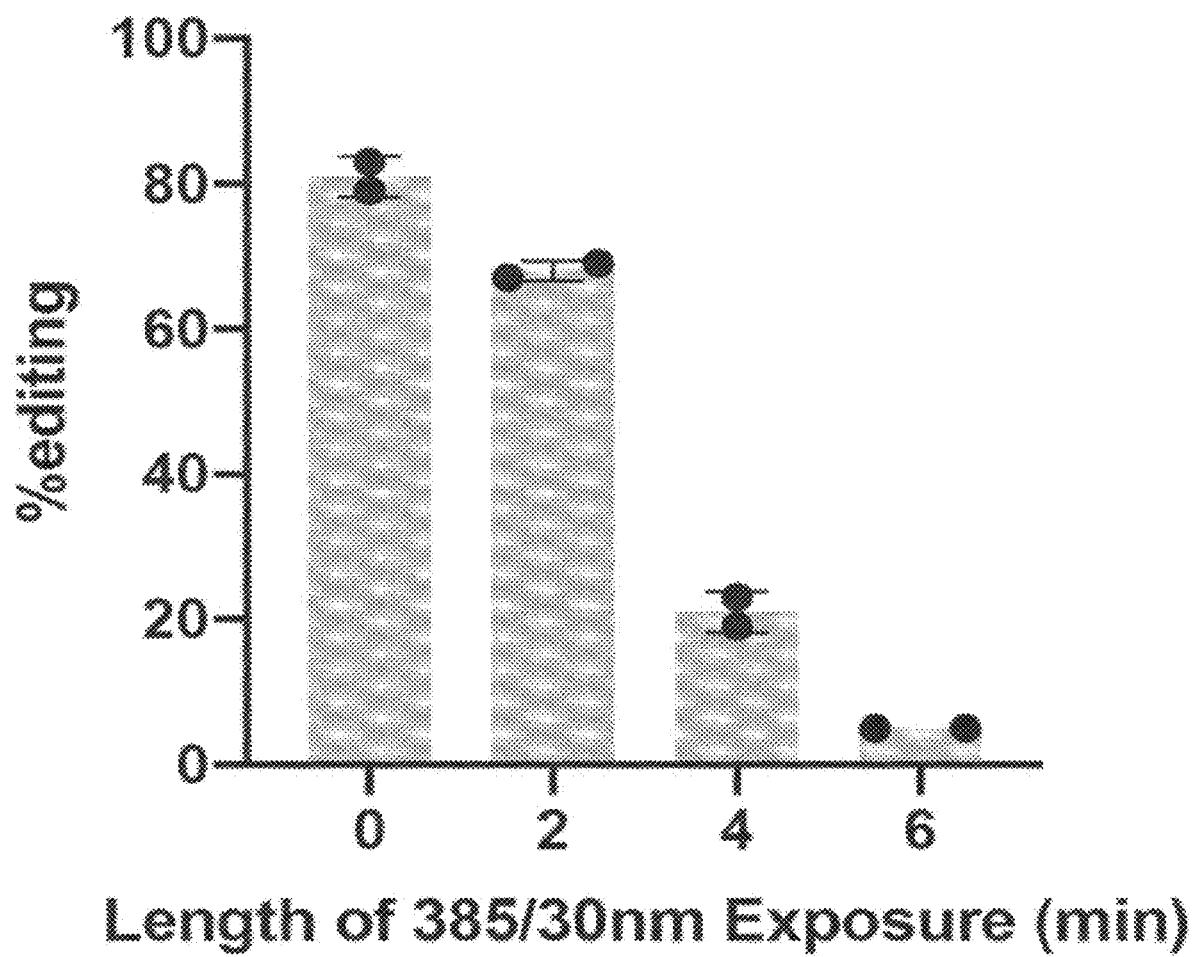
FIG. 27 is a graph showing that the percent editing observed in cells decreases with increased exposure to light at 385 nm.

FIG. 27 is a graph showing that the percent editing observed in cells decreases with increased exposure to light at 385 nm.

Figure 28:
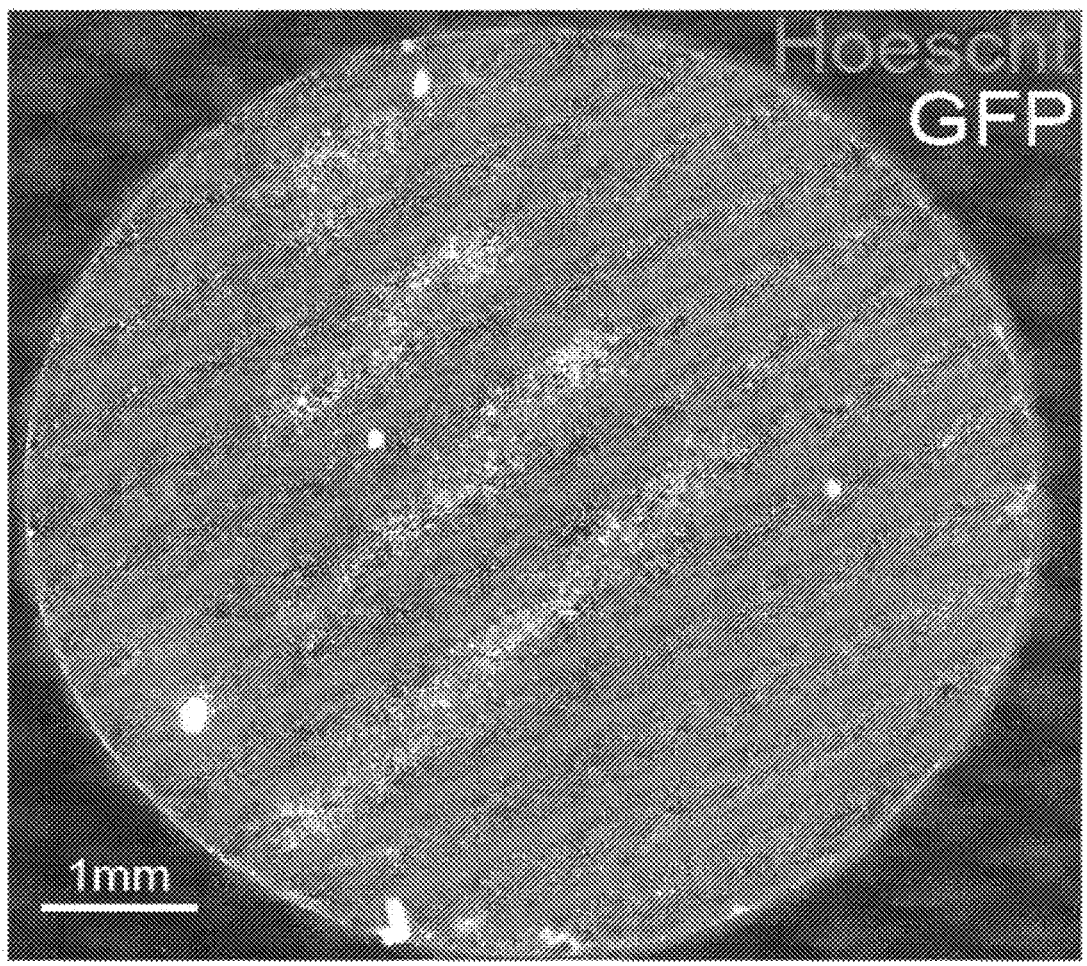
FIG. 28 is an image of a plate of cells selectively masked to prevent some cells from being exposed to light such that the GFP gene is knocked out in those cells kept in the dark, whereas those cells exposed to light express GFP.

FIG. 28 shows a cell culture wherein a mask was used to selectively expose cells expressing CRISPR OFF sgRNA to light to inactivate the gene encoding GFP in cells exposed to light, meanwhile allowing cells unexposed to light to continue to express GFP.

Figure 40:
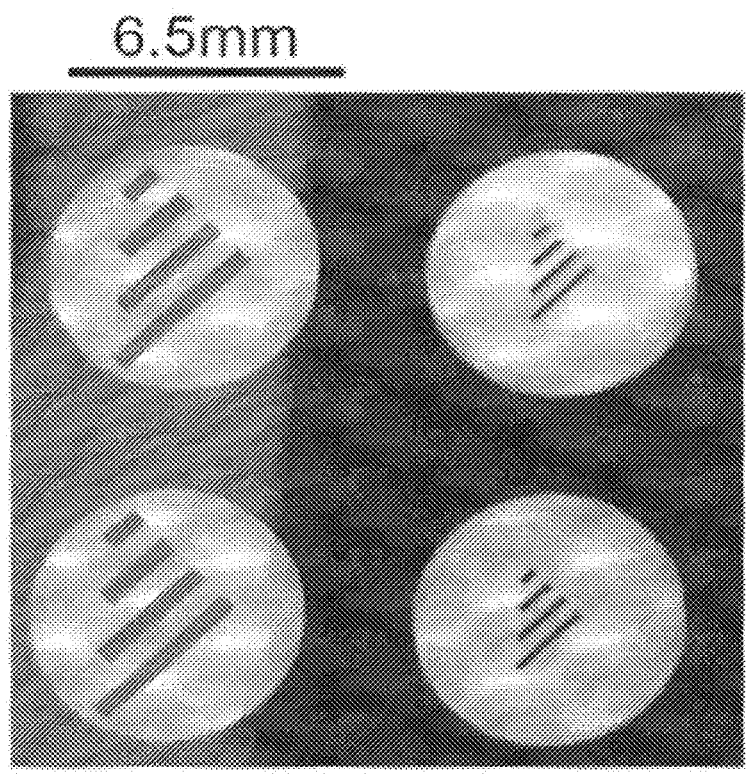
FIG. 40 is a picture of the thin film mask applied to the cell culture of FIG. 28 such that clear areas allowed light to pass through, inactivating the editing activity of the Cas9 nuclease in complex with CRISPR OFF, and dark areas are opaque to allow editing to proceed unimpeded.

FIG. 40 is a picture of the thin film mask applied to the cell culture of FIG. 28 such that clear areas allowed light to pass through, inactivating the editing activity of the Cas9 nuclease in complex with CRISPR OFF, and dark areas are opaque to allow editing to proceed unimpeded.

Figure 32:
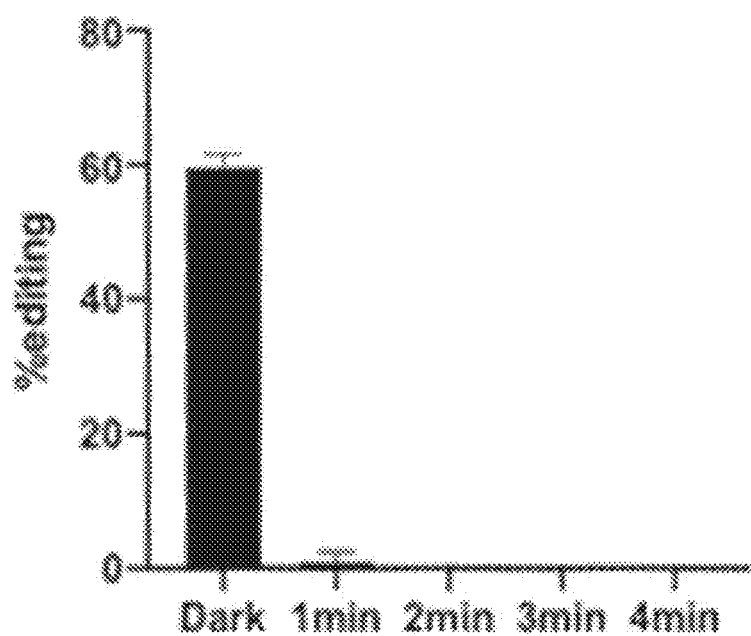
FIG. 32 is a graph showing the time frame in which the CRISPR polynucleotide of FIG. 18 is inactivated by exposure to light with a wavelength of 430±23 nm using the same protocol as FIG. 27.
Figure 33:
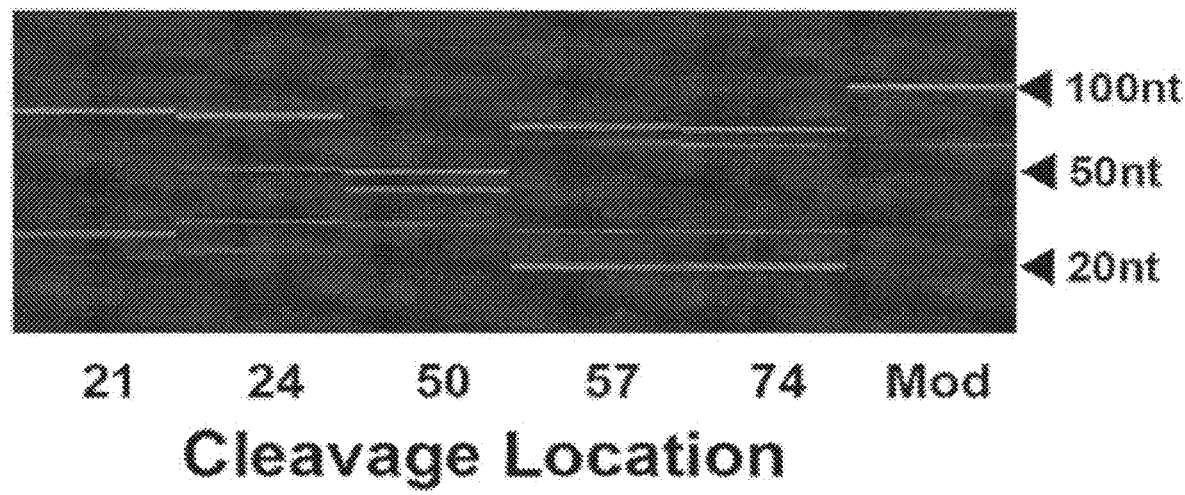
FIG. 33 is a gel showing the cleavage products obtained when a cleavable linker is activated at different locations along the sgRNA.

Example 18: Inactivation of Cas9 in Complex with CRISPR OFF sgRNA with Visible Light FIG. 32 shows how quickly the CRISPR OFF sgRNA targeting MIP, with a coumarin linker at positions 57 and 74, is inactivated by an LED light source. The HEK293 cells transfected with a CRISPR OFF sgRNA with a coumarin linker were split into five independent wells. After four hours, paired replicates were covered to remove ambient light, or exposed to a 430±23 nm LED for 1 min, 2 min, 3 min, or 4 min. One minute was sufficient to inactivate gene-editing. A Colibri 7 light source with 100% intensity of a 430±23 nm LED was used with a standard inverted fluorescent microscope which could illuminate a single well at a time.

Example 19: Testing of Multiple Linker Locations on a sgRNA

RNP Formation and Delivery 10 pmol NLS-Cas9-NLS protein (Aldevron) was combined with 30 pmol synthetic sgRNAs in 20 uL total volume and allowed to complex for 10 minutes. During this incubation, cells were harvested and counted. To the RNP solution 5 µL of cell solution at a concentration of $4*10^4$ cells/µL was added and gently mixed.

Cell+RNP solution was transfected using the 4D-Nucleofector system (Lonza) in the 20 µL format. Transfections were done according to manufacturer protocol. Following transfection, cells were recovered in culture media and plated into 96-well plates.

CRISPR OFF Inactivation

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 34A:
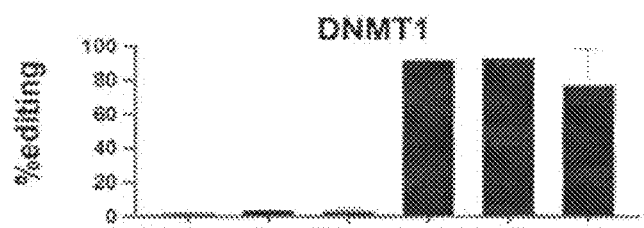
FIG. 34A-C show graphs of the editing activity of various CRISPR OFF cleavable linker locations when targeting different genes.
Figure 34B:
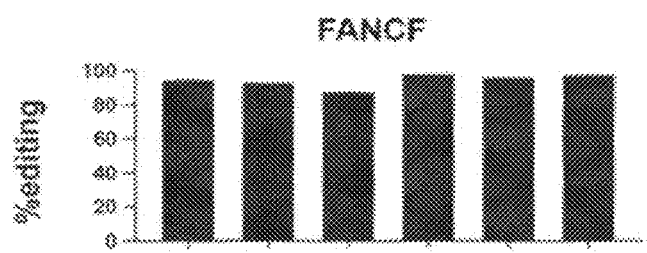
Figure 34C:
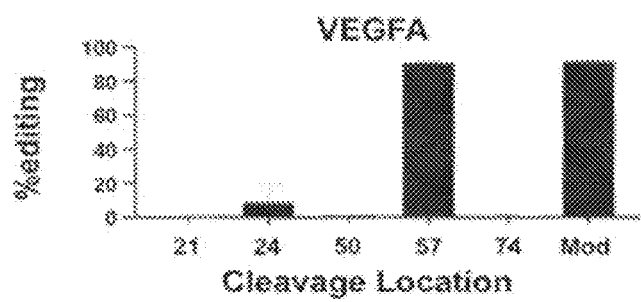

FIGS. 34A-34C show the percent editing observed by eighteen different sgRNAs, in complex with a Cas9 nuclease as described above. FIG. 34A shows the percent editing observed in six different sgRNAs in complex with a Cas9 nuclease, each targeting DNMT1. The sgRNAs are standard (Mod) or have a single cleavable linker at position 21, 24, 50, 57, or 74. FIG. 34B shows the percent editing observed in six different sgRNAs in complex with a Cas9 nuclease, each targeting FANCF. The sgRNAs are standard (Mod) or have a single cleavable linker at position 21, 24, 50, 57, or 74. FIG. 34C shows the percent editing observed in six different sgRNAs in complex with a Cas9 nuclease, each targeting VEGFA. The sgRNAs are standard (Mod) or have a single cleavable linker at position 21, 24, 50, 57, or 74.

Example 20: Droplet PCR to Detect the Fragmentation of CRISPR OFF after Exposure to Light Digital Droplet PCR Cellular RNA was extracted using RNA QuickExtract (Lucigen) without DNase. RNA was quantified using RiboGreen (Thermo Fisher) and normalized.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Total RNA was reverse transcribed using iScript Advanced cDNA Synthesis Kit (BioRad) with 0.4 uM reverse primer for transcription. Reverse transcription product was amplified using 2× EvaGreen ddPCR Mastermix and thermal cycled at 95° C. for 3 minutes followed by 40 cycles of 95° C. for 30 seconds and 52.4° C. for 1 minutes. Signal was then stabilized at 4° C. for 5 minutes followed by inactivation at 90° C. for 5 minutes. Droplets were then read by a QX200 Droplet Digital PCR System (BioRad).

TABLE 4

| ddPCR reagents: | |
|---|---|
| Primer Name | Sequence |
| sgRNA_F | AGAGCTAGAAATAGCAAGTTAAA (SEQ ID NO: 168) |
| sgRNA_R | GACTCGGTGCCACTTT (SEQ ID NO: 169) |

Figure 29:
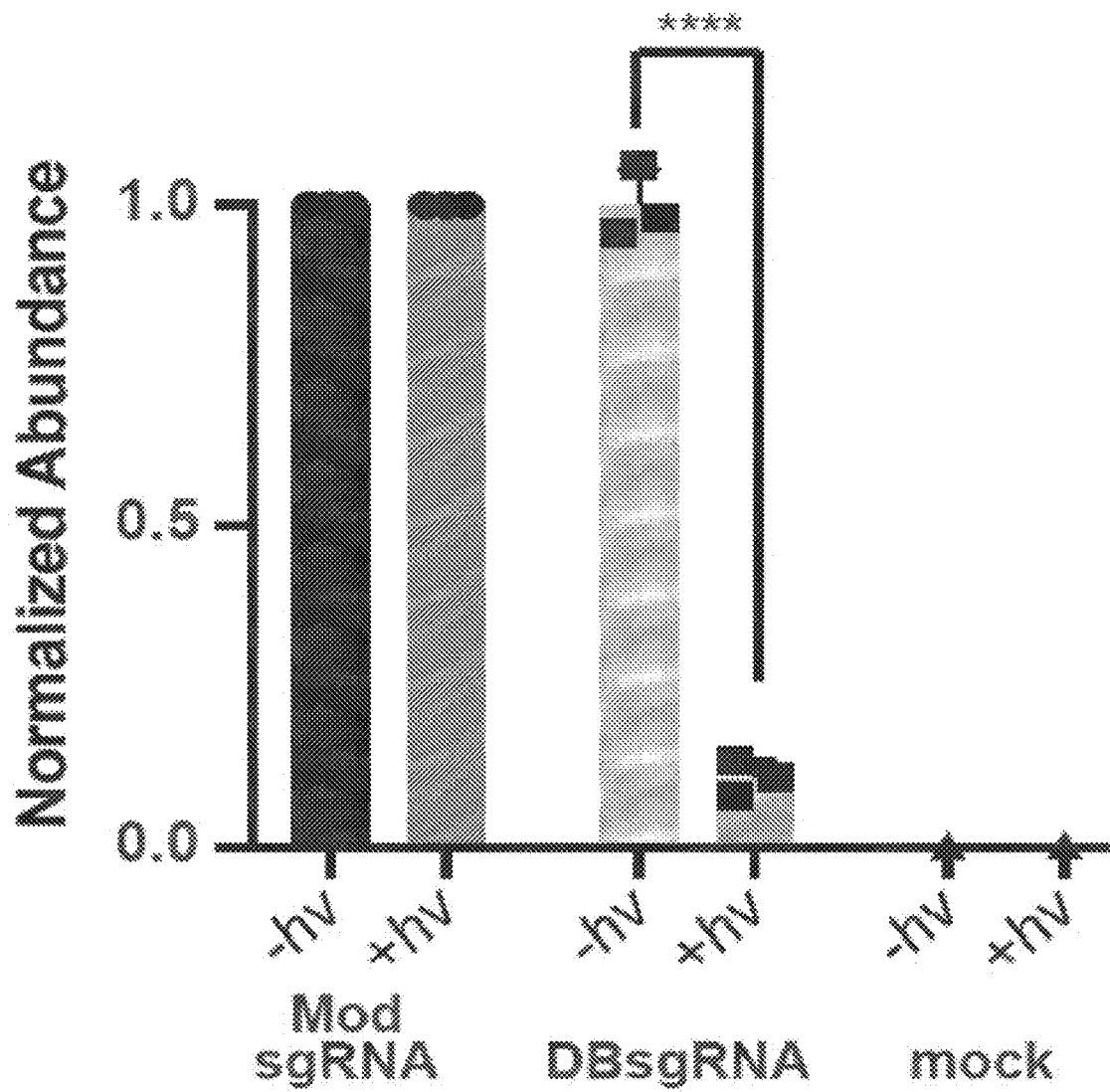
FIG. 29 is a graph showing that the polynucleotide of FIG. 18 decreases in abundance significantly when exposed to light, as compared to sgRNA without photocleavable linkers.

FIG. 29 shows a graph demonstrating the decrease in abundance of CRISPR OFF after exposure to light as compared to standard sgRNA.

Example 21: Preparation of 1-(7-(diethylamino)-2-oxo-2H-chromen-4-yl)propyl

The phosphoramidite compound 3 (3-(bis(4-methoxyphenyl)(phenyl)methoxy)-1-(7-(diethylamino)-2-oxo-2H-chromen-4-yl)propyl (2-cyanoethyl) diisopropylphosphoramidite) is synthesized, following a method disclosed in Wenzel et al. (2003) (NUCLEOSIDES, NUCLEOTIDES & NUCLEIC ACIDS, Vol. 22, Nos. 5-8, pp. 1579-1581), by reacting aldehyde compound 1 (7-(diethylamino)-2-oxo-2H-chromene-4-carbaldehyde) with allyltrimethylsilane in the presence of $TiCl_4$. Next, the diol compound 2 (7-(diethylamino)-4-(1,3-dihydroxypropyl)-2H-chromen-2-one) is generated by ozonolysis of the previous compound and reductive workup with $NaBH_4$. Dimethoxytritylation of 2 followed by phosphitylation yields the phosphoramidite compound 3 in excellent yields.

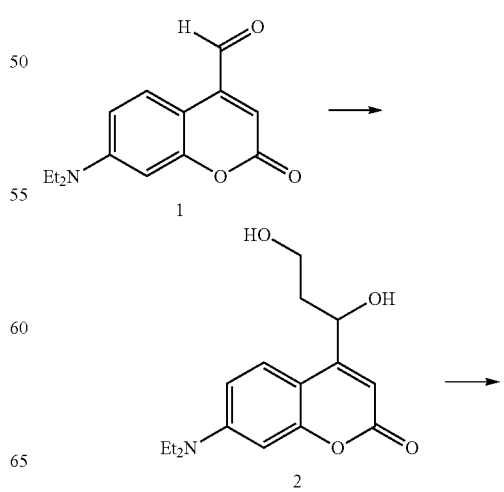

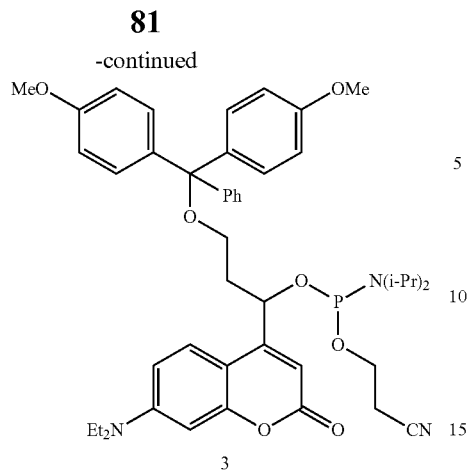

3

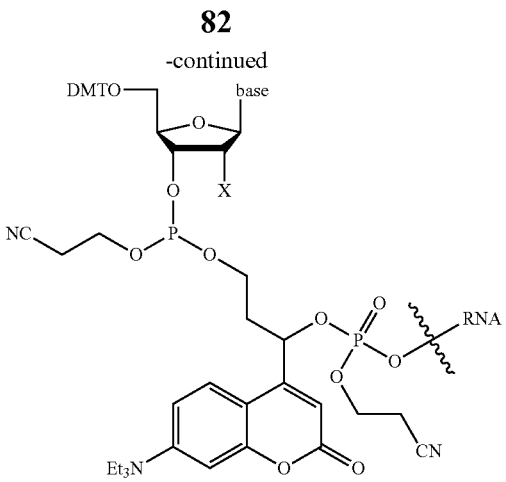

Example 22: Linking 1-(7-(diethylamino)-2-oxo-2H-chromen-4-yl)propyl to a Nucleotide The DMT (DMT=4,4'-dimethoxytrityl) protecting group of the RNA bearing linker formed after addition of compound 3 is removed in an acid-catalyzed detritylation reaction. The detritylated RNA is ready to react with a nucleotide, which is added in the form of a nucleoside phosphoramidite monomer. An appropriate nucleoside phosphoramidite is mixed with an activator (tetrazole or a derivative), both of which are dissolved in acetonitrile. The diisopropylamino group of the nucleoside phosphoramidite is protonated by the activator, and is thereby converted to a good leaving group. It is rapidly displaced by attack of the deprotected hydroxyl group of the detritylated RNA on its neighboring phosphorus atom, and a new phosphorus-oxygen bond is formed, creating a phosphite triester bond (as shown in the figure immediately below). Nucleoside phosphoramidites are reasonably stable in an inert atmosphere and can be prepared in large quantities.

X can be O, S, H, OTBDMS (O-tert-butyldimethylsilyl ether), dicyanomethylene or OMe.

In some embodiments, the diisopropylamino group of the phosphoramidite linker compound 3 is protonated by the activator, and is thereby converted to a good leaving group. It is rapidly displaced by attack of the 3' or 5' hydroxyl group of the nucleoside base, and a new phosphorus-oxygen bond is formed (as shown in the figure immediately below)

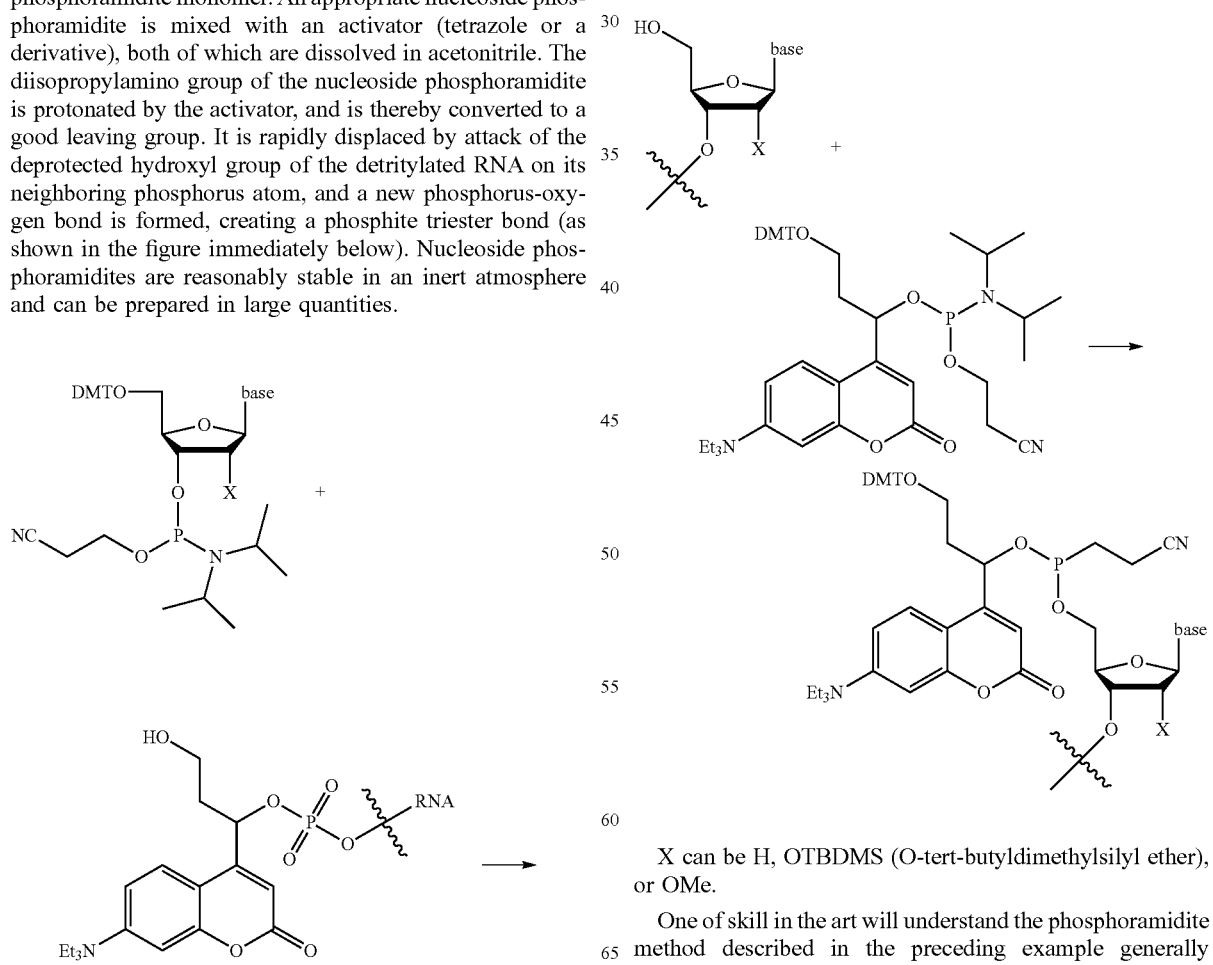

X can be H, OTBDMS (O-tert-butyldimethylsilyl ether), or OMe.

One of skill in the art will understand the phosphoramidite method described in the preceding example generally includes four steps: step 1 (detritylation), step 2 (coupling), step 3 (capping), and step 4 (oxidation).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A CRISPR OFF polynucleotide comprising:
   (a) a guide sequence configured to anneal to a target sequence in a target nucleic acid molecule;
   (b) a sequence configured to bind to a CRISPR enzyme; and
   (c) a cleavable linker positioned at position 57 and/or 74 in the sequence configured to bind to the CRISPR enzyme wherein position 1 is at a 5' end of the guide sequence and positions are counted from 5' to 3', and wherein the CRISPR OFF polynucleotide is inactivated when the cleavable linker is cleaved.

2. The CRISPR OFF polynucleotide of claim 1, wherein the cleavable linker is a photocleavable linker.

3. The CRISPR OFF polynucleotide of claim 1(c), wherein the photocleavable linker is cleaved by visible light.

4. The CRISPR OFF polynucleotide of claim 1(c), wherein the photocleavable linker is cleaved by ultraviolet (UV) light.

5. The CRISPR OFF polynucleotide of claim 1(c), wherein the photocleavable linker comprises a compound of Formula:

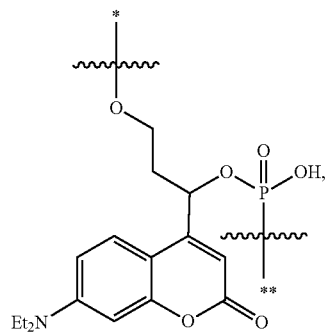

wherein
* indicates a point of attachment to H, or a first nucleotide; and
** indicates a point of attachment to OH, or a second nucleotide.

6. The CRISPR OFF polynucleotide of claim 1(c), wherein the photocleavable linker comprises a compound of Formula:

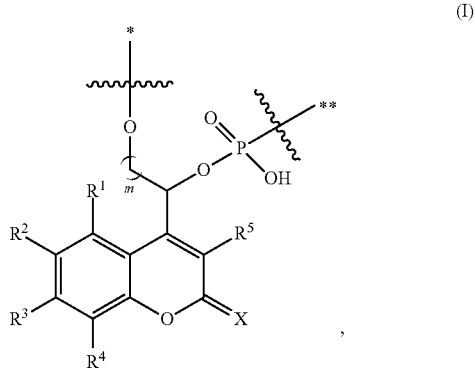

(I)

wherein:
$R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and m is an integer selected from 2 to 10; and
X is selected from O, S, or dicyanomethylene; and
* indicates a point of attachment to H, or a first nucleotide; and
** indicates a point of attachment to OH, or a second nucleotide.

7. The CRISPR OFF polynucleotide of claim 1(c), wherein the CRISPR OFF polynucleotide further comprises a photocaging group.

8. The CRISPR OFF polynucleotide of claim 7, wherein the photocaging group is an ortho-nitrobenzyl group.

9. The CRISPR OFF polynucleotide of claim 1, wherein the cleavable linker is positioned at position 57 and 74, wherein position 1 is at a 5' end of the guide sequence, and positions are counted from 5' to 3'.

* * * * *

```
                           SEQUENCE LISTING

<160> NUMBER OF SEQ ID NOS: 169

<210> SEQ ID NO 1
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 1
nnnnnnnnnn nnnnnnnnnn guuuuagagc uagaaauagc aaguuaaaau aaggcuaguc      60
cguuaucaac uugaaaaagu ggcaccgagu cggugcuuuu                          100

<210> SEQ ID NO 2
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (5)..(24)
<223> OTHER INFORMATION: a, c, u, g, unknown or other

<400> SEQUENCE: 2
gaaannnnnn nnnnnnnnnn nnnnguuuua gagcuagaaa uagcaaguua aaauaaggcu      60
aguccguuau caacuugaaa aaguggcacc gagucggugc uuuu                     104

<210> SEQ ID NO 3
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (11)..(30)
<223> OTHER INFORMATION: a, c, u, g, unknown or other

<400> SEQUENCE: 3
ugagaaauca nnnnnnnnnn nnnnnnnnnn guuuuagagc uagaaauagc aaguuaaaau      60
aaggcuaguc cguuaucaac uugaaaaagu ggcaccgagu cggugcuuuu               110

<210> SEQ ID NO 4
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (17)..(36)
<223> OTHER INFORMATION: a, c, u, g, unknown or other
```

<400> SEQUENCE: 4
cacugagaaa ucagugnnnn nnnnnnnnnn nnnnnnguuu uagagcuaga aauagcaagu    60
uaaaauaagg cuaguccguu aucaacuuga aaaaguggca ccgagucggu gcuuuu       116

<210> SEQ ID NO 5
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuuuagagcu agaaauagca aguuaaaaua aggcuagucc guuaucaacu ugaaaaagug    60
gcaccgaguc ggugcuuuu                                                79

<210> SEQ ID NO 6
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uagagcuaga aauagcaagu uaaaauaagg cuaguccguu aucaacuuga aaaaguggca    60
ccgagucggu gcuuuu                                                   76

<210> SEQ ID NO 7
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 7
nnnnnnnnnn nnnnnnnnnn guuuagagc uagaaauagc aaguuaaaa                49

<210> SEQ ID NO 8
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aaggcuaguc cguuaucaac uugaaaaagu ggcaccgagu cggugcuuuu              50

<210> SEQ ID NO 9
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 9
nnnnnnnnnn nnnnnnnnnn guuuuagagc uagaaauagc aaguuaaaau aaggcu    56

<210> SEQ ID NO 10
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guccguuauc aacuugaaaa aguggcaccg agucggugcu uuu    43

<210> SEQ ID NO 11
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 11
nnnnnnnnnn nnnnnnnnnn guuuuagagc uagaaauagc aaguuaaaau aaggcuaguc    60
cguuaucaac uug    73

<210> SEQ ID NO 12
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaguggca ccgagucggu gcuuuu    26

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agtgaagcca tgtccctgga    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgccaggatc acctccgaga    20

<210> SEQ ID NO 15
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcaagaaaa cagcagctca                                                   20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agcaagaaaa cagcagcuca                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcctgaagat ctgattcaac                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaagcaatac acaaggaatc                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccataatgca gcaatgtgac                                                   20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuuaauugcg acaacuugac                                                   20

<210> SEQ ID NO 21
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 21
gtcctgtctt tgtcacagaa                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agtctactat gagttttctg                                                     20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttatagttac gatgtttgat                                                     20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagcctcaaa ttaggagaaa                                                     20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggagtgaggg aaacggcccc                                                     20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gagtccgagc agaagaagaa                                                     20

<210> SEQ ID NO 27
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 27
gctgcagaag ggattccatg                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gccgtcaaag ctgcctcggg                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cagatgcctg ctcagtgttg                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtgagtgag tgtgtgcgtg                                                    20

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ggagtgaggg aaacggcccc gttttagagc tagaaatagc aagttaaaat aaggctagtc        60
cgttatcaac ttgaaaaagt ggcaccgagt cggtgctttt                             100

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagtgaggg aaacggcccc gttttagagc tagaaatagc aagttaaaat aaggct            56

<210> SEQ ID NO 33
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 33
gtccgttatc aacttg                                                   16

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaaagtggca ccgagtcggt gctttt                                        26

<210> SEQ ID NO 35
<211> LENGTH: 20
<212> TYPE: DNA
<213> ORGANISM: Homo sapiens

<400> SEQUENCE: 35
ggagggaggg aaacagcccc                                               20

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gctgcagaag ggattccatg gttttagagc tagaaatagc aagttaaaat aaggctagtc   60
cgttatcaac ttgaaaaagt ggcaccgagt cggtgctttt                        100

<210> SEQ ID NO 37
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gctgcagaag ggattccatg gttttagagc tagaaatagc aagttaaaat aaggct       56

<210> SEQ ID NO 38
<211> LENGTH: 20
<212> TYPE: DNA
<213> ORGANISM: Homo sapiens

<400> SEQUENCE: 38
gctgcagaag ggattccaag                                               20

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 39
ggtgagtgag tgtgtgcgtg gttttagagc tagaaatagc aagttaaaat aaggctagtc    60
cgttatcaac ttgaaaaagt ggcaccgagt cggtgctttt                         100

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggtgagtgag tgtgtgcgtg gttttagagc tagaaatagc aagttaaaat aaggct        56

<210> SEQ ID NO 41
<211> LENGTH: 20
<212> TYPE: DNA
<213> ORGANISM: Homo sapiens

<400> SEQUENCE: 41
gctgagtgag tgtatgcgtg                                                20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggggccacua gggacaggau                                                20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
agugaagcca ugucccugga                                                20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ugccaggauc accuccgaga                                                20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
```
gcguccucuu aucuucugcc                                          20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaccaguugc aggcgcccca                                          20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuauaguuac gauguuugau                                          20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gauaacuaca ccgaggaaau                                          20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ggagugaggg aaacggcccc                                          20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gaguccgagc agaagaagaa                                          20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cugcagggcu cgcuggugag                                          20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gcugcagaag ggauuccaug                                             20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aggagccggu gggagcaggg                                             20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gccgucaaag cugccucggg                                             20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ggugcuggag ggcgaggcug                                             20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
guccugucuu ugucacagaa                                             20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uucucugcag auaauuccug                                             20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gcuggggucc ucacugcgcu                                            20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
gaacuguagc cgcugcugcu                                            20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60 acagggcaa ugugguacug                                             20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cagaugccug cucaguguug                                            20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aaagcaauac acaaggaauc                                            20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccauaaugca gcaaugugac                                            20

-continued

```
<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ggugagugag ugugugcgug                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcccctatgt ccacttcagg                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agaaatcctc ccacttcggc                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acaaccctgc caagtggaaa                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgagggtgt agaggggagg                                              20

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctcgtcaaaa caagggtaag ca                                           22

<210> SEQ ID NO 70
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acctgtcaca ttgctgcatt                                                    20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ttgtgccctt agcccactac                                                    20

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gatcaagctt tgtatgttgg ccaa                                               24

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cagctctgtg acccttttgtt tg                                                22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gagtggtggg agggggaaaag                                                   20

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gatatttcca aagcgaaagg aagc                                               24

<210> SEQ ID NO 76
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggtgagtctc ctccaggact                                               20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtctctctcg tccagcaagg g                                             21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggttgtcgcc aaaccttcac                                               20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcttcttgtg tgtgctgtga g                                             21

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggtactcttg aaggcaaact gc                                            22

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tcagccaacc attaccgtgt                                               20

<210> SEQ ID NO 82
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 82
ttgagaactg agtggggctg                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
cccctaaccc cttttccccc                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
tgagctgggt ggccttaaca                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
atgtagggag actgaggcca                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
acggcaaaac cctgtctcaa                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
aagccatcct catctgcctt                                                    20

<210> SEQ ID NO 88
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 88
gaagcaactc cagtcccaaa tatg                                           24

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctcaggttct gggagagggt                                                20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcagattctt gtgccagtgc                                                20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
actaggggag ggtcatccac                                                20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gttctacctg gcacctgtcc                                                20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gtttgagttg accaaacgca                                                20

<210> SEQ ID NO 94
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 94
ccagaaggga agcgtgatga                                                    20

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aatccagaat gcacaaagta ctgc                                               24

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
actaaactac agtggtgcct gg                                                 22

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
catgtcagcc gtccgtatgt                                                    20

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
atcagagagt cctcctggag attt                                               24

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cagactgtgc aagtgctctg                                                    20

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 100
atgtctttcc agagctccag gg                                               22

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gggattgggg agtcaagagc                                                  20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcctgtgatt gctgcacaaa                                                  20

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cgctgaatga atatctggaa cgc                                              23

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
taaaggggac tgtccaccca                                                  20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gcgtgtcatg aggttggtga                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 106
gttttgtggg gtgggaggat                                           20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cattggcagg gcccttttat c                                         21

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gcccattgga agcttgcaaa                                           20

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tccacagaaa actcatagta gactt                                     25

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acacaaggaa tccggtcaag t                                         21

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gttcacagcc tgaaaattac ccat                                      24

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctccatcgta agcaaacctt agagg                                    25

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cagctaacaa agaagcttag gcatataata                               30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cattttataa agggcaatt taaggcttag                                30

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cctgagagct catgaacaag cat                                      23

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
caagggtaag caaagaaata aaatctcttc                               30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ttgattattt cctgaagatc tgattcaaca                               30

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

```
gtacttgtcc gtcatgcttc tcagttt                                        27
```

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

```
cttgcaaagc tgggattaga aactt                                          25
```

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
cttttctcgc ccttccttct gg                                             22
```

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
gagtcaagag cacaagaaac atgagaacat                                     30
```

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
caagtttcta gtttaacttt ttcacaacca                                     30
```

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
actgcatgaa acttgcttta taaatttagg                                     30
```

<210> SEQ ID NO 124
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cattaccgtg ttgagtgcta ggtttc       26

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ctaacccctt tttcccctgc agtac       25

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ccagatggtc agttctgccc       20

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ttgggtccaa ctctgtgtta tggag       25

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
aaacaagggt aagcaaagaa ataaaatctc       30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggagaaaccc atctctacta aaaatacaaa       30

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
agucuacuau gaguuuucug       20

-continued

```
<210> SEQ ID NO 131
<211> LENGTH: 20
<212> TYPE: DNA
<213> ORGANISM: Homo sapiens

<400> SEQUENCE: 131
agtggggtcc tcactgcact                                          20

<210> SEQ ID NO 132
<211> LENGTH: 20
<212> TYPE: DNA
<213> ORGANISM: Homo sapiens

<400> SEQUENCE: 132
tgtggggcac tcactgcgct                                          20

<210> SEQ ID NO 133
<211> LENGTH: 20
<212> TYPE: DNA
<213> ORGANISM: Homo sapiens

<400> SEQUENCE: 133
ctgcagggcc cgctggagag                                          20

<210> SEQ ID NO 134
<211> LENGTH: 20
<212> TYPE: DNA
<213> ORGANISM: Homo sapiens

<400> SEQUENCE: 134
ctgcagggga cactggtgag                                          20

<210> SEQ ID NO 135
<211> LENGTH: 20
<212> TYPE: DNA
<213> ORGANISM: Homo sapiens

<400> SEQUENCE: 135
aggctgtagc ccctgctgct                                          20

<210> SEQ ID NO 136
<211> LENGTH: 20
<212> TYPE: DNA
<213> ORGANISM: Homo sapiens

<400> SEQUENCE: 136
gaactacagc cactgctgct                                          20

<210> SEQ ID NO 137
<211> LENGTH: 20
<212> TYPE: DNA
<213> ORGANISM: Homo sapiens

<400> SEQUENCE: 137
atctctgcag ataatccctg                                          20

<210> SEQ ID NO 138
<211> LENGTH: 20
<212> TYPE: DNA
<213> ORGANISM: Homo sapiens

<400> SEQUENCE: 138
```
ttagaggcaa tgtggtactg                                          20

<210> SEQ ID NO 139
<211> LENGTH: 20
<212> TYPE: DNA
<213> ORGANISM: Homo sapiens

<400> SEQUENCE: 139
tgtgggtgag tgtgtgcgtg                                          20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ctcacagcaa ggtcgaccac                                          20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cggctccagt gctctttctt                                          20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gtggatagga gcatctgccc                                          20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcccacattt gcactgactc                                          20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
agatcctggg ggtctctgtg                                          20

<210> SEQ ID NO 145

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ttgcaacacc agggctttct                                            20

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
agtttcacat ccctgtctta cctc                                       24

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acagtttgtg ggcttttggg t                                          21

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tggccatagg aagcacagtc                                            20

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
agggacttga gtatctgcag tttt                                       24

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
cacccctaca cactgccttt                                            20

<210> SEQ ID NO 151
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ggagggtacg caaggtttgg                                              20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gtgggagaag gaggtcatgc                                              20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gatcatggtg atgtgcgcac                                              20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cgcctgctta tcatttgggc                                              20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cttcacaggc ttcagggagg                                              20

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
agactcacaa catccatcag aaca                                         24

<210> SEQ ID NO 157
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 157
gcattctgcc ctgtttgtgg                                          20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
atgatccccc tgtctctgct                                          20

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tgaagagata tctgcaccct catg                                     24

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cattcgaaat cctatgctga gctttcatag                               30

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gcctttctga ctcccatcct tc                                       22

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cctccccata tgcttggagt aag                                      23

<210> SEQ ID NO 163
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 163
agacaagaca ccacagcaat tccaattttg                                        30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gaactagaga cttatgagtg gttctaagat                                        30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tagcatttcc ttctttagag gttgattatg                                        30

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cattttgagc aaggtcagaa ggac                                              24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ctacctccct ctccttagct tctc                                              24

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
agagctagaa atagcaagtt aaa                                               23

<210> SEQ ID NO 169
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 169
gactcggtgc cacttt                                                    16
```